United States Patent [19]

Kishi et al.

[11] Patent Number: 5,338,865
[45] Date of Patent: Aug. 16, 1994

[54] SYNTHESIS OF HALICHONDRIN B AND NORHALICHONDRIN B

[75] Inventors: Yoshito Kishi, Belmont, Mass.; Francis G. Fang, Durham, N.C.; Craig J. Forsyth, Arlington; Paul M. Scola, Watertown, both of Mass.; Suk K. Yoon, Seoul, Rep. of Korea

[73] Assignee: President and Fellows of Harvard College, Cambridge, Mass.

[21] Appl. No.: 11,104

[22] Filed: Jan. 29, 1993

Related U.S. Application Data

[63] Continuation of Ser. No. 849,769, Mar. 12, 1992, abandoned.

[51] Int. Cl.$^5$ ................ C07D 307/93; C07D 309/00; C07D 323/00
[52] U.S. Cl. .................................... 549/214; 549/264; 549/267
[58] Field of Search ................ 549/214, 264, 267

[56] References Cited

PUBLICATIONS

Aicher et al., "Synthesis Studies Towards Halichondrins", Tetrahedron Letters, vol. 28, No. 30, 1987, pp. 3463-3466.

Aicher et al., "Synthesis Studies Towards Halichondrin B", Dissertation Abstracts International, vol. 50, No. 12, 1990, p. 5619-B.

Angyl et al., "Complexes of Carbohydrates with Metal Cations. V* Syntheses of Methyl Glycosides in the Presence of Metal Ions", Australian Journal of Chemistry, vol. 28, No. 7, 1975, pp. 1541-1549.

Bai et al., "Halichondrin B and Homohalichondrin B, Marine Nature Products Binding in the Vinca Domain of Tubulin", The Journal of Biological Chemistry, vol. 266, No. 24, 1991, pp. 15882-15889.

Banaszek et al., "Oxyamination of Unsaturated Sugar Derivatives. Part II*. Synthesis of Alkyl 2-Deoxy- and 2,6-Dideoxy-2-p-Toluenesulfonamide- and 3-deoxy- and 3,6-dideoxy-3-p-Toluenesulfonamido-α-D-MANNO- and TALO-Hexo-Pyranosides", Polish Journal of Chemistry, vol. 53, 1979, pp. 2029-2039.

Brimacombe et al., "A Synthesis of 2-O-Methyl-L-lyxose, a Component of Everninomicins B and D", Journal of the Chemical Society, 1971, pp. 2911-2915.

Brimacombe et al., "The Oxidation of Some Carbohydrate Derivatives, Using Acid Anhydride-Methyl Sulphoxide Mixtures and the Pfitzner-Moffatt Reagent. Facile Synthesis of 3-Acetamido-3-Deoxy-D-Glucose and 3-Amino-3-Deoxy-D-Xylose", Carbohydrate Research, vol. 3, 1967, pp. 318-324.

Burke et al., "Synthesis of a C(22)→C(34) Halichondrin Precursor via a Double Dioxanone-to-Dihydropyran Rearrangement", Tetrahydron Letters, vol. 32, No. 32, 1991, pp. 3961-3964.

Cannizzo et al., "In Situ Preparation of (μ-Chloro)(-μ-methylene)bis(cyclopentadienyl)(dimethylaluminum) Titanium (Tebbe's Reagent)", J. Org. Chem., vol. 50, 1985, pp. 2386-2387.

Carpita et al., "Stereocontrolled Synthesis of Naturally-Occurring Polyacetylenes Characterized by (E)-1-EN-3-YNE, (E)-1-EN-3,5-Diyne, (1E,5E)-1,5-Dien-3-YNE, and (1E,7E)-1,7-Dien-3,5-Diyne Moieties(*)", Gazzetta Chimica Italiana, 117, 1987, pp. 481-489.

Colvin et al., "One-step Conversion of Carbonyl Compounds into Acetylenes", Journal of The Chemical Society, 5, 1973, pp. 151-152.

Colvin et al., "A Simple Procedure for the Elaboration of Carbonyl Compounds into Homologous Alkynes", (List continued on next page.)

Primary Examiner—James H. Reamer
Assistant Examiner—John D. Peabody
Attorney, Agent, or Firm—Fish & Richardson

[57] ABSTRACT

Novel chemical compounds that can be used to synthesize halichondrin B and norhalichondrin B, and related derivatives, are described. The synthesis of halichondrin B and norhalichondrin B from these compounds also is described.

6 Claims, No Drawings

OTHER PUBLICATIONS

Journal of The Chemical Society, 8, 1977, pp. 869–874.
Commercon et al., "Substitution Des Halogeno–1 Alcynes–1 Par Les Derives Organometalliques Du Cuivre. Acces A Une Nouvelle Classe de Synthons: Application a la synthese du Bombykol", Tetrahydron, vol. 36, No. 9, 1980, pp. 1215–1221.
Cooper et al., "Total Synthesis of Halichondrins: Enantioselective Construction of a Homochiral Pentacyclic C1–C15 Intermediate from D–Ribose", Tetrahedron Letters, vol. 31, No. 27, 1990, pp. 3813–3816.
Drouin et al., "Regiocontrolled Cyclisation of Acetylenic Ketones. First Example of Selective Desilylation of a Triple Bond in Presence of a Silyl Enol Ether", Tetrahedron Letters, vol. 28, No. 34, 1987, pp. 3923–3926.
Evans et al., "Monomolar Acetalations of Methyl α–D–Mannosides–Synthesis of Methyl α–D–Talopyranoside", Carbohydrate Research, vol. 54, No. 1, 1977, pp. 105–114.
Gilbert et al., "Elaboration of Aldehydes and Ketones to Alkynes: Improved Methodology", Journal of Organic Chemistry, vol. 44, No. 26, 1979, pp. 4997–4998.
Gorin, P. A. J. et al., "Hydrogenolysis of Carbohydrates: VIII. Comparative Studies on Methyl Glycopyranosides", Can. J. Chem., vol. 38, 1960, pp. 641–651.
Hirata, Yoshimasa et al., "Halichondrins–antitumor polyether macrolides from a marine sponge", Pure & Appl. Chem., vol. 58, No. 5, 1986, pp. 701–709.
Horton, Derek et al., "Selective silylation of 6–deoxyglycals", Carbohydrate Research, vol. 144, 1985, pp. 325–330.
Inanaga, Junji et al., "A Rapid Esterification by Means of Mixed Anhydride and Its Application to Large–ring Lactonization", Bulletin of the Chemical Society of Japan, vol. 52(7), 1979, pp. 1989–1993.
Ireland, Robert E. et al., "3–Acyltetramic Acid Antibiotics. 2. Synthesis of (+)–Streptolic Acid", J. Am. Chem. Soc., vol. 110, 1988, pp. 854–860.
Ireland, Robert E. et al., "The Ester Enolate Claisen Rearrangement. Stereochemical Control through Stereoselective Enolate Formation", Journal of the American Chemical Society, May 12, 1976, pp. 2868–2877.
Ireland, Robert E. et al., "3–Acyltetramic Acid Antibiotics. 1. Synthesis of Tirandamycic Acid", Journal of the American Chemical Society, vol. 103, 1981, pp. 3205–3207.
Jin, Haolun et al., "Catalytic Effect of Nickel(II) Chloride and Palladium(II) Acetate on Chromium(II)–Medicated Coupling Reaction of Iodo Olefins with Aldehydes", J. Am. Chem. Soc., vol. 108, 1986, pp. 5644–5646.
Jirousek, Michael Robert, Ph.D., "Part I. Halichondrin B: Studies on the total synthesis. Part II. Levuglandins: Generation from $PGH_2$ and binding with proteins", Dissertation Abstracts International, vol. 51, No. 2, Aug. 1990, pp. 751B–752B.
Katsuki et al., "The First Practical Method of Asymmetric Epoxidation", J. Am. Chem. Soc., 102, 1980, 5974–5976.
Kim, Seokchan et al., "Total Synthesis of Halichondrins: Highly Stereoselective Construction of a Homochiral Pentasubstituted H–ring Pyran Intermediate from α–D–Glucose", Tetrahedron Letters, vol. 30, No. 46, 1989, pp. 6279–6282.
Kinzy, Willy et al., "Direct 3,6–Di–O–Protection of Glucal and Galactal", Tetrahedron Letters, vol. 28, No. 18, 1987, pp. 1981–1984.
Kishi, Yoshito, "Applications of Ni(II)/Cr(II)–mediated coupling reactions to natural products syntheses", Pure & Appl. Chem., vol. 64, No. 3, 1992, pp. 343–349.
Kishi, "Recent Developments in the Chemistry of Natural Products", Aldrichimica Acta, vol. 13, No. 2, 1980, pp. 23–30.
Kozikowski, Alan P. et al., "A Synthetic Approach to the Cis–Fused Marine Pyranopyrans, (3E)– and (3Z)–Dactomelyne. X–ray Structure of a Rare Organomercurial", J. Org. Chem., vol. 55, 1990, pp. 863–870.
Lewis et al., "Highly Stereoselective Approaches to α– and β–C–Glycopyranosides", J. Am. Chem. Soc., 104, 1982, pp. 4976–4978.
Mahoney, Wayne S. et al., "Selective Hydride–Mediated Conjugate Recution of α,β–Unsaturated Carbonyl Compounds Using $[Ph_3P)CuH]_6$", J. Am. Chem. Soc., vol. 110, 1988, pp. 291–293.
Mahoney, Wayne S. et al., "Hydride–Mediated Homogeneous Catalysis. Catalytic Reduction of α,β–Unsaturated Keytones Using $[Ph_3P)CuH]_6$", J. Am. Soc., vol. 111, 1989, pp. 8818–8823.
Mancuso et al., "Oxidation of Long–Chain and Related Alcohols to Carbonyls by Dimethyl Sulfoxide 'Activated' by Oxalyl Chloride", J. Org. Chem., vol. 43, No. 12, 1978, pp. 2480–2482.
Mitsunobo, Dyo, "The Use of Diethyl Azodicarboxy–

(List continued on next page.)

OTHER PUBLICATIONS late and Triphenylphosphine in Synthesis and Transformation of Natural Products", Int'l. Journal of Methods in Synthetic Organic Chemistry, vol. 1/Jan. 1981, pp. 1-28.

Nakata et al., "Synthetic Studies of Rifamycins. II. Syntheses of Methyl 2,4,6,7-Tetra-deoxy-4-C-methyl-3-O-methyl-α-L-arabino-heptopyranosid-6-ulose and Its Derivatives Utilizable in the Construction of the Rifamycin Ansa Chain Portion", Bull. Chem. Soc. Jpn., 53, 1980, pp. 3252-3258.

Oikawa, Yuji et al., "Specific Removal of o-Methoxybenzyl Protection by DDQ Oxidation", Tetrahedron Letters, vol. 23, No. 8, 1982, pp. 885-888.

Oikawa, Yuji et al., "Protection of Hydroxy Groups By Intramolecular Oxidative Formation of Methoxybenzylidene Acetals with DDQ", Tetrahedron, vol. 23, No. 8, 1982, pp. 889-892.

Omura et al., "Oxidation of Alchols by 'Activated' Dimethyl sulfoxide. A Preparation Steric and Mechanistic Study", Tetrahedron, vol. 34, No. 1978, pp. 1651-1660.

Panek et al., "Oxygenated Allylic Silanes: Useful Homoenolate Equivalents for the Stereoselective C-Glycosidation of Pyranoside Derivative", J. Org. Chem., vol. 54, No. 9, 1989, pp. 2034-2038.

Sharpless et al., "High Stereo- and Regioselectivities in the Transition Metal Catalyzed Epoxidations of Olefinic Alcohols by tert-Butyl Hydroperoxide", J. Am. Chem. Soc., vol. 95, No., 1973, pp. 6136-6137.

Sharpless et al., "Olefin Synthesis. Rate Enhancement of the Elimination of Alkyl Aryl Selenoxides by Electron-Withdrawing Substituents", J. Org. Chem., vol. 40, No. 7, 1975, pp. 947-949.

Sharpless et al., "Metal-Catalyzed, Highly Selective Oxygenations of Olefins and Acetylenes with tert-Butyl Hydroperoxide, Practical Considerations and Mechanisms", Aldrichimica Acta, 12, 1979, pp. 63-74.

Sowden, "α-L-Glucose and L-Mannose", Methods in Carbohydrate Chemistry, vol. 1, 1962, pp. 132-135.

Still et al., "Direct Synthesis of Z-Unsaturated Esters. A Useful Modification of the Horner-Emmons Olefination", Tetrahedron, vol. 24, No. 41, 1983, pp. 4405-4408.

Takai et al., "Reactions of Alkenylchromium Reagents Prepared from Alkenyl Trifluoromethanesulfonates (Triflates) with Chromium(II) Chloride under Nickel Catalysis", J. Am. Chem. Soc., 108, 1986, pp. 6048-6050.

Tanaka et al., "Stereoselective Epoxidations of Acyclic Allylic Alchols by Transition Metal-Hydroperoxide Reagents. Synthesis of dl-$C_{18}$ Cecropia Juvenile Hormone from Farnesol", J. Am. Chem. Soc., vol. 96, No. 14, 1974, pp. 5254-5255.

Tebbe, F. N. et al., "Olefin Homologation with Titanium Methylene Compounds", Am. Chem. Society, vol. 100, No. 11, May 24, 1978, pp. 3611-3613.

Theander, Olof, "1,2:5,6-Di-O-isopropylidene Derivatives of D-Glucohexodialdose and D-Ribo-hexos-3-ulose", Acta Chem. Scand., vol. 18, No. 10, 1964, pp. 2209-2216.

Tomooka, Katsuhiko et al., "Lactols in Stereoselection 3. Highly anti-Cram Selective 1,2-Asymmetric Induction", Tetrahedron Letters, vol. 30, No. 12, 1989, pp. 1563-1566.

Uemura, Daisuke et al., "Norhalichondrin A: An Antitumor Polyether Macrolide from a Marine Sponge", J. Am. Chem. Soc., vol. 107, 1985, pp. 4796-4798.

VanRheenen et al., "An Improved Catalytic $OsO_4$ Oxidation of Olefins to CIS-1,2-Glycols Using Tertiary Amine Oxides as the Oxidant", Tetrahedron, No. 23, 1976, pp. 1973-1976.

Vekemans et al., "Vitamin C and Isovitamin C Derived Chemistry. 3. Chiral Butenolides via Efficient 2,3-Didehydroxylations of L-Gulono-, D-Mannono-, and D-Ribono-1,4-lactones", J. Org. Chem., 53, 1988, pp. 627-633.

Wong, Margaret Y. H. et al., "2-Deoxypentoses. Stereoselective Reduction of Ketene Dithioacetals", J. Am. Chem. Soc., vol. 100, No. 11, 1978, pp. 3548-3553.

Yamaguchi et al., "An Efficient Method for the Alkynylation of Oxiranes Using Alkynl Boranes", Tetrahedron, vol. 24, No. 4, 1983, pp. 391-394.

SYNTHESIS OF HALICHONDRIN B AND NORHALICHONDRIN B

This is a continuation of application Ser. No. 07/849,769, filed Mar. 12, 1992, now abandoned.

BACKGROUND OF THE INVENTION

The invention relates to the synthesis of halichondrin B and norhalichondrin B.

Halichondrins are a class of polyether macrolides isolated originally from the marine sponge *Halichondria okadai* Kadota. Halichondrins, especially halichondrin B and homohalichondrin B, exhibit an extraordinary in vitro and in vivo antitumor activity. However, the very limited supply of halichondrins from natural sources has prevented the full evaluation of thief potential clinical applications.

SUMMARY OF THE INVENTION

The invention features novel chemical compounds that can be used to synthesize halichondrin B and norhalichondrin B, and related derivatives.

One class of novel compounds has the following structure:

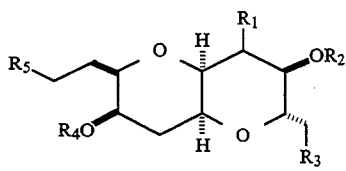

where $R_1$ is —H or an alkyl group having 10 or fewer carbon atoms, $R_2$ is —H or an alcohol blocking group (e.g., a silyl ether, a benzyl ether, or an acyl group); $R_3$ is —CHO, —CH$_2$OB, —CO$_2$D, or

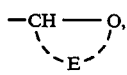

where B is —H or an alcohol blocking group, D is —H or an alkyl group, and E is an alkyl group; $R_4$ is —H or an alcohol blocking group; and $R_5$ is —CHO, —CH$_2$OB, or —CO$_2$D.

Preferred compounds of this class include those having the structure

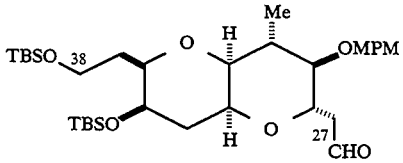

Other preferred compounds of this class include those in which $R_2$ is —H or an alcohol blocking group, and $R_3$ is

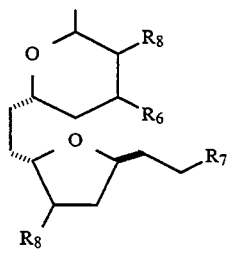

where $R_6$ is —H or an alkyl group having 10 or fewer carbon atoms; $R_7$ is —CHO, —CH$_2$OB, or —CO$_2$D; and each $R_8$, independently, is —H or an alkyl or alkylene group having 5 or fewer carbon atoms. An example is

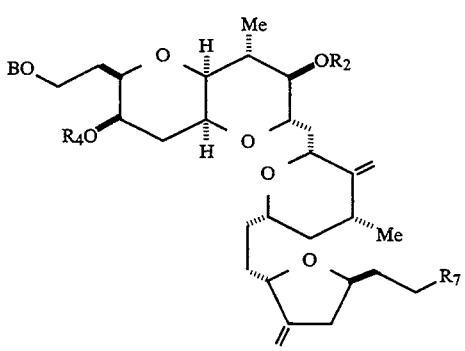

Other preferred compounds of this class include those having the following structure

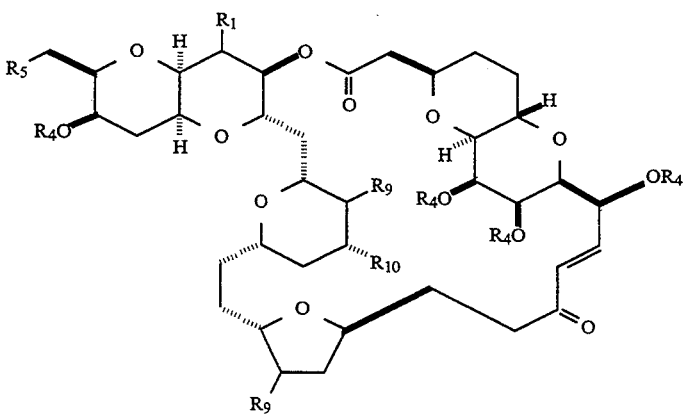

where each $R_9$, independently, is —H or an alkyl group having 5 or fewer carbon atoms; and $R_{10}$ is —H or an alkyl group having 5 or fewer carbon atoms. These preferred compounds include those in which $R_1$ and $R_{10}$ are methyl groups, $R_5$ is —CH$_2$OB, each $R_9$ is a methylene group. These preferred compounds also include those having the following structure:

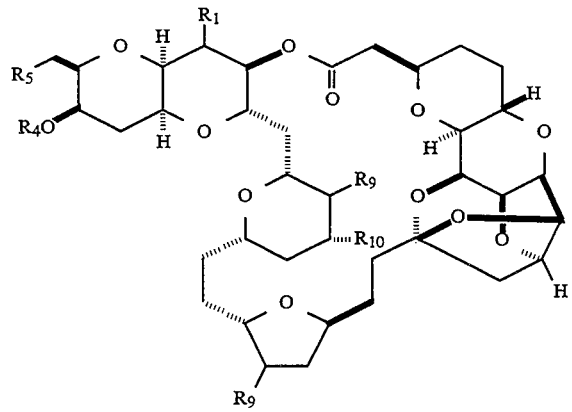

wherein each $R_9$, independently, is —H or an alkyl or alkylene group having 5 or fewer carbon atoms; and $R_{10}$ is —H or an alkyl group having 5 or fewer carbon atoms. A specific example is

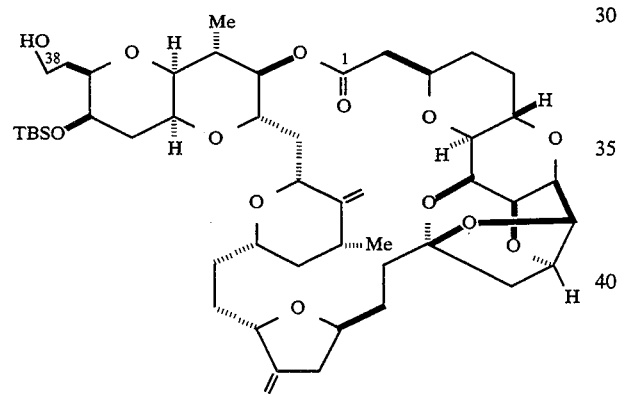

Another class of novel compounds have the following structure:

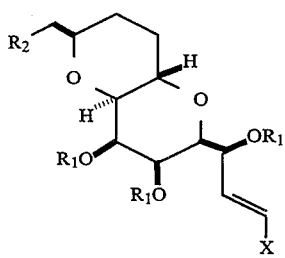

where X is a halide (e.g., I or Br) or an activated alcohol, either cis or trans; each $R_1$, independently, is —H or an alcohol protecting group; and $R_2$ is —CHO, —$CH_2OR_1$, or —$CO_2D$, where D is —H or an alkyl group. An example is

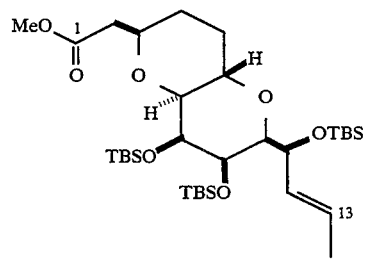

Another class of novel compounds have the following structure:

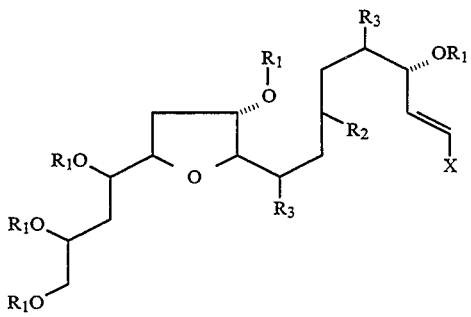

where each $R_1$, independently, is —H or an alcohol protecting group; $R_2$ is a =O or a protected ketone group; each $R_3$, independently, is —H or an alkyl or alkylene group having 5 or fewer carbon atoms; and X is a halide or activated alcohol group, either cis or trans. An example is:

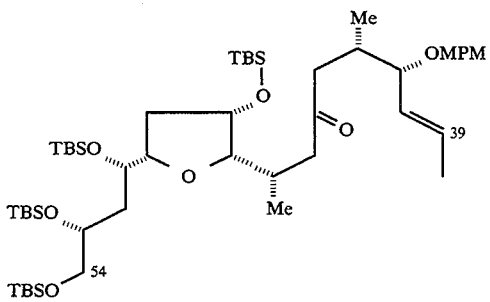

Another class of novel compounds have the following structure:

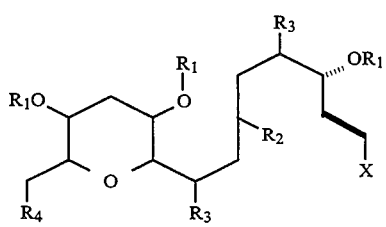

where each $R_1$, independently, is —OH or an alcohol protecting group; $R_2$ is =O or a protected ketone group; $R_3$ is —H or an alkyl or alkylene group having 5 or fewer carbon atoms; $R_4$ is —$CH_2OR_1$, —$CH_2O$, or —$CO_2D$ where D is —H or an alkyl group; and X is a halogen or an activated alcohol group. An example compound is

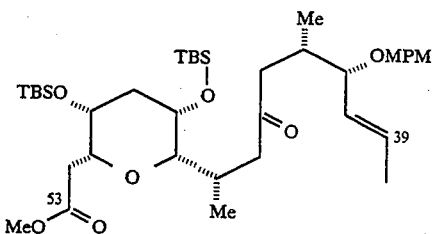
Another class of novel compounds have the following structure:
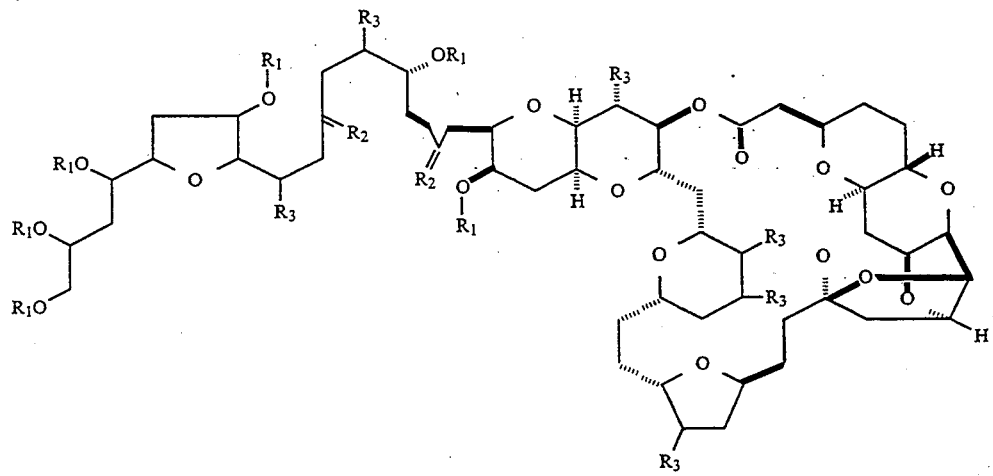
where each $R_1$, independently, is —H or an alcohol protecting group; $R_2$ is O or a protected ketone group; and each $R_3$, independently, is —H or an alkyl or alkylene group having 5 or fewer carbon atoms. An example is
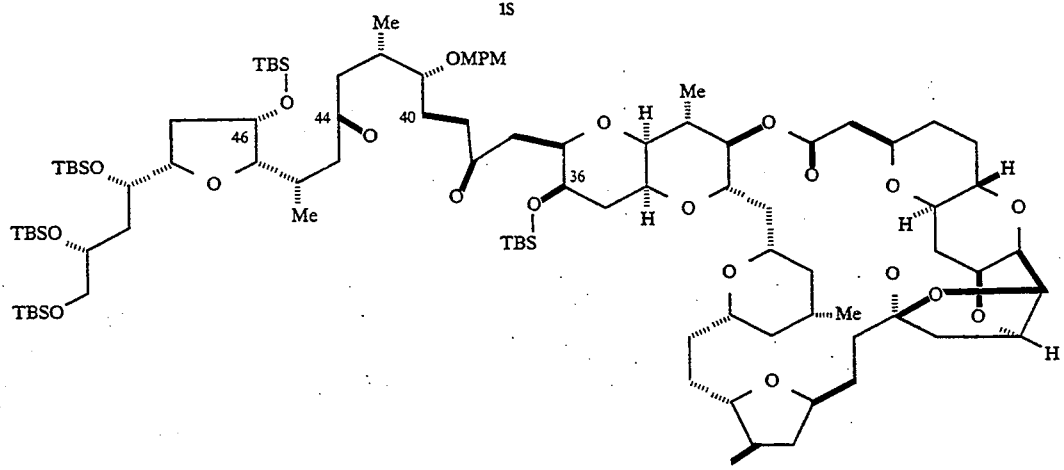
Another class of novel compounds have the following structure:
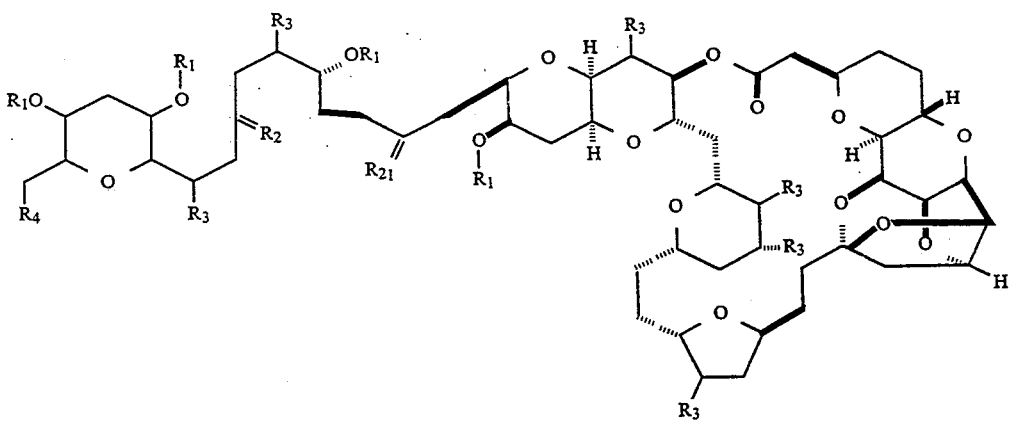

where each $R_1$, independently, is —H or an alcohol protecting group; $R_2$ is O or a protected ketone group; each $R_3$, independently, is —H or an alkyl or alkylene group having 5 or fewer carbon atoms; and $R_4$ is —$CH_2$—$OR_1$, CHO, or $CO_2D$, where D is —H or an alkyl group. An example is

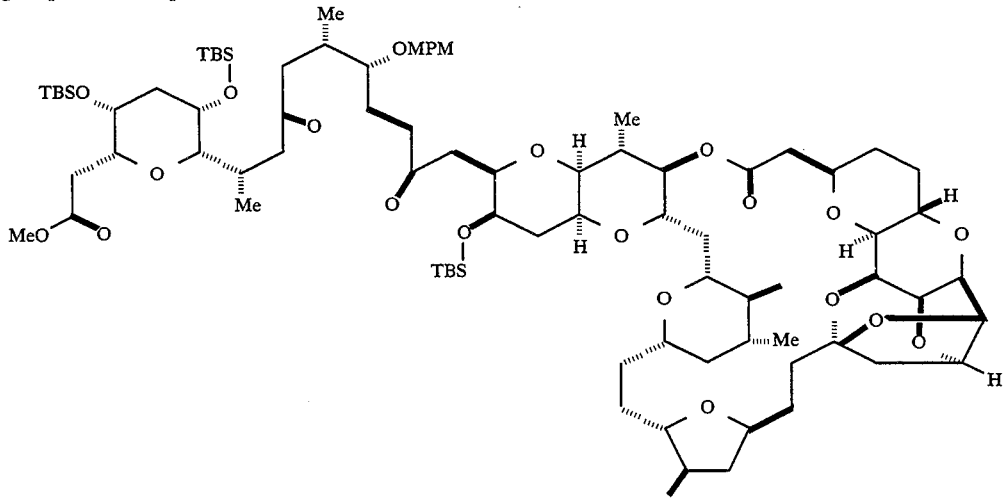

Hydride reduction of the resulting saturated ketone yielded approximately a 1:1 mixture of the two possible diastereomers. As the stereochemistry of diastereomeric alcohols could not be firmly established at this stage, both diastereomers were transformed separately into the corresponding mesylates and used for the next coupling reaction. However, it is important to note that the two diastereomeric alcohols were readily interconvertible via the Mitsunobu reaction.

The invention also features methods of synthesizing the novel compounds and using the compounds in chemical synthesis. One particularly preferred method is the coupling of an aldehyde to a vinyl halide using Ni(II)/Cr(II) mediated reaction conditions. This technique results in the straightforward formation of a carbon-carbon bond between chemically unstable species. Referring to the halichondrin B and nohalichondrin B structure, the Ni(II)/Cr(II) mediated reaction was used to form carbon-carbon bonds between $C_{11}$ and $C_{12}$, $C_{13}$ and $C_{14}$, $C_{26}$ and $C_{27}$, $C_{29}$ and $C_{30}$, and $C_{38}$ and $C_{39}$, with good yields.

The compounds and methods of the invention provide an approach to synthesizing pure halichondrin B and nonhalichondrin B in relatively good yields. Sufficient quantities of the final materials can now be obtained so that the full spectrum of their biological acturties can be studied. The approach allows the novel compounds to be isolated in optically pure form.

Other features and advantages of the invention will be apparent from the Description of the Preferred Embodiment thereof, and from the claims.

DESCRIPTION OF THE PREFERRED EMBODIMENT

Preferred compounds were used to synthesize halichondrin B (1) and morhalichondrin B (2). Schemes 1 and 2 illustrate the general approach used to synthesize these compounds. Persons skilled in the art will recognize that the preferred compounds can be modified, e.g., by using different conventional alcohol blocking groups, and still use the same general scheme to synthesize compounds 1 and 2. They also will recognize that the starting compounds can be modified slightly (e.g., by substituting an ethyl for a methyl group) in order to synthesize analogues of compounds 1 and 2.

Scheme 1 outlines the synthesis of the right half of the halichondrin Bs. The C.21-C.22 bond was accomplished via the preparation of the aldehyde from the primary alcohol 3 by Dess-Martin oxidation, Horner-Emmons reaction under carefully controlled conditions, and the conjugate reduction of the resulting enone by the Stryker reagent, without double-bond isomerization.

Coupling of segment 5 with segment 6 was accomplished by the Ni(II)/Cr(II)-mediated reaction, to yield approximately a 6:1 mixture of the two possible allylic alcohols, which were immediately subjected to base-induced cyclization to furnish the desired tetrahydropyran 7 in 50-60% overall yield, along with a small amount of the undesired diastereomer. The stereochemistry at the C.23 and C.27 positions was established by NOE experiments. The mesylate 5 was found to be quite labile, presumably due to the participation of the C.20 ether oxygen with the mesylate group, yet 5 survived nicely under the Ni(II)/Cr(II)-coupling conditions.

The Ni(II)/Cr(II)-mediated coupling of the C.14 aldehyde derived from 7 with 8, followed by Dess-Martin oxidation, gave the expected trans-enone in 77% overall yield. After removal of the C.30 p-methoxyphenylmethyl (MPM) group and hydrolysis of the C.1 methyl ester, this enone was lactonized under Yamaguchi conditions, to afford the lactone enone 9 in 63% overall yield.

The polycyclic ring system around the C.8-C.14 moiety was, cleanly and effectively, incorporated on treatment of 9 with (n-Bu)$_4$NF (TBAF) then p-TsOH.Py (PPTS) in 64% yield. The $^1$H NMR spectrum showed the product at the TBAF step to be primarily a saturated ketone. The regioselectivity of the Michael reaction was exclusive for the desired five-membered ring-formation, whereas the stereoselectivity was approximately 5~6:1, favoring the desired diastereomer. The undesired Michael adduct, separated from the desired product after PPTS treatment, could be recycled under TBAF conditions. The adjustment of the protecting groups of the polycyclic product furnished the right half 10 of the halichondrin B series.

Coupling of the right half 10 of halichondrin B with the left half 11 was effected by Ni(II)/Cr(II)-mediated reaction to give, after Dess-Martin oxidation, the expected trans-enone in 60% overall yield (Scheme 2).

The enone was successfully transformed into halichondrin B in 3 steps. Although this transformation was carried out without isolation of the product(s) at each step, the $^1$H NMR spectrum indicated the product of the TBAF step to have the partial structure A. This process involved deprotection of the C.48 t-butyldimethylsilyl (TBS) group, hemiketal formation between the C.48 hydroxyl group and the C.44 ketone, and Michael addition of the hemiketal hydroxyl group onto the $\alpha,\beta$-unsaturated ketone. The 5,5-spiroketal formation was then completed by deprotection of the C.41 MPM group, followed by acid treatment. The C.41 hydroxyl group needed to be protected differently from the others to avoid 5,6-spiroketal formation between the C.41 and C.48 hydroxyl groups and the C.44 ketone. Although this 3-step transformation introduced three new chiral centers, its stereoselectivity was very high. The overall yield of the 3-step transformation was 50~60%, and the synthetic halichondrin B was confirmed to be identical with natural halichondrin B (1) on comparison of spectroscopic ($^1$H NMR, MS, IR, $[\alpha]_D^{21}$) and chromatographic data.

The synthesis of norhalichondrin B (2) was carried out in virtually the same way as for halichondrin B except that hydrolysis of the C.53 methyl ester was required as the very last step of the synthesis. The overall yield of the norhalichondrin B synthesis was comparable with that of halichondrin B. On comparison of spectroscopic ($^1$H NMR, MS, IR, $[\alpha]_D^{21}$) and chromatographic data, the synthetic norhalichondrin B was proven to be identical with natural norhalichondrni B (2).

The structure of halichondrin Bs was proposed primarily on the basis of three pieces of evidence: 1. comparison of their spectroscopic data with those of norhalichondrin A, the structure of which was unambiguously established by X-ray analysis, 2. biogenetic considerations of the C.50-and-beyond stereochemistry of halichondrin B, and (3) the absolute stereochemistry of halichondrin Bs was assumed to be the same as that of norhalichondrin A, which was deduced from the exciton chirality of its C.12,C.13-bis-p-bromobenzoates. The present synthetic work has established unambiguously the relative and absolute stereochemistry of halichondrin B and norhalichondrin B.

The more detailed chemical procedures are as follows.

COMPOUND 3

Compound 3 was synthesized according to the following procedure.

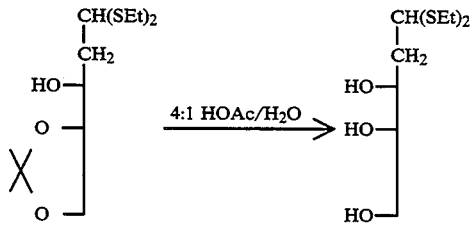

To the monoacetonide (50.4 g, 0.179 mol) was added 250 mL of 4:1 HOAc/H$_2$O and stirred overnight at room temperature. The reaction mixture was concentrated under reduced pressure and purified by flash chromatography (100% EtOAc) to yield the triol (40.6 g, 94% yield).

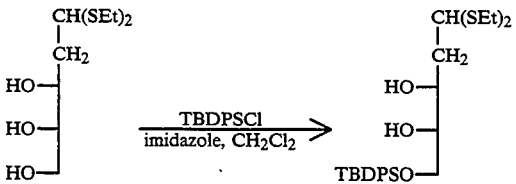

To the triol (40.6 g, 0.169 tool) in CH$_2$Cl$_2$ at 0° C. was added imidazole (50.0 g, 0.734 mol), t-butyldiphenylsilylchloride (51.0 g, 0.186 mol) then stirred for 1 h at 0° C. and 1 h at room temperature. The reaction mixture was diluted with CH$_2$Cl$_2$ and washed with aqueous NaHCO$_3$ (2×). The aqueous layer was back extracted with CH$_2$Cl$_2$ (4×), and the combined organic layers were dried over Na$_2$SO$_4$. Concentration under reduced pressure afforded an oil which was purified by flash chromatography (4:1 Hexanes/EtOAc) to yield the diol (75.7 g, 94% yield) as a colorless oil.

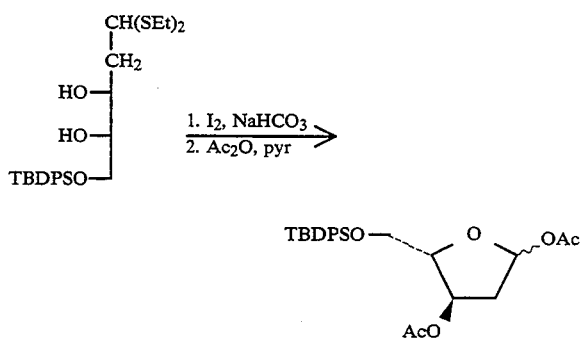

To a stirred solution of thioacetal (75.7 g, 0.158 mol) and NaHCO$_3$ (79.7 g, 0.949 mol) in acetone (550 mL) and H$_2$O (90 mL) at 0° C. was added iodine (120.4 g, 0.474 mol). After 0.5 h TLC (1:1 hexanes/EtOAc) indicated complete absence of the starting thioacetal. The reaction mixture was quenched by addition of aqueous Na$_2$S$_2$O$_3$ and the acetone was removed under reduced pressure. The mixture was extracted with EtOAc (4×) and the combined organic layers were washed with brine (1×), H$_2$O (1×) then dried over Na$_2$SO$_4$ and concentrated under reduced pressure to afford the furanose as a yellow oil. To the crude furanose was added pyridine (75 mL), Ac$_2$O (80.5 g, 0.789 mol, 74 mL) and DMAP (1.9 g, 0.0157 mol) at room temperature. The reaction was stirred overnight, concentrated under reduced pressure then purified by flash chromatography (3:1 hexanes/EtOAc) to afford the diacetate (67.7 g, 94% yield) and an oil.

IR (film) 606 cm$^{-1}$, 702, 997, 1113, 1230, 1742, 2932, 2958, 3072.

$^1$H NMR (CDCl$_3$): δ 1.91 (OAc, s), 2.06 (OAc, s), 2.08 (OAc, s), 2.09 (OAc, s), 2.18 (0.5H, m), 2.27 (0.5H, m), 2.49 (0.5H, m), 2.56 (0.5H, m), 3.78 (1.5H, m), 3.86 (0.5H, dd), 4.18 (0.5H, m), 4.31 (0.5H, m), 5.37 (0.5H, dd), 5.42 (0.5H, m), 6.38 (0.5H, dd), 6.42 (0.5H, d), 7.39 (6H, m), 7.69 (4H, m).

HRMS (FAB) calcd for C$_{25}$H$_{32}$O$_6$Si+Na 479.1866, found 479.1891.

$[\alpha]_D$ −18.6° (c 1.81, MeOH).

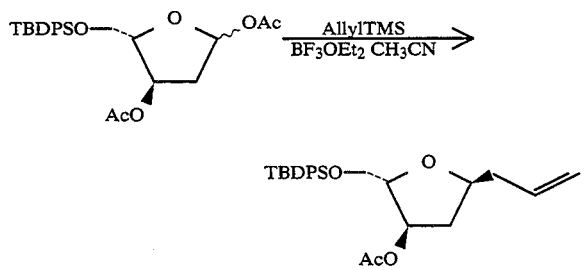

To an ice cold solution of the diacetate (67.7 g, 0.148 mol) and allyltrimethylsilane (50.8 g, 0.444 mol, 70.6 mL) in CH₃CN was added BF₃·OEt₂ (21.0 g, 0.148 mol, 18.2 mL) dropwise over 10 min. The reaction mixture was stirred for an additional 15 rain then quenched with dilute aqueous NaHCO₃. The mixture was extracted with EtOAc (3×) and the combined organic layers dried over Na₂SO₄. Concentration under reduced pressure and purification by flash chromatography (5:1 hexanes/EtOAc) afforded an oil (58.9 g, 90% yield).

IR (film) 702 cm⁻¹, 1113, 1247, 1759, 2867, 3079.

¹H NMR (CDCl₃, 500 MHz): δ 1.05 (9H, s, t-Su), 1.74 (1H, m), 2.06 (3H, s, O-CH₃), CH₃), 2.31 (1H, m), 2.44 (1H, m), 2.49 (1H, m), 3.71 (1H, dd, J=4.5, 10.9 Hz), 3.76 (1H, dd, J=3.7, 10.9 Hz), 4.09 (1H, m), 4.24 (1H, p, J=6.6 Hz), 5.09 (2H, m), 5.36 (1H, m, CH—OAc), 5.81 (1H, m), 7.39 (6H, m), 7.67 (4H, m).

HRMS (FAB) calcd for C₂₆H₃₄O₄Si (M+Na)+ 461.2124, found 461.2138.

[α]_D −16.9° (c 1.25, MeOH).

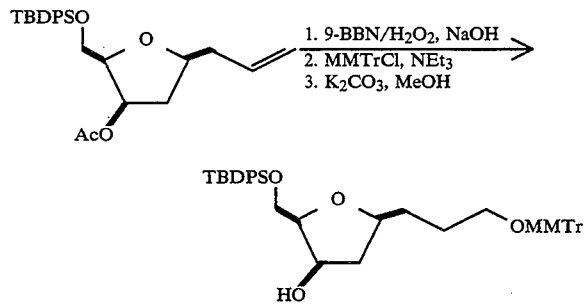

To a solution of olefin (24.1 g, 55 mmol) in THF (400 mL) at 0° C. was added 0.5M 9-BBN in THF (142 mL, 71.5 mmol). The reaction mixture was allowed to warm to room temperature and stir overnight. The solution was cooled to 0° C. and 10% NaOH (90 mL) was added followed by 30% H₂O₂ (90 mL). After stirring for 2 h, the reaction was quenched by addition of aqueous NH₄Cl and extracted with EtOAc (3×600 mL). The combined organic layers were washed with aqueous K₂CO₃ (2×), dried over NaSO₄ and concentrated under reduced pressure.

Note: Some hydrolysis of acetate was observed. Therefore the crude mixture was used for selective funtionalization of the primary alcohol without purification.

To a solution of the crude alcohol in CH₂Cl₂ (300 mL) was added Et₃N (54 mL, 385 mmol) followed p-anisylchlorodiphenylmethane (18.7 g, 60.5 mmol) at 0° C. The reaction was stirred for 8 h then quenched with aqueous NaHCO₃ and extraced with CH₂Cl₂ (2×100 mL). The combined organic layers were dried over Na₂SO₄, concentrated under reduced pressure.

Powdered K₂CO₃ (4 g) was added portionwise to a solution of the crude acetate in THF (10 mL) and MeOH (300 mL). The reaction was stiffed for 2.5 h at room temperature then filtered through Celite and purified by flash chromatography with 20% EtOAc in hexanes to afford the desired product (26.7 g, 70.8% yield over 3 steps).

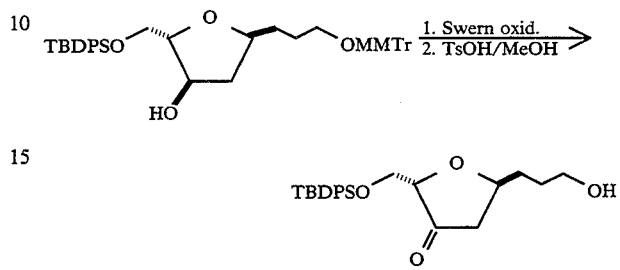

To a solution of oxalyl chloride (1.33 mL, 15.3 mmol) in CH₂Cl₂ (150 mL) was added DMSO (2.16 mL, 30.2 mmol) dropwise over 3 rain at −78° C. After stirring for 10 rain, a solution of alcohol in CH₂Cl₂ (10 mL) was added over 5 min. The empty flask was washed with additional CH₂Cl₂ (3 mL) and the solution was added to the reaction mixture. After stirring for 1 h, NEt₃ (8.55 mL, 60.4 mmol) was added to the reaction mixture. The reaction mixture was stirred for additional 15 rain and warmed to room temperature over 45 min. The reaction mixture was quenched with saturated NH₄Cl and the organic layer was separated. The organic layer was washed with water, brine, dried over Na₂SO₄, and concentrated. The residue was purified by column chromatography with 20% EtOAc in hexanes to give the ketone (2.37 g, 97% yield).

To a solution of MMTr-ketone (9.3 g, 13.5 mmol) in CH₂Cl₂ (200 mL) and MeOH (50 mL) was added TsOH (1 g) at room temperature. After stirring for 2 h, solid NaHCO₃ was added to the reaction mixture to neutralize TsOH. After stirring for 1 h, the reaction mixture was filtered, concentrated, and purified by column chromatography with 33% EtOAc in hexanes to afford the keto-alcohol (5.4 g, 96.6% yield).

IR (film) 703 cm⁻¹, 743, 823, 1077, 1113, 1428, 1759, 2893, 2930, 3071, 3438.

¹NMR (CDCl₃): δ 1.01 (9H, s), 1.57 (1H, br s), 1.75 (2H, m), 1.80 (2H, m), 2.28 (1H, dd, J=8.3, 17.9 Hz), 2.66 (1H, dd, J=6.5, 17.9 Hz), 3.73 (2H, m), 3.87 (1H, dd, J=2.2, 11.1 Hz), 3.97 (1H, dd, J=2.4, 11.1 Hz), 4.03 (1H, br s), 4.73 (1H, m), 7.43 (6H, m), 7.68 (2H, m), 7.70 (2H, m).

HRMS (FAB) calcd for C₂₄H₃₂O₄Si+Na 435.1968, found 435.1954.

[α]_D −19.2° (c 1.2, MeOH).

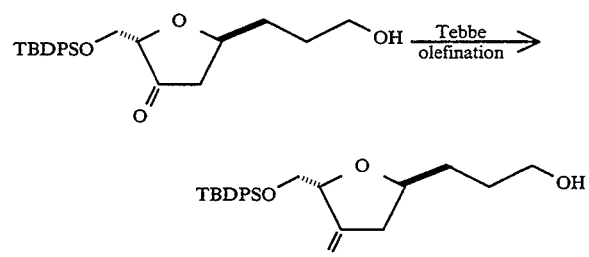

To a well-stirred solution of the keto alcohol (747 mg, 1.81 mmol) in a 3:1:1 mixture of toluene:THF:pyridine (11 mL) at 0° C. was added dropwise a freshly prepared solution of Tebbe reagent [prepared in situ according to the procedure of Grubbs: Grubbs, R. M.; Cannazzo, L. F. *J. Org. Chem.*, 50, 2386 (1985)] (8.3 mL, about 3 eq) over 15 min. TLC (50% ethyl acetate/hexanes) indicated complete loss of starting material in about 0.5 h. The reaction was quenched by cautious addition of 0.1N NaOH (10 mL) The mixture was diluted with ether and the solution vigorously stirred until the organic layer was light yellow. The layers were separated and the aqueous phase extracted with ether. The combined organic fractions were exhaustively washed with water to remove pyridine, then with brine. The organic layers were dried over sodium sulfate, and removed in vacuo. The residue was purified by flash chromatography(40% ethyl acetate/hexanes) to afford the exocyclic olefin(647 mg, 87% yield).

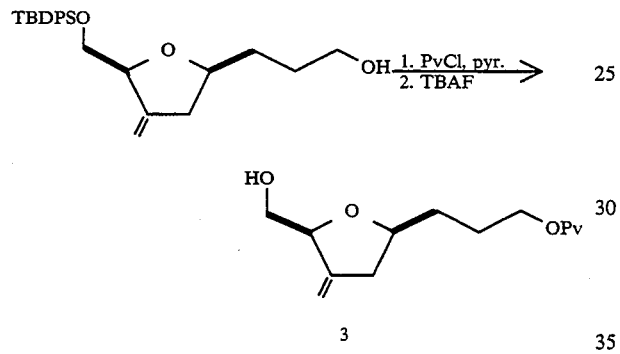

To a stirred solution of an alcohol (5.24 g, 12.8 mmol) in CH$_2$Cl$_2$ (90 mL) at room temperature was added pyridine (6.2 mL, 76.6 mmol), DMAP (50 mg), and pivaloyl chloride (8.3 mL, 67.7 mmol). After stirring for 1 h, the reaction mixture was quenched with saturated NHCl, diluted with CH$_2$Cl$_2$, and extracted. The combined organic layers were washed with 10% HCl, water, saturated NaHCO$_3$, brine, and dried over Na$_2$SO$_4$. The solvents were concentrated under reduced pressure.

To a solution of crude pivaloate in THF (140 mL) was added 1M TBAF in THF (20 mL, 20 mmol) dropwise at room temperature. After stirring for 1.1 h, the reaction mixture was concentrated under reduced pressure, and the residue was purified by column chromatography with 15% EtOAc in hexanes to afford the desired product (2.98 g, 91% yield over 2 steps).

IR (film) 1157 cm$^{-1}$, 1284, 1480, 1727, 2872, 2959, 3078, 3453.

$^1$H NMR (CDCl$_3$): δ 1.19 (9H, s), 1.55 (1H, m), 1.67 (2H, m), 1.77 (1H, m), 1.93 (1H, m), 2.29 (1H, dd), 2.70 (1H, dd), 3.61 (2H, m), 4.09 (3H, t, J=6.3 Hz), 4.50 (1H, br), 4.92 (1H, m), 5.08 (1H, m).

HRMS (CI) calcd for C$_{14}$H$_{24}$O$_4$+H (M+H)$^+$ 257.1753, found (M+H)$^+$ 257.1744.

[α]$_D$ −27.2° (c 1.1, MeOH).

COMPOUND 4

Compound 4 was synthesized according to the following procedure.

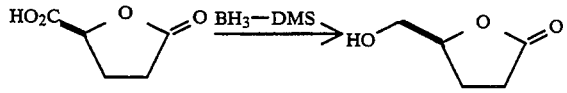

To a solution of the carboxylic acid (42 g, 0.32 mol) in dry THF (300 mL,) was added at room temperature BH$_3$-DMS (39 mL, neat, 0.39 mol) at such a rate as to maintain gentle reflux.. After an additional 3 h, the mixture was cooled to 0° C., and cautiously quenched with excess methanol (500 mL). The solvents were removed by distillation at atmospheric pressure, and the residue purified by distillation in vacuo to afford 34.3 g of pure alcohol.

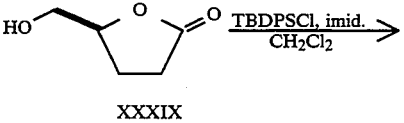

XXXIX

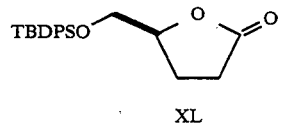

XL

Lactone XL:

To a stirred solution of the lactone XXXIX (12.5 g, 108 mmol) and imidazole (15.6 g, 229 mmol) in CH$_2$Cl$_2$ (300 mL) at 0° C. was added tertbutyldiphenylsilyl chloride (29.0 mL, 112 mmol). The mixture was allowed to stir at room temperature overnight. The mixture was diluted with CH$_2$Cl$_2$, then washed with saturated NaHCO$_3$, water, brine, dried (Na$_2$SO$_4$), and concentrated under reduced pressure. The mixture was purified by crystallization from hexane, yielding the silyl ether X L (30.05 g in the first crop, and an additional 5.40 g in the second crop; 93% combined yield, mp 84° C.).

IR (film): 3072 cm$^{-1}$, 3049, 2998, 2931, 2893, 2858, 1777, 1590, 1473, 1461, 1427, 1391, 1346, 1174, 1113, 1084, 1032, 995, 941, 858, 822, 741, 703.

$^1$NMR (CDCl$_3$): δ1.07 (9H, s), 2.19-2.34 (2H, m), 2.52 (1H, m), 2.69 (1H, m), 3.70 (1H, dd, J=3.3, 11.3 Hz), 3.90 (1H, dd, J=3.2, 11.3 Hz), 4.61 (1H, m), 7.30-7.50 (6H, m), 7.60-7.80 (4H, m).

$^{13}$C NMR (CDCl$_3$): δ 19.22, 23.65, 26.78, 28.55, 65.45, 79.89, 127.70, 129.77, 135.38, 135.47, 177.37.

[α]$_D$: +24.9° (C 5.91, CHCl$_3$).

Analysis calcl for C$_{21}$H$_{26}$O$_3$Si: C 71.15, H 7.39; found: C 70.91, H 7.42.

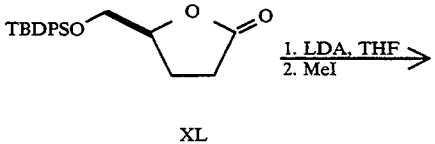

XL

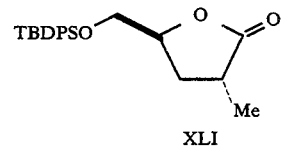

XLI

Lactone XLI:

To a stirred solution of diisopropylamine (3.88 mL, 27.69 mmol) in THF (10 mL) at −78° C. was added a 2.35M solution of n-butyllithium in hexane (11.8 mL, 27.69 mmol). After stirring the resulting mixture for 20 min, a solution of the lactone XL (9.347 g, 26.4 mmol) in THF (20 mL) was slowly added via cannula. After stirring the mixture 25 rain at −78° C., methyl iodide (4.85 mL, 77.9 mmol) was added. After 35 rain, the reaction was quenched by the careful addition of saturated NH4Cl. The mixture was allowed to warm to 0° C., and then diluted with ether. The layers were separated, and the aqueous layer was reextracted with ether. The combined organic layers were washed with water, brine, dried over Na2SO4), and concentrated under reduced pressure. Crystallization with hexane yielded the major methylated product XLI (top 84° C., 7.3 g, 75% yield). The mother liquor contained 1.4 g of a mixture of the two methylated compounds.

IR (film): 3072 cm$^{-1}$, 3051, 2958, 2932, 2859, 1774, 1473, 1462, 1428, 1362, 1349, 1202, 1173, 1113, 1067, 1022, 998, 954, 935, 822, 742, 727, 702, 623.

$^1$H NMR (CDCl3): δ 1.06 (9H, s), 1.27 (3H, d, J=7.1 Hz), 1.98 (1H, m), 2.47 (1H, m), 2.86 (1H, m), 3.67 (1H, dd, J=3.3, 11.3 Hz), 3.88 (1H, dd, J=3.5, 11.3 Hz), 4.56 (1H, m), 7.30–7.50 (6H, m), 7.70–7.80 (4H, m).

$^{13}$C NMR (CDCl3): δ 16.47, 19.25, 26.84, 32.27, 34.24, 65.57, 77.49, 127.74, 129.81, 132.49, 132.87, 135.42, 135.51, 179.82.

MS (FAB): 369 amu (M$^+$+H, rel. intensity 2%), 313 (6), 312 (18), 311 (74), (7), 292 (24), 291 (100), 233 (17), 199 (29), 197 (36), 163 (27), 135 (86).

[α]$_D$+1.3° (c 1.43, CHCl3).

Analysis calcd for C22H28O3Si.¼H2O: C 71.70, H 7.66; found: C 70.84, H 7.54.

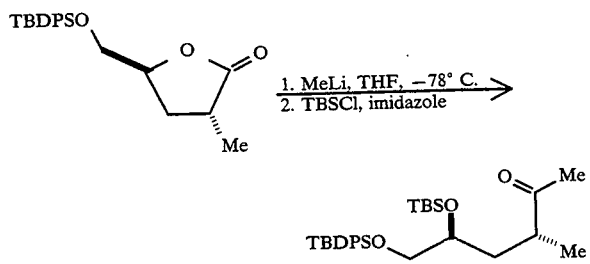

To a solution of lactone (46.2 g, 0.125 mol) in THF (400 mL) was added 1.4M MeLi in ether (89.5 mL, 0.125 mol) over 10 rain at −78° C. After stirring for 10 rain, the reaction mixture was poured into saturated NH4Cl solution (300 mL) and extracted with EtOAc (3×300 mL). The combined organic layers were washed with brine (200 mL), dried over Na2SO4, and concentrated under reduced pressure.

To a solution of crude hemiketal in CH2Cl2 (600 mL) was added imidazole (22.2 g, 0.150 mol), followed by TBDMSCl (22.2 g, 0.325 mol). The resulting reaction mixture was stirred for 36 h at room temperature. The reaction mixture was washed with saturated NaHCO3, water, and brine. The organic layer dried over Na2SO4, and concentrated under reduced pressure. The residue was purified by column chromatography with 10% EtOAc in hexanes to afford 51.3 g of disilyl ether (82.4% yield) as a colorless oil.

IR (film) 1112 cm$^{-1}$, 1254, 1462, 1473, 1716, 2886, 2930, 2957.

$^1$H NMR (CDCl3): δ 1.20 (3H, s), −0.50 (3H, s), 0.81 (9H, s), 1.06 (9H, s), 1.11 (3H, d, J=7.1 Hz), 1.47 (1H, m), 2.12 (3H, s), 2.15 (1H, m), 2.71 (1m), 3.46 (1H, dd, J=7.2, 10.1 Hz), 3.57 (1H, dd, J=4.6, 10.1 Hz), 3.70 (1H, m), 7.42 (6H, m), 7.66 (4H, m).

HRMS (FAB) calcd C29H46O3Si2+Na 521.2853, found 521.2885.

[α]$_D$−13.0° (c 1.15, MeOH).

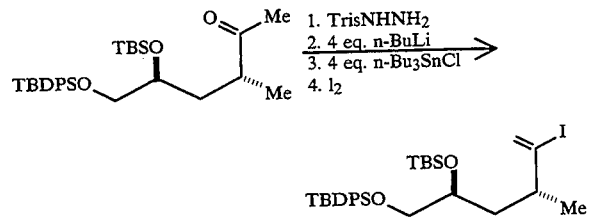

To a solution of ketone (7.1 g, 14.26 mmol) in THF (16 mL) was added TrisNHNH2 (5.1 g, 1.2 eq) followed by 1 drop of conc. HCl. After stirring for 4 h, the reaction mixture was directly concentrated, further dried by azeotropic removal of water with benzene (×2) and then under high vacuum. The crude hydrazone was dissolved in TMEDA/pentane (30/120 mL) and cooled to −78° C. and the reaction mixture was treated with 2.06M n-BuLi (27.5 mL, 4 eq) for 30 min. The reaction mixture was then warmed to 0° C. and held under ice bath for 10 rain (red to yellow).

The vinyl lithium solution was cooled to −78° C. and n-Bu3SnCl (15 mL, 3.9 eq) was added very slowly. When the stirring was hard, temperature was adjusted to −15° C. and the reaction mixture was stirred for 1 h at the same temperature and for 1 h at 0° C. (almost colorless solution). The reaction mixture was diluted with ether (100 mL) and washed with saturated NH4Cl, water, and brine. The organic layer was dried over Na2SO4, concentrated, and purified by column chromatography with hexanes to 10% toluene in hexanes to afford the vinyl tin compound.

The vinyl tin compound was dissolved in CH2Cl2 (100 mL) and titrated with a solution of iodine until it showed purple color at 0° C. The reaction mixture was washed with NaHSO3 solution, water, and brine. The organic layer was concentrated and the residue was purified by column chromatography with 10% toluene in hexanes to afford 6.76 g of vinyl iodide compound with 78% yield.

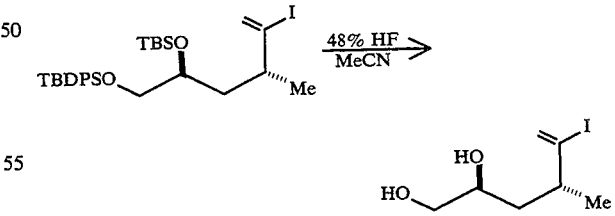

To a solution of silyl ether in MeCN (90 mL) and THF (10 mL) was added 48% HF (1.2 mL, 3 eq). After stirring for 10 h, solid NaHCO3 (5 g) and EtOAc (300 mL) was added and stirred until bubbling was stopped. Filtered, concentrated, and purified by column chromatography with gradient elution of 10 % EtOAc in CHCl3 to EtOAc to afford 1.79 g of diol (70% yield).

*Because of volatility of diol, this yield was low. One does not need to dry diol rigorously to get better yield, since the next step will be done in aqueous media.

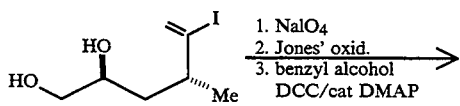

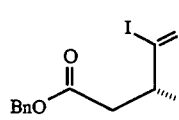

To a solution of diol (1.79 g, 7.02 mmol) in THF (15 mL) and water (7 H mL) was added NaIO4 at room temperature. After stirring for 1 h, the reaction mixture was diluted with water until it formed a clear solution, followed by extraction with ether (2×20 mL). The organic layer was washed with NaHSO3 solution to remove excess oxidant. The organic layer was concentrated under reduced pressure without drying. The crude aldehyde was diluted with acetone (50 mL). The resulting solution was cooled to 0° C. and treated with Jones reagent. After the reaction was complete, the excess Jones reagent was quenched with isopropanol. The reaction mixture was filtered through Celite, concentrated, diluted with ether, and washed with water and brine. The organic layer was dried over MgSO4, concentrated, and further dried by azeotropic removal of water with benzene (×2).

To a solution of crude acid in CH2Cl2 (20 mL) was added benzyl alcohol (1 mL, 1.4 eq) followed by DCC (1.74 g, 1.2 eq) with a catalytic amount of DMAP (5%) at room temperature. After stirring for 12 h, extra DCC (0.5 g, 0.34 eq) along with benzyl alcohol (0.5 mL, 0.7 eq) was added to the reaction mixture. After 6 h, the reaction mixture was concentrated, diluted with ether (5 mL), and filtered through Celite. The filtrate was concentrated and purified by column chromatography with 9% EtOAc in hexanes to afford the benzyl eter (2.16 g, 93.5% yield).

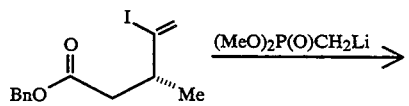

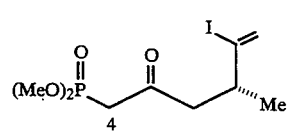

To a solution of phosphonate (3.4 g, 27.2 mmol) in THF (16 mL) was added 2.13M n-BuLi at −78.° C. After stirring for 1 h, the benzoate (2.5 g, 7.58 mmol) in THF (4 mL) was added dropwise. After 20 min, the reaction mixture was quenched with saturated NH4Cl and extracted with EtOAc (3×20 mL). After drying over Na2SO4 and concentration, the residue was purified by column chromatography with EtOAc in hexanes (50% to 80%) afford 1.90 g of ketophophonate (78.4% yield) along with 249 mg of recovered benzoate (10% yield). Yield based on recovered starting was 87%.

IR (film) 1028 cm−1, 1262, 1613, 1715, 2959.

1H NMR (CDCl3): δ1.03 (3H, d, J=6.1 Hz), 2.57 (2H, m), 2.81 (1H, m), 3.08 (2H, m), 3.78 (3H, s, —OMe), 3.80 (3H, s, —OMe), 5.72 (1H, d, J=1.4 Hz), 6.19 (1H, s).

HRMS (FAB) calcd for C9H16O4PI+Na 368.9729, found 368.9744.

[α]D −2.4° (c 4.9, MeOH).

COMPOUND 5

Compound 5 was synthesized according to the following procedure.

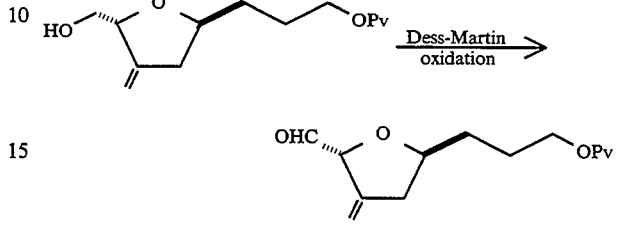

To a solution of the alcohol (180 mg, 0.706 mmol) in dichloromethane (12 mL) at room temperature was added Dess-Martin reagent (449 mg, 1.5 eq) along with 3A molecular sieves (2 g). After stirring for 25 min, the reaction mixture was diluted with ether (60 mL) and filtered through Celite. The filtrate was washed with 6 eq of sodium dithionate solution in saturated NaHCO3 solution (20 mL), saturated NaHCO3, water and brine. The organic layer was dried concentrated and further dried by azeotrope. The crude aldehyde was used in the next step without further purification.

To a solution of the ketophosphonate (333 mg, 1.06 mmol) in dry THF (4 mL) at 0° C. was added NaH (38 mg, 0.95 mmol). After stirring for 0.5 h, the aldehyde in THF (2 mL) was added dropwise over 5 min. After stirring for an additional 0.5 h the reaction was quenched with saturated ammonium chloride, and extracted with ethyl acetate. The organic layers were dried over sodium sulfate, and concentrated in vacuo. Purification via flash chromatography (20% ethyl acetate/hexanes) afforded the pure enone (295 mg, 88% yield).

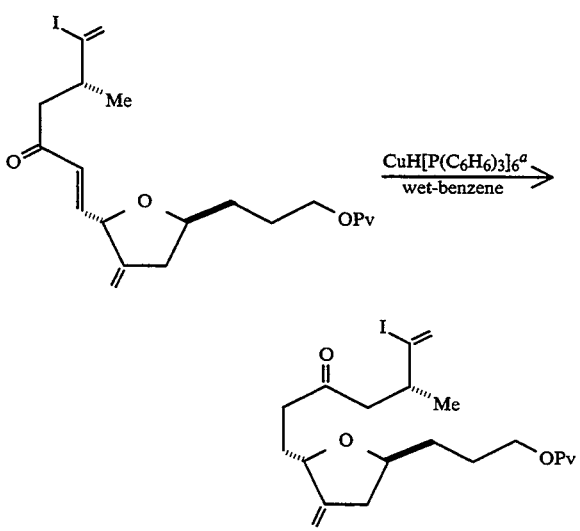

To a solution of enone (650 mg, 1.37 mmol) in 65 mL of degassed benzene and 0.4 mL (16 eq) of degassed water was added [CuH(Ph3P)]6 (806 mg, 1.8 eq). The red reaction mixture was stirred for 3 h under argon and then the reaction vessel was opened to air to decompose excess reagent. After 1 h, the black reaction mixture was filtered through Celite. The filtrate was concentrated under reduced pressure and purified by column chromatography with 6% ethyl acetate in hexanes to afford the ketone in (605 mg, 93% yield).

IR (film) 898 cm$^{-1}$, 1174, 1336, 1726, 2934, 2962.

$^1$H NMR (CDCl$_3$): δ 1.02 (3H, d, J=6.5 Hz, CH$_3$), 1.58 (9H, s, —OPv), 1.50 (1H, m), 1.61 (2H, m), 1.72 (2H, m), 1.87 (1H, m), 2.25 (1H, m), 2.33 (1H, dd, J=6.9, 16.3 Hz), 2.54 (3H, m), 2.67 (2H, m), 3.99 (1H, m), 4.06 (2H, m), 4.35 (1H, m), 4.87 (1H, d, J=2.0 Hz), 5.00 (1H, d, J=2.1 Hz), 5.70 (1H, d, J=1.7 Hz), 6.17 (1H, d, J=1.3 Hz).

HRMS (FAB) calcd for C$_{21}$H$_{33}$O$_4$I+Na 499.1323, found 499.1334.

[α]$_D$ −37.0° (c 1.01, MeOH).

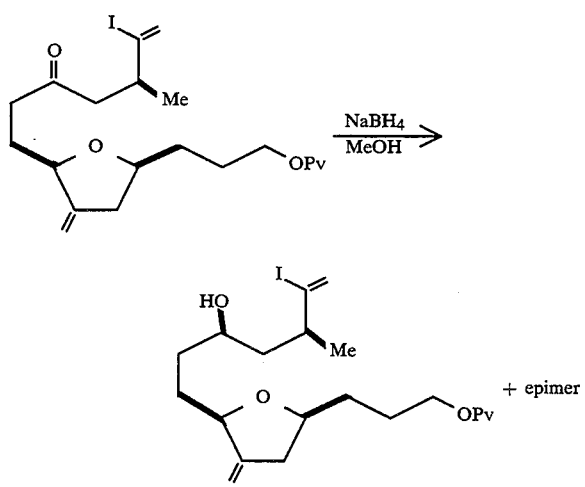

To a solution of ketone (1.26 g, 2.65 mmol) in MeOH (20 mL) at 0 °C. was added NaBH$_4$ (130 mg, 3.38 mmol). After stirring for 20 min at the same temperature, the reaction mixture was quenched with saturated NH$_4$Cl and extracted with EtOAc (3×20 mL). The combined organic layers were dried over Na$_2$SO$_4$, concentrated, and purified by column chromatography with 8/2/1 (hexanes/EtOAc/CHCl$_3$) to afford a desired higher R$_f$ alcohol (877 mg, 69.6% yield), an undesired lower R$_f$ alcohol (372 mg, 29.5% yield), and a mixed fraction (56 mg, 4.4% yield).

IR (film) 1157 cm$^{-1}$, 1285, 1728, 2930, 2959, 3440.

$^1$H NMR (CDCl$_3$): δ 0.98 (3H, d, J=6.5 Hz), 1.19 (9H, s, —OPv), 1.25–1.70 (11H, m), 2.08 (1H, m), 2.27 (1H, m), 2.47 (1H, br s), 2.70(1H, m), 3.58 (1H, m), 4.07 (2H, m), 4.39 (1H, m), 4.86 (1H, m), 5.00 (1H, m), 5.75 (1H, d, J=1.3 Hz), 6.24 (1H, br s).

HRMS (FAB) calcd for C$_{21}$H$_{35}$O$_4$I+Na 501.1480, found 501.1485.

[α]$_D$ −82.2° (c 0.9, MeOH).

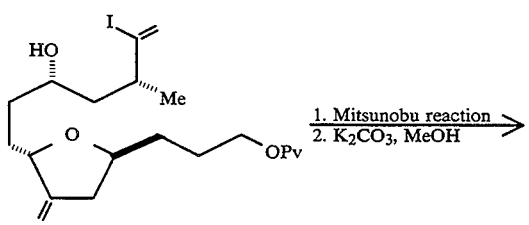

-continued

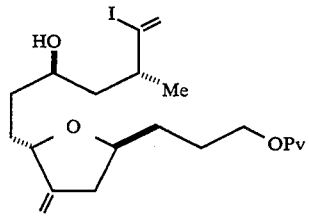

To a solution of alcohol (364 mg, 0.76 mmol) in ether (16 mL) were added Ph$_3$P (478 mg, 2.4 eq), and p-nitrobenzoic acid (280 mg, 2.4 eq), followed by diethyl azodicarboxylate (250 μL, 2.4 eq). The reaction mixture was stirred for 1 h and hexanes (20 mL) was added. The reaction mixture was filtered through SiO$_2$ eluting with 30% ethyl acetate in hexanes to remove excess reagents. The filtrate was concentrated and the residue was dissolved in benzene. The suspension was applied to a silica gel column through a glass wool plug to remove insolubles. Purification by column chromatography with 10% ethyl acetate in hexanes gave the benzoate (422 mg, 88.9% yield).

The benzoate was dissolved in MeOH (20 mL) with K$_2$CO$_3$ (2 mg). The reaction mixture was stirred until the starting material was completely consumed. HOAc (1 or 2 drops) was added to neutralize or acidify the reaction mixture. After stirring for 10 rain, the reaction mixture was concentrated and purified by column chromatography with 13% EtOAc in hexanes to give the inverted alcohol (319 mg, 99% yield).

IR (film) 1157 cm$^{-1}$, 1285, 1728, 2930, 2959, 3440.

$^1$H NMR (CDCl$_3$): δ 0.98 (3H, d, J=6.5 Hz), 1.19 (9H, s, —OPv), 1.25–1.70 (11H, m), 2.08 (1H, m), 2.27 (1H, m), 2.47 (1H, br s), 2.70(1H, m), 3.58 (1H, m), 4.07 (2H, m), 4.39 (1H, m), 4.86 (1H, m), 5.00 (1H, m), 5.75 (1H, d, J=1.3 Hz), 6.24 (1H, br s).

HRMS (FAB) calcd for C$_{21}$H$_{35}$O$_4$I+Na 501.1480, found 501.1485.

[α]$_D$ −82.2° (c 0.9, MeOH).

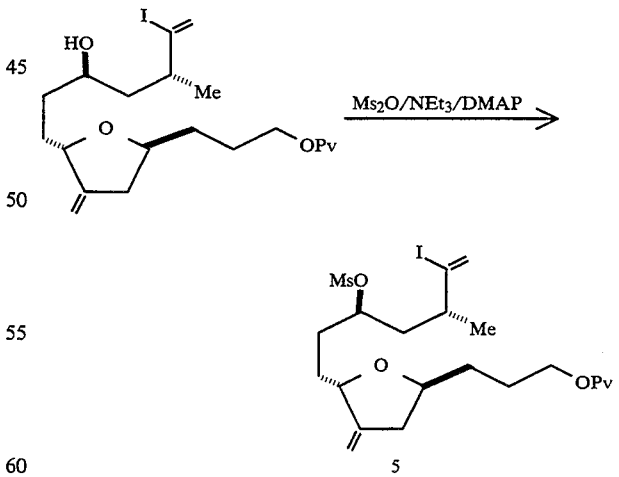

To a solution of alcohol (14.6 mg, 0.03 mmol) in CH$_2$Cl$_2$ (1 mL) was added catalytic DMAP, NEt$_3$ (7.7 μL, 1.8 eq), and Ms$_2$O (7.5 mg, 1.5 eq). After 30 min, the reaction mixture was quenched with saturated NaHCO$_3$ solution and extracted with ethyl acetate (2×5 mL). The combined organic layers were washed with brine, dried, and concentrated. The crude residue was briefly filtered through SiO2 plug with 25% ethyl acetate in hexanes to give 16.3 mg of the mesylate in 96% yield. (SKY 1-167)

IR (film) 898 cm$^{-1}$, 1173, 1337, 1355, 1725, 2871, 2934, 2962.

$^1$H NMR (CDCl3): δ1.01 (3H, d, J=6.5 Hz), 1.19 (9H, s),1.45-1.80(9H, m), 1.84 (1H, m), 1.90 (1H, m), 2.27 (1H, dd, J=5.7, 15.3 Hz), 2.68 (1H, dd, J=6.4, 15.3 Hz), 3.02 (1H, s). 4.05 (1H, m), 4.07 (1H, m), 4.37 (1H, m), 4.69 (1H, m), 4.88 (1H, s), 5.01 (1H, s), 5.85 (1H, s), 6.36 (1H, s).

COMPOUND 6

Compound 6 was synthesized according to the following procedure.

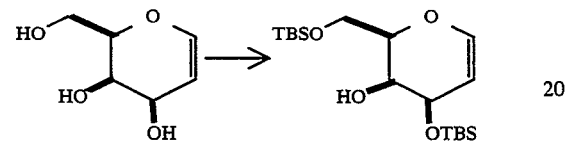

3,5-Di-O-tert-butyldimethylsily-D-galactal[1]

[1] after: Kinzy, W.; Schmidt, R. R. *Tetrahedron Letters* 1987, 28, 1981-1984. and Horton, D.; Priebe, W.; Varela, O. *Carbohydrate Research* 1985, 144, 325-330.

To a stirred solution of D-galactal[2] (18.188 g, 125 mmol) in dry N,N-dimethylformamide (62 mL) at room temperature was added imidazole (42.35 g, 622.9 mmol) followed by tert-butyldimethylsilyl chloride (41.36 g, 274 mmol). The resulting mixture was stirred at room temperature for 2.2 h, at which time TLC (hexanes-/ethyl acetate/chloroform; 2:1:1) showed complete disilylation. The reaction mixture was poured into H2O (1 L) and the resulting mixture was extracted with hexanes (3×500 mL). The combined extracts were washed with H2O and brine (500 mL ea). The organic phase was dried over MgSO4, filtered, and concentrated to give the crude disilyl ether (46.93 g) as a clear oil. This material was benzylated without further purification.
[2] Kozikowski, A. P.; Lee, J. *J. Org. Chem.* 1990, 55, 863-870.

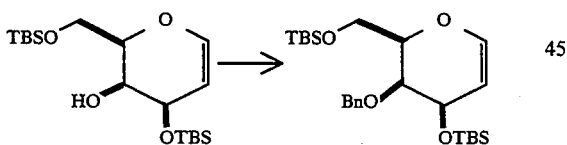

4-O-Benzyl-3,5-di-O-tert-butyidimethylsilyl-D-galactal

To a stirred 0° C. solution of the crude alcohol (46.93 g, ca. 125 mmol) in a mixture of THF and DMF (4:1 v/v, 500 mL total) was added benzyl bromide (29.7 mL, 249 mmol) under argon. A 50% suspension of NaH in mineral oil (15 g, 312.5 mmol) was added portionwise over 1 h. The resulting mixture was allowed to warm to room temperature with stirring. TLC showed no starting material after 2 h from the complete addition of NaIl. The mixture was cooled to 0° C. and anhydrous methanol (20 mL) was cautiously added over 30 min. The resulting mixture was allowed to stir for an additional 30 min while warming to room temperature. H2O (100 mL) was added and the mixture was poured into additional H2O (900 mL) and extracted with diethyl ether (3×500 mL). The combined ether extracts were sequentially washed with H2O and brine, dried over MgSO4, filtered and concentrated to a yellow oil (ca. 80 g, CJF-2-134). This material was used without further purification.

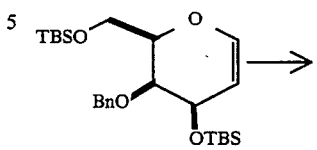

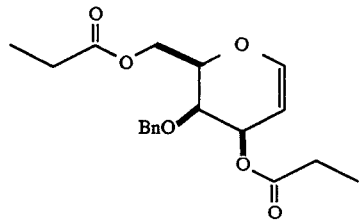

4-O-Benzyl-3,5-dipropionyl-D-galactal

To a solution of the crude 4-O-Benzyl-3,5-di-O-tert-butyldimethylsilyl-D-galactal (ca. 80 g, CJF-2-134) in THF (200 mL) was slowly added a 1.0M solution of tetra-butylammonium fluoride in THF (275 mL, 275 mmol). The resulting clear, orange solution was stirred at room temperature for 2 h, at which time TLC showed no remaining silyl ether. The mixture was concentrated by rotary evaporation and the residue was acylated directly.

The crude diol was dissolved in CH2Cl2 (500 mL) and the resulting stirred solution was cooled to 0° C. under argon. Triethylamine (104.5 mL, 750 mmol), N,N-dimethylaminopyridine (1.00 g), and propionic anhydride (48.1 mL) were sequentially added, the latter over ca. 15 min. The resulting solution was stirred at 0° C. for 30 min, then allowed to warm to room temperature. Additional triethylamine (33 mL) and propionic anhydride (15 mL) were added after 1 h, and after an additional 4.5 h the reaction mixture was washed with saturated aqueous NaHCO3 (500 mL) and concentrated. The residue was suspended in diethyl ether (500 mL) and washed with saturated aqueous NaHCO3 (3×500 mL), H2O (2×500 mL), and brine (500 mL). The organic phase was dried over MgSO4, filtered and concentrated. The residue was chromatographed (hexanes/ethyl acetate; 10:1 to 1: 1 ) to afford the dipropionyl compound (ca. 60 g) and the monopropionyl by-product (3.4 g).

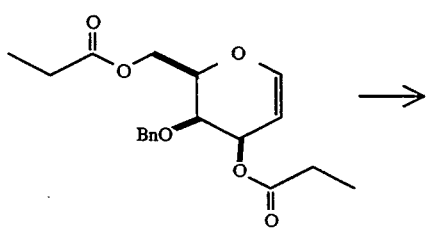

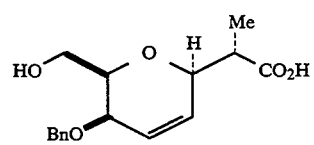

Carboxylic Acid

A solution of n-butyllithium in hexanes (63.4 mL of 2.5M, 158.5 mmol) was added over ca. 10 min to a stirred solution of hexamethyldisilazane (35.9 mL, 172.2 mmol) in THF (320 mL) at −78° C. and under nitrogen. The resulting solution was stirred for 30 min at −78° C. before a solution of tert-butyldimethylsilyl chloride (25.88 g, 172.5 mmol) in hexamethylphosphoramide (85 mL) was added over ca. 10 min. The resulting solution was stirred for 5 min before a solution of the dipropionate CJF-2-135 (20.00 g, 57.4 mmol) in THF (80 mL) was added dropwise over 25 min. The resulting solution was stirred at −78° C. for an additional 5 min, then allowed to slowly warm to ca. 0° C., at which point it was poured into a separatory funnel containing a 0° C. mixture of ice-water (1 L) and petroleum ether (1.5 L, bp 40°–60° C.). The mixture was shaken and the organic phase was separated and washed with a 0° C. saturated aqueous solution of NaCl (500 mL), dried over $Na_2SO_4$, filtered, and concentrated at 25°–30° C. by rotary evaporation. The resulting yellow oil was dissolved in benzene (1 L) and the solution was heated at reflux for 6 h. After partial cooling, the solution was concentrated by rotary evaporation and the residue was dissolved in a mixture of THF and $H_2O$ (250 mL ca) and the resulting mixture was stirred at room temperature for 24 h. (This step can be omitted.) The THF was removed by rotary evaporation, a 1M aqueous NaOH solution was added, and the suspension was stirred for 3 h at room temperature. The mixture was extracted with diethyl ether (2×250 mL), and the aqueous phase was acidified to ca. pH 2.5 with aqueous 1 M HCl (200 mL). The resultant suspension was extracted with diethyl ether (3×250 mL) then with ethyl acetate (2×250 mL). The combined organic extracts were dried over $Na_2SO_4$, filtered, and concentrated to afford the crude carboxylic acid as a clear oil (18.74 g).

1) after R. E. Ireland and M. G. Smith *J. Am. Chem. Soc.* 1988, 110, 854–860.

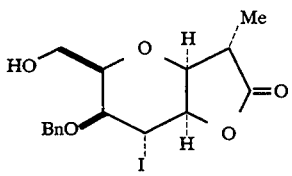

Iodolactone

To a mechanically stirred solution of the crude carboxylate (30.12 g, ca. 86 mmol) in saturated aqueous $NaHCO_3$ (1.00 L) at room temperature was added a solution of $I_2$ (59.25 g, 234 mmol) and KI (220.5 g, 1.329 mole) in $H_2O$ (375 mL). The resulting mixture was stirred at room temperature for 14 h, at which time TLC (hexanes/ethyl acetate; 1:1) showed no remaining starting material. A saturated aqueous solution of $Na_2S_2O_3$ (400 mL) was added and the resulting mixture was extracted with ethyl acetate (4×500 mL). The combined organic extracts were dried over $Na_2SO_4$, filtered, and concentrated to a yellow oil. This material was used without further purification. In a separate experiment, a 6 h reaction time was sufficient.

Note: The diastereometric methyl epimers may be chromatographically separated by silica gel chromatography (hexanes/ethyl acetate; 70:30) at this stage.

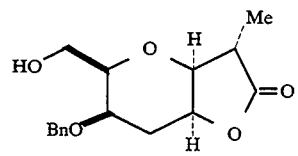

Lactone

A stirred solution of the iodolactone CJF-3-90, tri-n-butyltin hydride (28.0 mL, 104 mmol), and AIBN (100 mg) in benzene (600 mL) and under nitrogen was immersed in an 80° C. oil bath and maintained at reflux for 1 h. TLC (hexanes/ethyl acetate; 1:1) showed no remaining starting material. The solution was cooled to room temperature and concentrated by rotary evaporation. The residue was chromatographed (toluene to ethyl acetate) to afford the lactone (23.30 g, 79.7 mmol, 92.2% yield from the dipropionate) as a colorless crystalline solid.

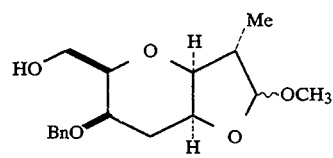

Methyl Acetals

To a stirred solution of the lactone (23.25 g, 79 mmol) in THF (500 mL) at −78° C. and under nitrogen was added a 1M solution of diisobutylaluminum hydride in hexane (258 mL, 258 mmol) by addition funnel over ca. 30 min. After an additional 1 h at −78° C., anhydrous methanol (90 mL) was cautiously added over 15 min, then saturated aqueous $NH_4Cl$ (90 mL) was added. The cooling bath was removed, diethyl ether (500 mL) was added, and the stirred mixture was allowed to warm to room temperature. The white gelatinous suspension was filtered through Celite and the residue was washed with ether (4×250 mL) and ethyl acetate (2×250 mL). The combined filtrate and washings were concentrated to a yellow oil. Dry toluene (500 mL) was added and the solution was reconcentrated by rotary evaporation to give the crude herniaoctal (18.46 g, ca. 0.8 mmol, 79% yield) as a clear, yellow oil.

The crude hemiacetal was dissolved in anhydrous methanol (1 L) and p-toluenesulfonic acid monohydrate (200 mg) was added. The resulting solution was stirred at room temperature for 14 h. TLC (hexanes/ethyl acetate/chloroform; 1: 1: 1 ) showed three products. Solid $NaHCO_3$ (2 g) was added and the mixture was concentrated by rotovap. The residue was applied directly to a silica gel column and eluted with hexanes-/ethyl acetate (1:1 to 0:1) to give a mixture of the two least polar products CJF-3-93A+B (13.98 g, 45.39 mmol, 72% yield) and the separate most polar product CJF-3-93C (4.65 g, 15.1 mmol, 24% yield). The least and most polar products (A and C) had the desired methyl configuration, while the intermediate $R_f$ product (B) had the undesired methyl configuration.

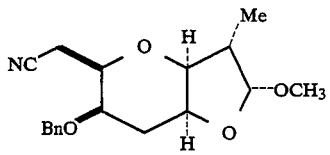

Nitrile

To a stirred solution of the alcohol CJF-3-93A (2.70 g, 8.77 mmol) in CH$_2$Cl$_2$ (200 mL) at −42° C. and under argon was added pyridine (1.56 mL, 19.3 mmol) followed by the dropwise addition over 5 min of trifluoromethanesulfonic anhydride (2.22 mL, 13.15 mmol). The resulting mixture was stirred at −42° C. for 40 min, at which time TLC showed no starting material. Saturated aqueous NaHCO$_3$ (250 mL) and diethyl ether (400 mL) were added and the separated organic layer was washed with H$_2$O (2×400 mL) and brine (200 mL). Drying over Na$_2$SO$_4$, filtration, and rotary evaporation at near room temperature gave the crude filtrate as a clear, yellow oil. This was concentrated further on a vacuum line for 10 min before being used directly in the next step.

The crude filtrate was dissolved in N,N-dimethylformamide (40 mL) at 0° C. and under argon. To the stirred clear, pale yellow solution was added NaCN (1.718 g, 35.05 mmol). As the resulting mixture was allowed to warm to room temperature and stir over 40 min, it became dark. TLC at this point showed no remaining starting material. Saturated aqueous NaHCO$_3$ (200 mL) and diethyl ether (250 mL) were added and the separated organic phase was washed with H$_2$O (2×250 mL). The combined aqueous phases were extracted with diethyl ether (2×250 mL) and the combined organic fractions were washed with H$_2$O (2×250 mL) and brine (200 mL). Drying over Na$_2$SO$_4$, filtration, concentration, and silica gel chromatography gave the nitrile (1.211 g, 3.82 mmol, 44% yield over two steps) as a clear oil.

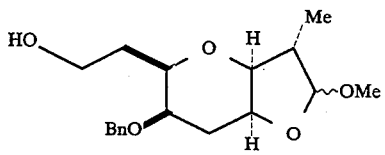

C38-primary alcohol

To a stirred solution of the nitrile CJF-3-97A (5.29 g, 16.7 mmol) in CH$_2$Cl$_2$ (250 mL) at −78° C. and under argon was added a 1M solution of diisobutylaluminum hydride in hexane (25.0 mL, 25.0 mmol) over 15 min. The resulting solution was stirred at -78 ° C. for an additional 45 min before 1M aqueous HCl (50 mL) was added. The cooling bath was removed and the resulting mixture was allowed to warm to 0° C. over 30 min. Diethyl ether (600 mL) was added and the mixture was washed with additional 1M HCl then brine (50 mL ca.). The combined aqueous phases were extracted with ether (2×50 mL) and the combined organic fractions were dried over Na$_2$SO$_4$, filtered, and concentrated to a yellow oil. This material was used directly without further purification.

The crude aldehyde was dissolved in methanol (100 mL) and the stirred solution was cooled to 0° C. before NaBH$_4$ (1.00 g, 26.7 mmol) was added. The cooling bath was removed and after 10 min, the solvent was removed by rotary evaporation. The residue was suspended in H$_2$O (100 mL) and extracted with ethyl acetate (4×100 mL). The combined extracts were washed with brine (100 mL), dried over Na$_2$SO$_4$, filtered, concentrated and chromatographed to give the primary alcohol (4.384 g, (13.6 mmol, 81% yield over two steps) as a clear, colorless oil.

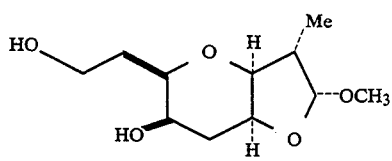

Diol

To a stirred solution of the benzyl ether CJF-3-98+99 (5.27 g, 16.3 mmol) in methanol (200 mL) was added 10% Pd(OH)$_2$ on carbon (1 g). The rapidly stirred mixture was evacuated and refilled with H$_2$ four times, then stirred under 1 atm of H$_2$ for 13 h. TLC at this point showed no remaining benzyl ether. The mixture was filtered through Celite along with methanol washes, and the combined filtrate and washes were concentrated to a clear oil (3.685 g, 15.9 mmol, 97% yield).

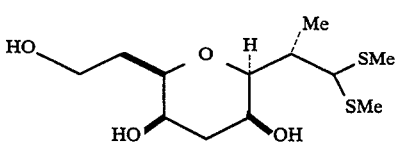

Dimethyl Acetal

To a stirred solution of the methyl acetal (3.571 g, 15.37 mmol) in CH$_2$Cl$_2$ (60 mL) at −78° C. and under argon was condensed methyl mercaptan (ca. 20 mL). The resulting solution was warmed to 0° C. and BF$_3$.OEt$_2$ (2 mL) was added. After stirring for 30 min at 0° C., TLC (ethyl L acetate) showed complete conversion to one higher R$_f$ spot. Saturated aqueous NaHCO$_3$ (50 mL) was cautiously added dropwise, H$_2$O (50 mL) was added and the separated aqueous phase was extracted with CH$_2$Cl$_2$ (4×150 mL). The combined organic fractions were dried over anhydrous K$_2$CO$_3$, filtered, and concentrated to give the dithioacetal (4.206 g, 14.19 mmol, 92.3% yield) as a clear, colorless foam.

Trisilylether- Dimethyl Acetal Poor Yield

To a solution of the triol (1.26 g, 4.29 mmol) in methylene chloride (30 mL) at 0° C. was added triethylamine (4.5 mL, 32.2 mmol) followed by t-butyldimethylsilyltriflate (3.7 mL, 16.2 mmol). After 1 h, TLC analysis (hexanes/EtOAc; 20:1) showed the presence of starting material in addition to mono- ,di- and trisyliated adducts. At this time, additional triethylamine (4.5 mL, 32.2 mmol) and t-butyldimethylsilyltriflate (3.7 mL, 16.2 mmol) was added to the reaction mixture and the resulting solution was stirred for 2 h. The reaction was then quenched by the addition of saturated aqueous sodium bicarbonate (50 mL). The resulting mixture was thoroughly extracted with ethyl acetate and the combined organics were washed with brine, m dried over sodium sulfate and concentrated in vacuo. The residual oil was purified by flash chromatography (hexanes-/ethyl acetate; 50:1 ) to provide the trisilylether (2.2 g, 80% yield) as a light yellow oil.

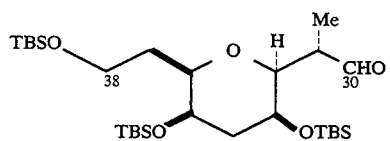

Aldehyde

To a stirred solution of the dithioacetal CJF-3-103 (640 mg, 1.00 H mmol) in acetone/H2O (9:1 v/v, 50 mL) at room temperature was added solid NaHCO3 (252 mg, I mmol) followed by 12 (254 mg, 1 mmol). After 30 min, the red reaction mixture was cooled to 0° C. and additional NaHCO3 (252 mg) and I2 (254 mg) were added. After an additional 30 min at 0° C., additional NaHCO3 (252 mg)and I2 (254 mg) were added and the mixture was allowed to warm to room temperature. After a total of 190 min, TLC showed no remaining starting material. The reaction mixture was poured into a separatory funnel containing ethyl acetate (50 mL) and 10% aqueous Na2S2O3 (50 mL). After shaking and removal of the aqueous phase, the clear, colorless organic phase was washed with H2O and brine (50 mL ca.). The combined aqueous fractions were extracted with ethyl acetate (2×50 mL) and the combined organic fractions were dried over Na2SO4, filtered, and concentrated. Silica gel chromatography (hexanes-/ethyl acetate; 10:1) of the residue gave the aldehyde (509 mg, 907 μmol, 91% yield) as a clear, colorless oil.

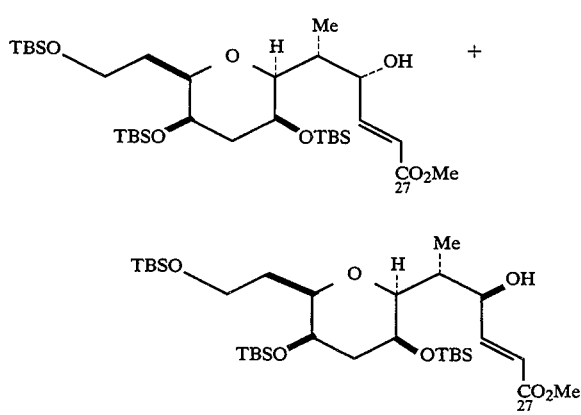

Methyl Acrylates

A mixture of the aldehyde (989 mg, 1.75 mmol) and trans-β-iodomethylacrylate (1.85 g, 8.74 mmol) was dissolved in THF (10 mL) under nitrogen. To the stirred room temperature solution was added powdered CrCl2 containing 1% NiCl2 by mass (ca. 750 mg total). After 50 min, additional 1% NiCl2/CrCl2 (ca. 500 mg) was added to the pale green suspension, and the resulting mixture was stirred for 22 h at room temperature. The reaction mixture was diluted with saturated aqueous NH4Cl (20 mL) and extracted with diethyl ether (4×10 mL) then with ethyl acetate (2×10 mL). The combined extracts were concentrated by rotary evaporation, and the residue was suspended in ethyl acetate (20 mL) and washed with H2O (2×20 mL) and brine (10 mL). The ethyl acetate solution was dried over Na2SO4, filtered, and concentrated. Repeated silica gel chromatography of the residue (ca. 150 g SiO2, hexanes/tert-butylmethyl ether; 6:1; then hexanes/ethyl acetate/CHCl3, 1:1) gave the two diastereomeric products (912 mg, 1.47 mmol, 84% combined yield).

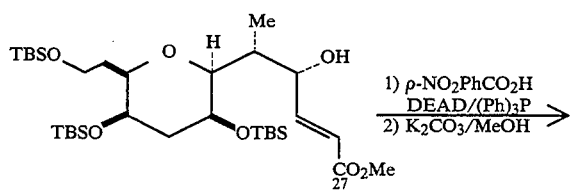

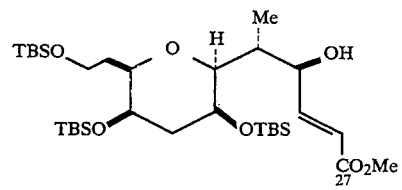

C30 Inversion

To a stirred solution of triphenylphosphine (373mg, 1.42 mmol) and p-nitrobenzoic acid (238 mg, 1.42 mmol) in diethyl ether (20 mL) and toluene (10 mL) at room temperature was added a solution of the alcohol (441 mg, 712 μmol) in diethyl ether/toluene (2:1 v/v, 10 mL). To the resulting clear solution was added diethylazidodicarboxylate (224 μL, 1.42 mmol) dropwise. The resulting clear, yellow solution was stirred at room temperature for 4 h, at which time TLC (hexanes/ethyl acetate/chloroform; 5:1:1) showed no remaining starting material. Saturated aqueous NH4Cl (30 mL) was added and the separated organic phase was washed with saturated aqueous NaHCO3, H2O, and brine (10 mL ea). The organic phase was dried over Na2SO4, filtered, concentrated and chromatographed to give the p-nitrobenzoate as a clear, yellow oil (522 mg).

To a stirred 0° C. solution of the p-nitrobenzoate (522 mg) in methanol (10 mL) was added K2CO3 (5 mg). After stirring for 30 min, TLC showed no remaining starting material. Acetic acid (5 μL) was added and the resulting mixture was concentrated and the residue chromatographed to give the alcohol (404 mg, 91% yield) as a colorless oil.

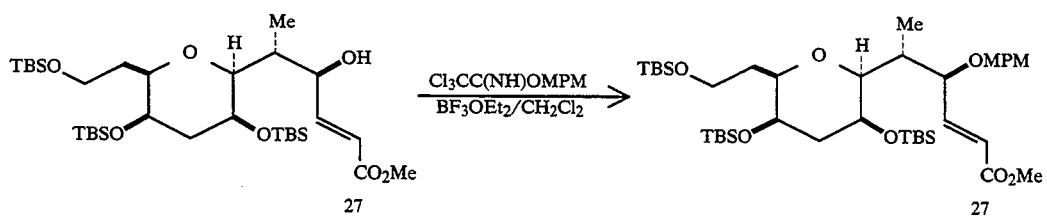

Methoxy Phenyl Methyl Ether Formation

To a stirred 0° C. solution of the alcohol (755 mg, 1.22 mmol) and p-methoxybenzyltrichloroacetimidate (3.446 g, 12.2 mmol) in CH$_2$Cl$_2$ (120 mL) at 0° C. was added a 0.1M solution of BF3.OEt$_2$ in CH$_2$Cl$_2$ (50 μL). The resulting orange solution was stirred for 10 min, at which time TLC showed no remaining starting material. Saturated aqueous NaHCO$_3$ (40 mL) was added, and after vigorous mixing the separated organic phase was dried over Na$_2$SO$_4$, filtered, and concentrated. The residue was chromatographed on silica gel (hexanes/ethyl acetate; 5:1) to give the p-methoxybenzyl ether (866 mg, 1.17 mmol, 96% yield) as a clear oil.

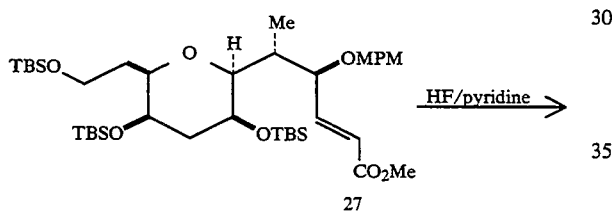

Triol

To a stirred solution of the trisilyl ether (986 mg, 1.33 mmol) in acetonitrile (25 mL) at 0° C. was added pyridine (500 μL) followed by the HF*pyridine reagent (5.0 mL, Aldrich) over 1 min. After 75 min, TLC (ethyl acetate) showed essentially complete reaction. Saturated aqueous NaHCO$_3$ (200 mL,) was cautiously added portionwise. The resulting mixture was extracted with ethyl acetate (3×200 mL,), and the combined extracts were dried over Na$_2$SO$_4$, filtered and concentrated to give the crude triol (590 mg) as a clear, orange oil.

$[\alpha]_D^{RT}- +29.7°$ (c=3.4mg/mL, MeOH).

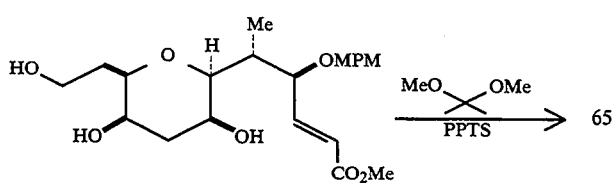

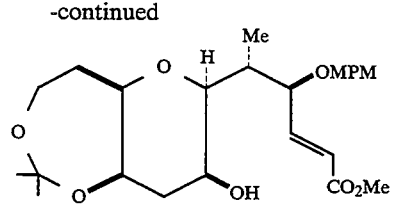

Acetonide

To a solution of the crude triol (560 mg, ca. 1.3 mmol) in CH$_2$Cl$_2$ (10 mL) at room temperature was added 2,2-dimethoxypropane (327 μL, 2.66 mmol) followed by pyridinium p-toluenesulfonate (5 mg). After 1 h, additional 2,2-dimethoxypropane (327 μL, 2.66 mmol) was added. The reaction solution was allowed to stir for a total of 24 h, at which time TLC showed complete conversion to a single higher R$_f$ spot. The reaction mixture was washed with saturated aqueous NaHCO$_3$, H$_2$O, and brine (50 mL ea), and the resulting organic phase was dried over Na$_2$SO$_4$, filtered, concentrated and the residue chromatographed (ethyl acetate/hexanes/triethylamine; 1:1:0.001 to 1:0:0.001) to give the 7-membered acetonide (516 mg) as a colorless foam.

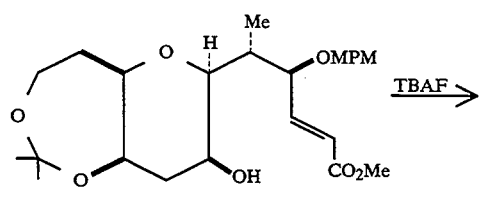

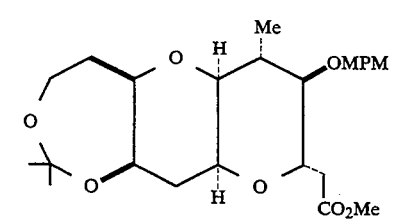

Michael-type Addition

To a stirred 0° C. solution of the hydroxy acrylate (420 mg, 904 μmol) in THF (36 mL) and anhydrous methyl acetate (4 mL) was added a 1 M solution of tetra-butylammonium fluoride (TBAF) in THF (9 mL, 9 mmol, Aldrich). Additional methyl acetate (4 mL) and TBAF solution (4.5 mL) were added after 1 h. After a total of 6 h at 0° C., the reaction solution was diluted with saturated aqueous NaHCO$_3$ (175 mL) and brine (175 mL) and extracted with ethyl acetate (3×100 mL). The combined extracts were washed with H$_2$O and brine (250 mL ea), dried over Na$_2$SO$_4$, filtered and concentrated. The residue was chromatographed on silica gel to give, in order of elution, starting material (57 mg), the desired cyclized product (336 mg, 723 μmol, 80% yield), and the undesired C29 epimeric cyclized product (16 mg) all as clear oils.

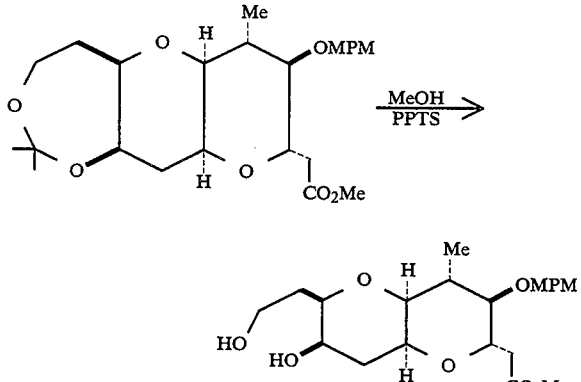

Diol

To a stirred solution of the acetonide (268 mg, 577 μmol) in methanol (10 mL) at room temperature was added pyridinium para-toluenesulfonate (5 mg). After 20 min of stirring at room temperature, TLC showed no remaining starting material. Solid NaHCO₃ (50 mg) was added and the mixture was concentrated by rotary evaporation. The residue was filtered through a short pad of silica gel with ethyl acetate, and the filtrate was concentrated to give the crude diol (232 mg, 547 μmol, 95% yield) as a clear, colorless oil. This was used without further purification.

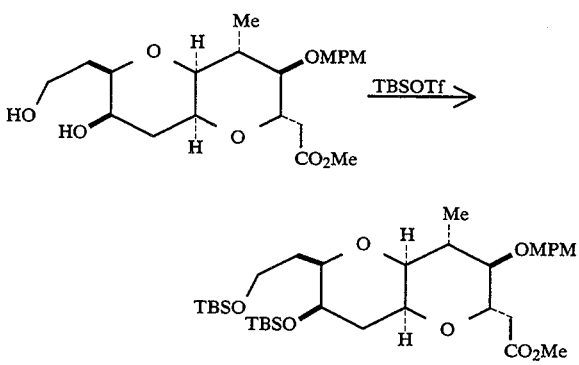

Disilyl Ether

To a stirred solution of the diol (230 mg, 542 μmol) at 0° C. and under argon was added triethylamine (605 μL, 4.33 mmol) followed by tert-butyldimethylsilyltrifluoromethane sulfonate (498 μL, 2.17 mmol). Additional triethylamine (303 μL) and tert-butyldimethylsilyltrifluoromethane sulfonate (249 μL) were added after 1 h. After 2 h total, the reaction mixture was washed with saturated aqueous NaHCO₃, dried over Na₂SO₄, filtered, and concentrated. The residue was chromatographed on silica gel (hexanes/ethyl acetate; 5:1) to give the disilyl ether (308.8 mg, 473 μmol, 87% yield) as a clear, colorless oil.

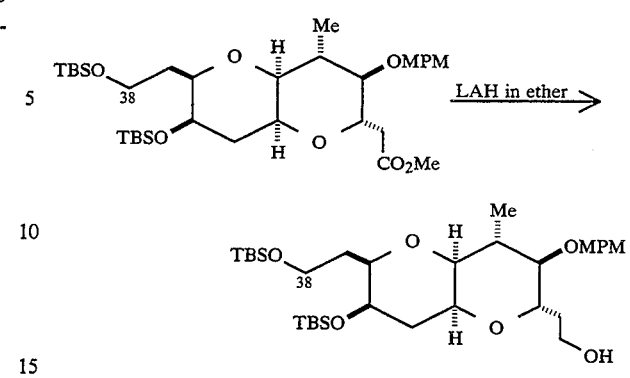

To a solution of ester (306 mg, 0.480 mmol) in ether (10 mL) at 0° C. was added a 1.6M solution of lithium aluminum hydride (0.60 mL, 2 eq) in diethyl ether. After 5 min, an aqueous solution saturated with Rochelle's salt and NH₄Cl was added and the resulting mixture was stirred vigorously until it formed two clear phases. The mixture was extracted with ethyl acetate (2×10 mL), and the combined extracts were dried over Na₂SO₄, filtered, and concentrated under reduced pressure. The residue was purified by silica gel column chromatography with hexanes/ethyl acetate/chloroform (5:1:1) to afford the alcohol (278 mg, 95.2% yield).

IR (film) 775 cm⁻¹, 835, 1251, 1472, 1514, 2930, 2956, 3453.

¹H NMR (CDCl₃): δ0.47 (6 H, s), 0.53 (3 H, s), 0.80 (3 H, s), 0.89 (9 H, s, t-Bu), 0.90 (9 H, s, t-Bu), 1.15 (3 H, d, J=7.1 Hz), 1.60 (1 H, m), 1.76 (2 H, m), 1.82 (1 H, m), 1.93 (1 H, m), 2.08 (2 H, m), 2.98 (1 H, br s), 3.06 (1 H, m), 3.37 (1 H, t, J=4.2 Hz), 3.50 (1 H, m), 3.71 (2 H, m), 3.79 (1 H, m), 3.80 (3 H, s, —OMe), 4.13 (1 H, m), 4.45 (2 H, d, J=10.9 Hz), 4.56 (2 H, d, J=10.9 Hz), 6.87 (2 H, d, J=8.5 Hz), 7.24 (2 H, d, J=8.5 Hz).

HRMS (FAB) calcd for C₃₃H₆₀O₇Si₂+Na 647.3775, found 647.3763.

[α]_D −20.2° (c 0.99, MeOH).

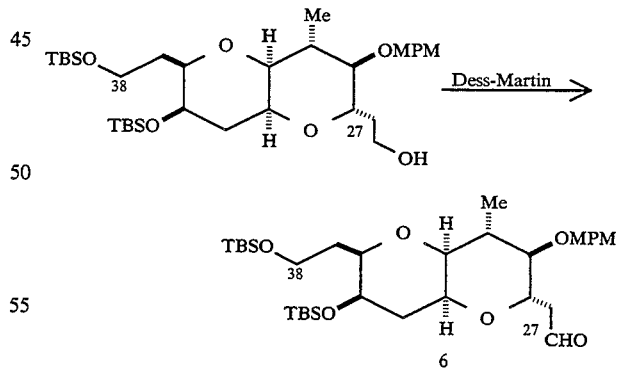

To a stirred solution of alcohol (100 mg, 0.164 mmol) in dichloromethane (5 mL) was added the Dess-Martin periodinane reagent (150 mg, 2.5 eq) at room temperature. After ca. 1 h, TLC showed no remaining starting material. The reaction mixture was diluted with diethyl ether (25 mL) and an aqueous solution of sodium thiosulfate and NaHCO₃ (saturated) was added. The resulting mixture was stirred until two clear phases formed, then it was extracted with diethyl ether (2×15 mL). The combined extracts were dried over anhydrous Na₂SO₄, filtered, and concentrated. The residue was purified by silica gel column chromatography with 12% ethyl acetate in hexanes to give the aldehyde (92.5 mg, 92.8% yield).

COMPOUND 7

Compound 7 was synthesized according to the following procedure.

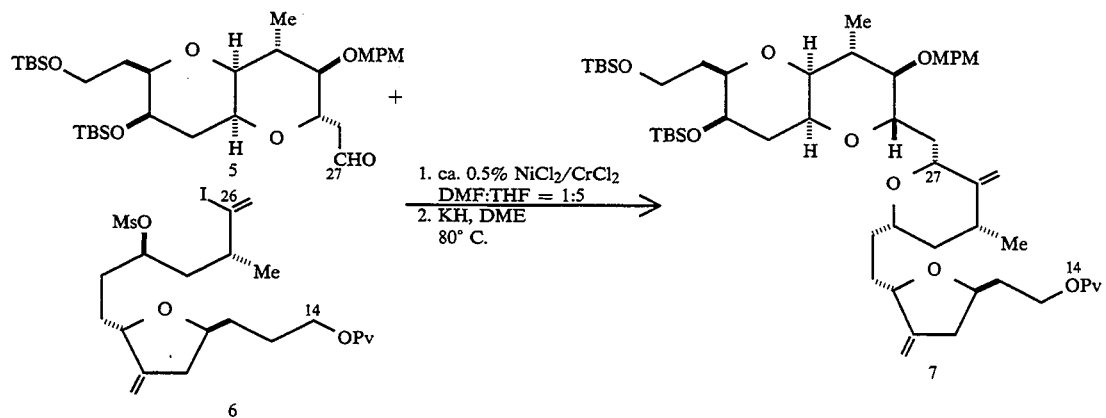

Trisaccharide

To a solution of aldehyde (102 mg, 0.168 mmol) and mesylate (141.6 mg, 0.255 mmol) in 17% (v/v) DMF in THF (2.08 mL) was added ca. 20 mg of 0.1% NiCl₂ in CrCl₂ and ca. 10 mg of 1% NiCl₂ in CrCl₂. The metal reagents were added in the same proportions four more times over 26 h. The reaction mixture was diluted with saturated aqueous NH₄Cl (8 mL), and extracted with ethyl acetate (3×10 mL). The combined organic layers were dried over anhydrous Na₂SO₄ and concentrated under reduced pressure. The crude residue was dried by azeotropic removal of water with benzene, and dried further under high vacuum. The residue was dissolved in 1,2-dimethoxyethane (25 mL) and a 35% by weight dispersion of KH (ca. 10 mg) in mineral oil was added. The reaction flask was immersed in an 80° C. oil bath for 2.5 min, then cooled to 0° C. in an ice-water bath. The reaction mixture was diluted with anhydrous ether (30 mL), filtered through a silica gel pad along with additional anhydrous ether (30 mL) washes. The filtrate was concentrated and the residue was purified by silica gel column chromatography with 12% ethyl acetate in hexanes to give the product (86 mg, 53% yield).

IR (film) 722 cm⁻¹, 835, 1040, 1250, 1463, 1514, 1755, 2854, 2926.

$[\alpha]_D$: 20.0° (C 3.3, MeOH).

HRMS (FAB) calcd for $C_{54}H_{92}O_{10}Si_2$+Na 979.6124, found 979.6149.

¹H NMR (C₆D₆): δ 0.04 (3 H, s), 0.10 (3 H, s), 0.11 (3 H, s), 0.14 (3 H, s), 0.97 (3 H, d, J=6.5 Hz), 1.00 (9 H, s), 1.02 (9 H, s), 1.11 (1 H, m), 1.16 (9 H, s) 1.26 (4 H, m), 1.51–1.90 (11 H, m), 1.98–2.20 (5 H, m), 2.27 (2 H, m), 2.39 (1 H, m), 2.45 (1 H, m), 3.23 (2 H, t, J=9.0 Hz), 3.31(3 H, s), 3.53 (1 H, m), 3.68 (2 H, m), 3.75 (1 H, m), 3.86 (1 H, m), 3.93 (1 H, m), 4.02 (2 H, m), 4.19 (1 H, m), 4.31 (1 H, m), 4.44 (1 H, m), 4.54 (2 H, q, J=7.9 Hz), 4.83 (1H, s), 4.86 (1 H, br d), 4.91 (1 H, br d), 5.14 (1H, s), 6.80 (2 H, d, J=8.4 Hz), 7.28 (2 H, d, J=8.4 Hz).

C14 Alcohol

To a solution of C14-pivaloate (27.8 mg, 0.029 mmol) in anhydrous ether (2 mL) of was added a 1.6M solution of lithium aluminum hydride in diethyl ether (38 μL, 61 μmol) at 0° C. The reaction mixture was stirred for 5 min, diluted with EtOAc (4 mL), and an aqueous solution saturated with Rochelle's salt and NH₄Cl was added. The reaction mixture was stirred until it formed a clear aqueous layer. The organic layer was separated and the aqueous layer was extracted with EtOAc (2×4 mL). The combined organic layers were dried over Na₂SO₄ and concentrated under reduced pressure. The oily residue was purified by column chromatograpy with 50% hexanes in ethyl acetate to afford the alcohol (25 mg, 98.5% yield).

COMPOUND 8

Compound 8 was synthesized from diacetone glucose according to the following procedure.

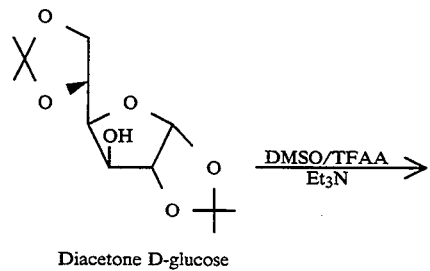

Diacetone D-glucose

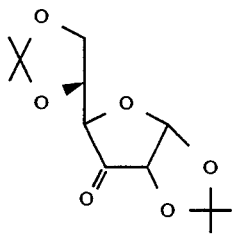

1,2:5,6-di-O-isopropylidene-α-D-ribo-hexofuranos-3-ulose (1)¹

To a stirred solution of DMSO (10.65 mL, 150.1 mmol) in CH₂Cl₂ (300 mL) at −78° C under argon was added trifluoroaeetie arthydride (16.00 mL, 113.3 mmol) dropwise. The resulting white suspension was stirred at −78° C. for 10 min before a solution of 1,2:5,6- di-O-isopropylidene-α-D-glucofuranose (20.0 g, 76.7 mmol) in CH₂Cl₂ (200 mL) was slowly added by cannula. The resulting mixture was stirred at −78° C. for 1 h before triethylamine (30.4 mL, 218 mmol) was slowly added and the reaction mixture allowed to warm to room temperature. Saturated aqueous NH₄Cl (100 mL) was added and the organic phase was separated and washed with cold 1M aqueous HCl (2×100 mL), H₂O (100 mL), saturated aqueous NaHCO₃ (100 mL), H₂O (100 mL), and saturated aqueous NaCl (100 mL). The organic phase was dried, filtered and concentrated to give the crude ketone (22.3 g) as a pale yellow oil. This material was used directly without further purification.

1) Brimacombe, J. S.; Bryan, J. G. H.; Husain, A.; Stacey, M.; Jolly, M. S. *Carb Res.* 1967, 3, 318–324.

Lit.:[1] [α]$_D$: +105° (c 2, CHCl₃), ν$_{max}$ 1740 cm⁻¹.

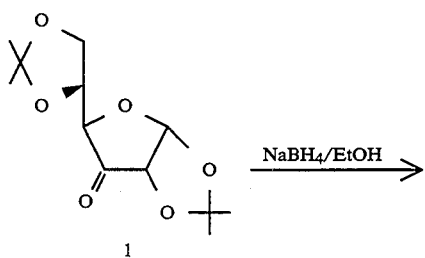

1.2:5.6-di-O-isopropylidene-α-D-allofuranose (2)[2]

To a stirred solution of the ketone (22.3 g, ca. 75 mmol) in 95% ethanol (200 mL) at 0° C. was added NaBFH₄ (5.8 g, 154 mmol) portionwise over 20 min. After stirring an additional 10 min, TLC showed no remaining starting material. The solvent was removed by rotory evaporation and the residue was suspended in ethyl acetate (200 mL) and washed with H₂O (2×100 mL) and saturated aqueous NaCl (100 mL). The organic phase was dried over Na₂SO₄, filtered, and concentrated to give the crude allose as a white solid (19.64 g, ca. 75 mmol, 98% yield over two steps).

2) Theander, O. *Acta Chem. Scand.* 1964, 18, 2209–2216.

Lit.[2] mp 76°–77° C. (benzene/petroleum ether), [α]$_D^{22}$+37.7° (C 0.5, H₂O).

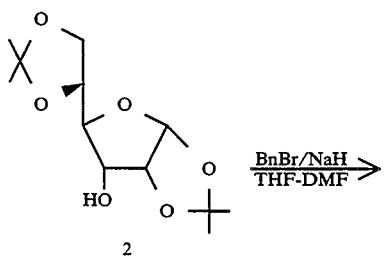

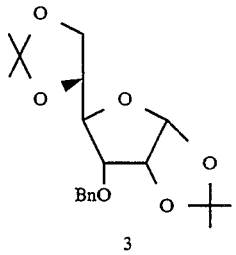

3-O-Benzyl-1.2:5.6-di-O-isopropylidene-α-D-allofuranose (3)

To a stirred solution of the allose diacetonide 2 (19.6 g, ca. 75 mmol) in THF-DMF (500 mL, 4:1 v/v) at 0° C. and under argon was added a 60% sodium hydride dispersion in mineral oil (6.0 g, 150 mmol) portionwise over 30 min. The resulting mixture was allowed to warm to room temperature over 1 h, then it was re, cooled to 0° C. before benzyl bromide (25.7 g, 17.9 mL, 150 mmol) and tetra-n-butlyammonium iodide (1.0 g) were added. The resulting mixture was allowed to warm to room temperature and stir for 16 h. The reaction mixture was cooled to 0° C. and anhydrous methanol (20 mL) was cautiously added over 30 min. The resulting mixture was allowed to warm to room temperature and stir for 1 h before the THF was removed by rotary evaporation. The residue was suspended in H₂O (250 mL) and extracted with ethyl acetate (4×200 mL). The combined organic fractions were washed with H₂O (500 mL) and brine (200 mL), dried over Na₂SO₄, filtered, and concentrated to a clear, yellow oil (46.8 g crude). This material was used without further purification.

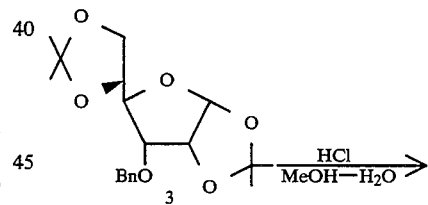

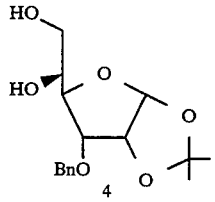

3-O-Benzyl-1,2-O-isopropylidene-α-D-allofuranose (4)

To a stirred mixture of the crude benzyl ether-diacetonide 3 (46.8 g, ca. 75 mmol) in methanol-H₂O (500 mL, 4:1 v/v) at 0° C. was added 1M aqueous HCl (50 mL). The resulting mixture was allowed to warm to room temperature and stir for 7.5 h, before being neutralized by the portionwise addition of solid NaHCO₃ (20 g). The methanol was removed by rotary evaporation, and the resulting aqueous suspension was extracted with ethyl acetate (6×100 mL). The combined organic fractions were dried over Na₂SO₄, filtered, and concentrated to a clear, yellow oil. This material was used without further purification.

IR (film): 3420 cm$^{-1}$, 3070, 3065, 3032, 2986, 2934, 2901, 1498, 1454, 1434, 1423, 1409, 1382, 1373, 1316, 1250, 1214, 1167, 1137, 1122, 1095, 1025, 697.

$^1$H NMR (CDCl$_3$): δ 1.35 (3H, s), 1.58 (3H, s), 2.71 (1H, bt, J=5.7 Hz), 2.82 (1H, d, J=3.5 Hz), 3.67 (2H, m), 3.93 (1H, dd, J=4.3, 8.9 Hz), 4.00 (1H, m), 4.09 (1H, dd, J=3.2, 8.9 Hz), 4.55 (1H, d, J=11.4 Hz), 4.61 (1H, m), 4.77 (1H, d, J=11.4 Hz), 5.75 (1H, d, J=3.8 Hz), 7.25–7.50 (5H, m).

$^{13}$C NMR (CDCl$_3$): 26.56, 26.74, 63.05, 71.00, 72.13, 77.00, 77.33, 79.06, 104.21, 113.15, 128.20, 128.53, 136.85.

[α]$_D$: +107.3° (C 6.65, CHCl$_3$).

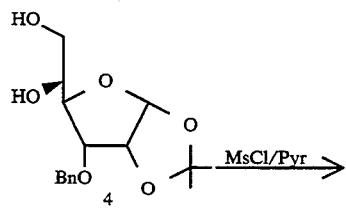

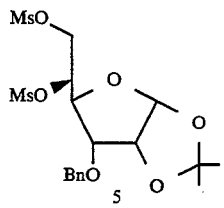

3-O-Benzyl-1.2-O-isopropylidene-5.6-di-O-methanesulfonyl-α-D-allofuranose (5)[6]

To a solution of the crude diol 4 (ca. 75 mmol) in CH$_2$Cl$_2$ (300 mL) at 0° C. was added pyridine (90 mL, 1.1 mol) followed by methanesulfonyl chloride (30 mL, 388 mmol). The resulting solution was stirred at 0° C. for 1 h, then allowed to warm to room temperature and stir over an additional 3 h. Saturated aqueous NaHCO$_3$ (100 mL) was cautiously added portion-wise over 30 min. The organic phase was separated and washed with saturated aqueous NaHCO$_3$ (100 mL), 1M aqueous HCl (2×100 mL), H$_2$O (100 mL), and brine (100 mL). The organic phase was dried over Na$_2$SO$_4$, filtered, and concentrated to an orange oil. The crude dimesylate 5 was used without further purification.

[6] after: Brimacombe, J. S.; Mofti, A. M.; Tucker, L. C. N. *J. Chem. Soc.* (C) 1971, 2911–2915; where they used the 3-O-methyl analogue.

IR (film): 3032 cm$^{-1}$, 2970, 2939, 1455, 1361, 1247, 1241, 1219, 1176, 1135, 1122, 1104, 1093, 1027, 1010, 972, 924, 872, 831, 797, 746, 701, 665.

$^1$H NMR (CDCl$_3$): δ 1.36 (3H, s), 1.58 (3H, s), 3.00 (3H, s), 3.03 (3H, s), 3.95 (1H, dd, J=4.3, 8.8 Hz), 4.20 (1H, dd, J=3.2, 8.8 Hz), 4.39 (2H, d, J=3.5 Hz), 4.56 (1H, d, J=11.2 Hz), 4.59 (1H, m), 4.75 (1H, d, J=11.2 Hz), 5.10 (1H, m), 5.75 (1H, d, J=3.6 Hz), 7.25–7.50 (5H, m).

$^{13}$C NMR (CDCl$_3$): 26.53, 26.83, 37.78, 38.74, 66.67, 72.29, 76.46, 77.11, 77.65, 104.34, 113.70, 128.41, 128.61.

[α]$_D$: +70.0° (c 2.86, CHCl$_3$).

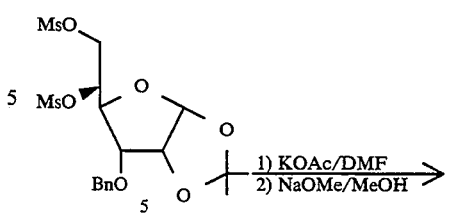

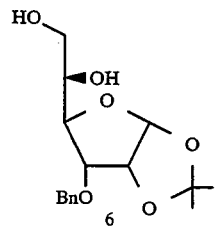

3-O-Benzyl-1,2-O-isopropylidene-α-L-talofuranose (6)[6]

To a solution of the crude dimesylate (ca. 75 mmol) in DMF (350 mL) was added powdered potassium acetate (20 g, 204 mmol). The resulting mixture was stirred at room temperature for 1 h, then it was heated to 145°–151 ° C. for 18 h. TLC showed no starting material, but three products. The mixture was cooled to near room temperature, diluted with H$_2$O (1.4 L), and extracted with ethyl acetate (4×500 mL). The combined extracts were washed with H$_2$O and brine, dried over Na$_2$SO$_4$, filtered, and concentrated to a dark brown oil. This material was dissolved in anhydrous methanol (250 mL), and the resulting solution was cooled to 0° C. while stirring under nitrogen. A freshly prepared solution of sodium (5 g) in methanol (200 mL) was slowly added via cannula, and the resulting solution was stirred at 0° C. for 1 h, then allowed to warm to room temperature with stirring over 3 h. Solid NH$_4$Cl (10 g) was added and the solvent was removed by rotary evaporation. The residue was suspended in ethyl acetate (100 mL) and filtered through a glass frit. The solid residue was washed with ethyl acetate (50 mL), and the combined filtrate and washes were concentrated to a brown oil. Silica gel chromatography (ethyl acetate-hexanes, 4:1 to 4:0) afforded the diol 6 as a clear, colorless oil: 14.6 g (47.2 mmol, 63% yield over five steps).

IR (film): 3431 cm$^{-1}$, 3064, 3032, 2987, 2935, 1653, 1496, 1454, 1382, 1373, 1309, 1216, 1168, 1129, 1102, 1075, 1025, 921, 872, 739, 699, 666.

$^1$H NMR (CDCl$_3$): δ 1.38 (3H, s), 1.59 (3H, s), 2.51 (2H, bs) m), 3.93 (1H, dd, J=4.3, 8.9 Hz), 4.05 (1H, dd, J=2.2, 9.0 Hz), 4.53 (1H, m), 4.58 (1H, d, J=11.7 Hz), 4.76 (1H, d, J=11.7 Hz), 5.73 (1H, d, J=3.6 Hz), 7.25–7.50 (5H, m).

$^{13}$C NMR (CDCl$_3$): δ 26.55, 26.84, 64.84, 69.85, 72.33, 77.18, 77.68, 79.75, 104.41, 113.13, 127.94, 128.36, 137.25.

[α]$_D$: +93.1° (c 9.99, CHCl$_3$).

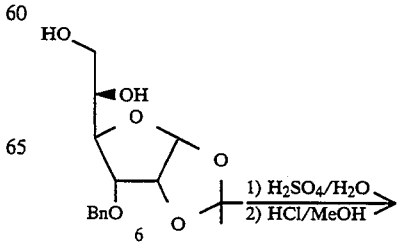

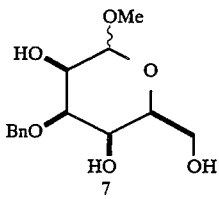

α,β-L-talopyranosides (7)

A stirred solution of the acetonide 6 (14.6 g, 47.2 mmol) in 0.25M aqueous H₂SO₄ (500 mL) was heated at 60° C. for 1 h, then allowed to cool to room temperature with stirring over an additional 3 h. The solution was carefully neutralized with portion-wise additions of solid BaCO₃ (12.33 g, 62.5 mmol). The suspension was filtered through a fritted glass funnel along with H₂O washes. The combined filtrate and washes were concentrated by rotovap to a syrup which was dried further on a vacuum line overnight to give 12.7 g (ca. 47.2 mmol) of crude L-3-O-benzyltalose.

To a solution of the L-3-O-benzyltalose (11.7 g, 43.5 mmol) in anhydrous methanol (250 mL) was cautiously added acetyl chloride (3.0 mL, 34.6 mmol) dropwise. The resulting solution was heated at reflux for 72 h, then cooled to room temperature. Solid NaHCO₃ (5g) was added and the solvent was removed by rotary evaporation. The residue was suspended in ethyl acetate (250 mL) and filtered. The solids were washed with additional ethyl acetate, and the combined washes and filtrate were concentrated to an orange oil: 10.87 g (38.4 mmol, 81% yield).

Lit.[8]: α-D-methyl-talopyranoside: [α]$_D$: 24 +98° (c 1.3, H₂O). α-D-methyl-talopyranoside: [α]$_D$:24 +28.5° (C 1.5, H₂O).

Lit.[9]: α-D-methyl-talopyranoside: [α]$_D$: +105° (H₂O).

Lit.[10]: α-D-methyl-talopyranoside: [α]$_D$: 106.5° (C 0.97, H₂O).

8) Angyal, S. J.; Bodkin, C. L.; Parrish, F. W. Aust. J. Chem. 1975, 28, 1541–1549.
9) Gorin, P. A. I. Can. J. Chem. 1960, 38, 641–651.
10) Evans, M. E.; Parrish, F. W. Carb. Res. 1977, 54, 105–114.

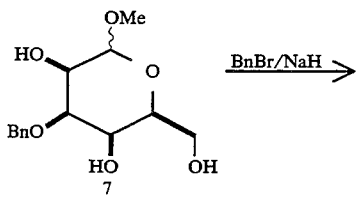

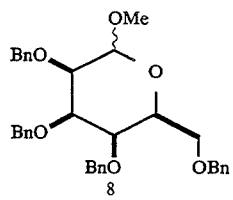

α,β-L-methyl-2,3,4,6-tetra-O-benzyltalopyranosides (8)

To a stirred solution of the crude methyl talosides (23.8 g, 84 mmol) in DMF (250 mL) at 0° C. under argon was added sodium hydride (15.2 g of a 60% dispersion in mineral oil, 380 mmol) portionwise over 30 min. The resulting mixture was allowed to warm to room temperature with stirring over 1 h, then it was recooled to 0° C. Benzyl bromide (38 mL, 318 mmol) was added dropwise over 20 min, and after an additional 20 min, tetra-n-butyl ammonium iodide (TBAI, 2 g) was added. The mixture was stirred at 0° C. for 30 min, then allowed to warm to room temperature and stir for 18 h. TLC at this point showed remaining starting material. The mixture was re-cooled to 0° C., and additional sodium hydride (5.1 g of 60 % dispersion, 128 mmol), benzyl bromide (12.7 mL, 106 mmol), and TBAI (2 g) were added sequentially. The mixture was again allowed to warm to room temperature and stir for 6 h. After a total of 24 h reaction time, the reaction mixture was cooled to 0° C., anhydrous methanol (20 mL) was cautiously added, and the mixture stirred for 1 h. The reaction mixture was then diluted with H₂O (1 L) and extracted with diethyl ether (4×500 mL). The combined organic extracts were washed with H₂O and brine (500 mL ca.), dried over Na₂SO₄, filtered and concentrated. Silica gel chromatography of the residue gave 8 as a clear oil: 44.31 g (80 mmol, 95% yield).

IR (CCl₄): 3064 cm⁻¹, 3030, 2897, 1497, 1454, 1360, 1134, 1101, 1028, 735, 697.

¹H NMR (CDCl₃): δ 3.34 (3H, s), 3.71–3.76 (4H, m), 3.91 (1H, bs), 3.93 (1H, m), 4.49 (1H, J=11.8 Hz), 4.52 (2H, s), 4.56 (1H, d, J=11.8 Hz), 4.75 (2H J=11.7 H2), 4.87 (1H, d, J=1.5 Hz), 4.88 (1H, d, J=11.7 Hz), 4.97 (1H, d, 11.7 Hz), 7.20–7.50 (20H, m).

¹³C NMR (CDCl₃): δ 5.94 ppm, 69.57, 70.61, 71.04, 73.07, 73.28, 73.52, 73.70, 74.18, 100.23, 127.14, 127.24, 127.36, 127.45, 127.58, 127.75, 128.03, 128.14, 128.19, 128.32, 138.24, 138.36, 138.70, 139.06.

[α]$_D$: −24.8° (c 0.81, CHCl₃).

Lit.[11]: (α-D-anologue) ¹HNMR (CDCl₃) 4.79 (J₁,₂ 1.8 Hz, H1), 5.08 (H2), 5.25 (H4), 4.22 (H5), 4.22 (H6), 3.42 (OCH₃), 2.00, 2.08, 2.16.

11) Banaszek, A.; Zamojski, A. Pol. J. Chem. 1979, 53, 2029–2039.

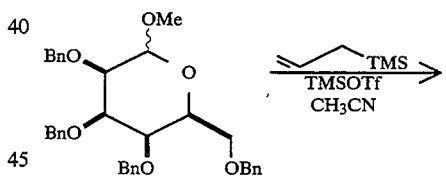

To a stirred solution of the methyl taloside (20.00 g, 36.1 mmol) in acetonitrile (220 mL) at 0° C. under argon was added allyltrimethylsilane (23 mL, 145 mmol) followed by trimethylsilyl trifluoromethanesulfonate (7.1 mL, 37 mmol) dropwise. The resulting clear, yellow solution was stirred at 0° C. for l0 min, then allowed to warm to room temperature. After l h, TLC showed no remaining starting material. The reaction mixture was diluted with diethyl ether (400 mL) and washed with saturated aqueous NaHCO3 (2×200 mL), H₂O (200 mL), and brine (200 mL). The organic phase was dried over Na₂SO₄, filtered, concentrated, and the residue was chromatographed (SiO₂, hexanes-ethyle acetate;

7:1) to give the major allylated product as a clear, colorless oil: 16.207 g (28.74 mmol, 80% yield).

IR (film): 3064 cm$^{-1}$, 3030, 2898, 1453, 1093, 1074, 913, 734, 696.

$^1$H NMR (CDCl$_3$): δ 2.23 (1H, dt, J=7.7, 14.3 Hz), 2.59 (1H, m), 3.13 (1H, dd, J=2.6, 9.4 Hz), 3.60 (1H, dd, J=2.3, 6.3 Hz), 3.81 (1H, dd, J=1.8, 12.0 Hz), 3.92 (1H, m), 4.12 (1H, t, J=2.3 Hz), 4.17 (1H, dd, J=8.8, 12.0 Hz), 4.31 (1H, m), 4.37 (1H, d, J=11.5 Hz), 4.51 (1H, d, J=11.5 Hz), 4.53–4.61 (4H, m), 4.69–4.77 (2H, m), 5.06 (1H, dd, J=0.8, 10.1 Hz), 5.10 (1H, dd, J=0.8, 17.2 Hz), 5.89 (1H, m), 7.20–7.42 (20H, m).

$^{13}$C NMR (CDCl$_3$): 35.72 ppm, 66.31, 67.33, 71.00, 71.28, 73.11, 73.91, 75.06, 76.87, 78.01, 116.90, 127.32, 127.40, 127.71, 127.75, 127.78, 127.84, 128.15, 128.28, 128.39, 128.42, 134.89, 137.82, 138.01, 138.72, 138.81.

[α]$_D$: −24.8° (c 0.81, CHCl$_3$).

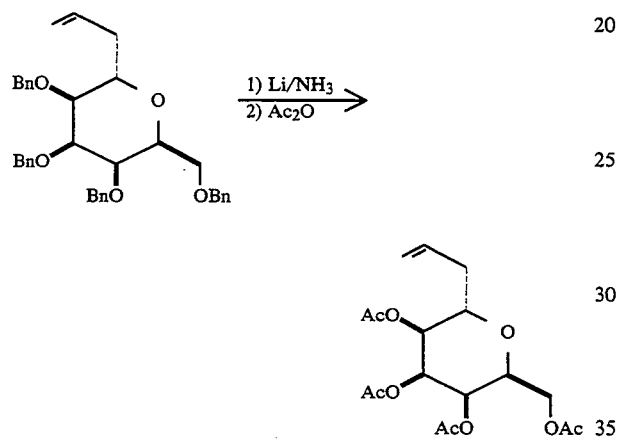

Lithium (4.5 g, 652 mmol) was added piece-wise to liquid NH$_3$ (1 L) at −78° C. under nitrogen, The resulting blue solution was allowed to stir for 20 min before a solution of 10 (32.07 g, 56.86 mmol) in THF (200 mL) was added via cannula. The resulting blue solution was stirred at −78° C. for 30 min, then anhydrous methanol was added dropwise just until the blue color disappeared. The cooling bath was removed and the solvents were evaporated under a stream of nitrogen. The residue was suspended in CH$_2$Cl$_2$ (500 mL) and cooled to 0° C. under nitrogen. To the stirred suspension were added triethylamine (178.4 mL, 1.28 mmol), acetic anhydride ((50 mL, 540 mmol), and N,N-dimethylaminopyridine (1.2 g). The resulting mixture was allowed to warm to room temperature and stir for 12 h. The mixture was washed with H$_2$O (2×500 mL) and brine (500 mL), dried over Na$_2$SO$_4$, filtered, and concentrated. The residue was chromatographed on silica gel to give the tetraacetate as a clear oil: 19.34 g (51.9 mmol, 91.4% yield over two steps).

IR (film): 3077 cm$^{-1}$, 2941, 1749, 1643, 1497, 1434, 1372, 1226, 1116, 1074, 1043, 915.

$^1$H NMR (CDCl$_3$): δ 2.03 (3H, s), 2.06 (3H, s), 2.07 (3H, s), 2.10 (3H, s), 2.27–2.38 (2H, m), 4.02 (1H, ddd, J=4.5, 7.5, 7.5 Hz), 4.10 (1H, dd, J=3.6, 12.2 Hz), 4.20 (1H, ddd, J=3.6, 5.1, 8.9 Hz), 4.63 (1H, dd, J=8.9, 12.2 Hz), 4.84 (1H, dd, J=3.2, 7.3 Hz), 5.08 (1H, t, J=1.3 Hz), 5.11 (1H, m), 5.19 (1H, dd, J=3.2, 5.1 Hz), 5.45 (1H, t, J=3.2 Hz), 5.78 (1H, m).

$^{13}$C NMR (CDCl$_3$): 20.60 ppm, 20.78, 34.75, 60.47, 66.54, 67.27, 68.82, 69.32, 70.61, 117.79, 132.96, 169.47, 169.58, 169.73, 170.77.

MS (FAB): 374 amu (rel. intensity 12%), 373 (M++H, 91), 331 (9), 313 (38), 271 (7), 154 (76), 136 (78), 91 (98), 77 (100), 63 (70), 51 (97).

[α]$_D$: −31.6° (C 0.93, CHCl$_3$).

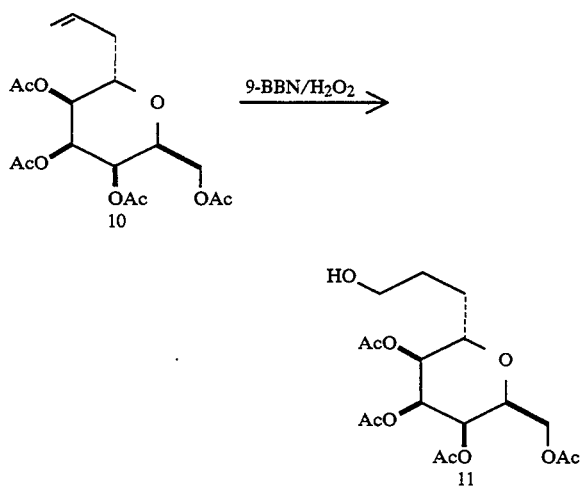

To a stirred solution of the alkene (20.30 g, 54.55 mol) in THF (200 mL) at 0° C. and under argon was added a 0.5M solution of 9-BBN in THF (185 mL, 92.5 mmol). The resulting solution was allowed to warm to room temperature and stir for 3 h, at which point TLC showed no starting material. The reaction mixture was cooled to 0° C. and 10% aqueous NaOH (25 mL) and 30% aqueous H$_2$O$_2$ (25 mL) were sequentially added dropwise. The resulting mixture was stirred at 0° C. for 1.5 h before saturated aqueous NH$_4$Cl (1 L) was added and the mixture was extracted with ethyl acetate (500 mL). The ethyl acetate phase was washed with saturated aqueous NaCl (500 mL), and the combined aqueous phases were extracted with additional ethyl acetate (2×500 mL). The combined ethyl acetate extracts were dried over Na$_2$SO$_4$, filtered, concentrated, and chromatographed (SiO$_2$, hexanes-ethyl acetate, 1:2→0:1) to give the primary alcohol 11 (16.102 g, 41.25 mmol, 75.6% yield) as a clear oil. (CJF-3-13).

IR (film): 3510 cm$^{-1}$, 3020, 3012, 2940, 2877, 1745, 1451, 1432, 1402, 1371, 1227, 1118, 1091, 1046, 991, 965.

$^1$H NMR (CDCl$_3$): δ 1.53–1.72 (4H, m), 2.05 (3H, s), 2.08 (6H, s), 2.10 (3H, s), 3.63 (2H, bt), 3.96 (1H, m), 4.08 (1H, dd, J=3.6, 12.2 Hz), 4.19 (1H, ddd, J=3.6, 5.0, 8.9 Hz), 4.63 (1H, dd, J=8.9, 12.2 Hz), 4.80 (1H, dd, J=3.2, 7.1 Hz), 5.19 (1H, dd, J=3.2, 5.0 Hz), 5.43 (1H, t, J=3.2 Hz).

$^{13}$C NMR (CDCl$_3$): 20.53 ppm, 20.67, 20.71, 26.87, 28.40, 60.53, 62.26, 66.64, 67.33, 69.57, 69.99, 70.59, 169.41, 169.65, 170.74.

α]$_D$: −39.6° (c 9.59, CHCl$_3$).

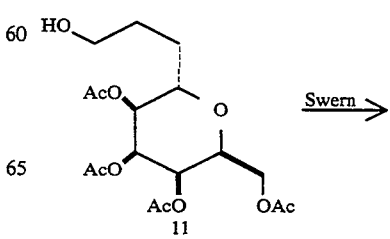

-continued

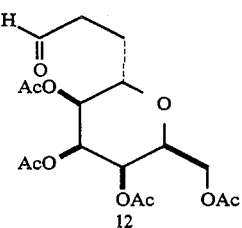
12

To a solution of oxallyl chloride (483 μL, 5.55 mmol) in CH$_2$Cl$_2$ (20 mL) at −78° C. under argon was added DMSO (872 μL, 12.3 mmol) dropwise. The resulting solution was stirred for 15 min at −78° C. before a solution of the alcohol 11 (1.015 g, 2.60 mmol) in CH$_2$Cl$_2$ (10 mL) was slowly added. After 1 h at −78° C., triethylamine (2.00 mL) was added and the resulting clear solution was stirred for an additional 20 min at −78° C. then allowed to warm to room temperature. The reaction mixture was washed with saturated aqueous NH$_4$Cl (30 mL), diluted with diethyl ether (50 mL), and washed with H$_2$O and saturated aqueous NaCl (50 mL ea.). The combined aqueous washes were back-extracted with diethyl ether (50 mL) and the combined organic phases were dried over Na$_2$SO$_4$, filtered, and concentrated, This material was used directly without further purification.

IR (film): 2939 cm$^{-1}$, 2851, 2731, 1748, 1653, 1617, 1576, 1559, 1539, 1521, 1507, 1436, 1372, 1227, 1119, 1074, 1044, 964, 908.

$^1$H NMR (CDCl$_3$): δ 1.68 (1H, m), 1.87 (1H, m), 1.95 (3H, s), 1.97 (3H, s), 2.00 (3H, s), 2.03 (3H, s), 2.45 (2H, m), 3.86 (1H, m), 3.93 (1H, dd, J=3.1, 13.1 Hz), 4.09 (1H, m), 4.68 (1H, dd, J=9.7, 13.1 Hz), 4.69 (1H, m), 5.08 (1H, dd, J=3.1, 5.8 Hz), 5.41 (1H, dd, J=3.0, 3.1 Hz), 9.67 (1H, s).

$^{13}$C NMR (CDCl$_3$): 20.52 ppm, 20.60, 20.75, 23.32, 39.37, 59.96, 66.75, 67.52, 67.92, 69.53, 71.31, 169.24, 169.50, 169.61, 170.75, 201.16.

[α]$_D$: −45.9° (C 8.37, CHCl$_3$).

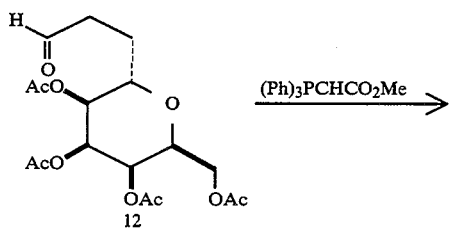

To a stirred solution of the aldehyde 12 (16.23 g, 42 mmol) in CH$_2$Cl$_2$ (400 mL) at 0° C. was added carbomethoxymethylene triphenylphosphorane (27.8 g, 83.2 mmol). The resulting solution was allowed to stir at 0° C. for ca. 1 h, then allowed to warm to room temperature and stir for 18.5 h before being washed with saturated aqueous NH$_4$Cl, H$_2$O, and saturated aqueous NaCl (200 mL ea.). The organic phase was dried over Na$_2$SO$_4$, filtered, and concentrated, and the residue was chromatographed (SiO$_2$, hexanes-ethyl acetate, 2:1) to give 13 (16.524 g, 37.138 mmol, 88% yield) as a clear oil.

IR (film): 2953 cm$^{-1}$, 1750, 1658, 1437, 1373, 1321, 1225, 1170, 1117, 1073, 1042, 908.

$^1$H NMR (CDCl$_3$): δ 1.59–1.73 (2H, m), 2.03 (3H, s), 2.06 (3H, s), 2.08 (3H, s), 2.11 (3H, s), 2.23–2.40 (2H, m), 3.72 (3H, s), 3.91 (1H, ddd, J=3.3, 7.8, 9.5 Hz), 4.11 (1H, dd, J=3.1, 12.3 Hz), 4.18 (1H, ddd, J=3.1, 5.4, 9.2 Hz), 4.63 (1H, dd, J=9.2, 12.3 Hz), 4.77 (1H, dd, J=3.1, 7.8 Hz), 5.18 (1H, dd, J=3.1, 5.4 Hz), 5.46 (1H, t, J=3.1 Hz), 5.85 (1H, d, J=15.6 Hz), 6.94 (1H, m).

$^{13}$C NMR (CDCl$_3$): 20.57 ppm, 20.65, 20.78, 27.58, 28.93, 51.39, 60.31, 66.68, 67.43, 68.26, 69.47, 70.94, 121.79, 147.87, 166.85, 169.35, 169.54, 169.67, 170.71.

[α]$_D$: −23.7° (C 1.41 CHCl$_3$).

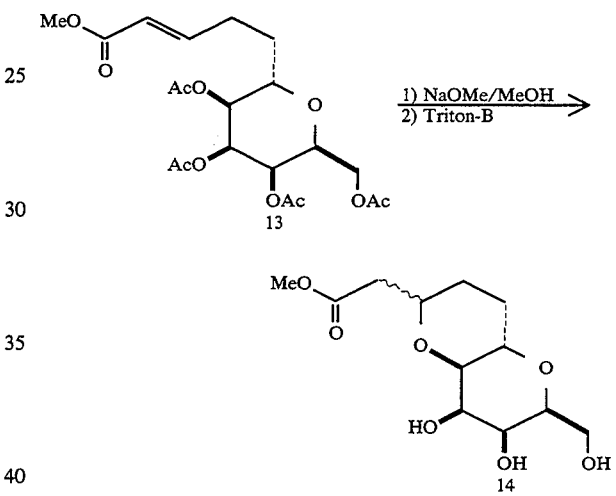

C1-C11 triol

Anhydrous methyl acetate (25 mL) was added to a solution of sodium methoxide in methanol (prepared from 8 g Na in 500 mL MeOH), and the resulting solution was added via cannula to a stirred solution of the tetraacetate (C]F-3-15, 13) (16.2 g, 36.4 mmol) in methanol (250 mL) and methyl acetate (25 mL) at 0° C. The resulting solution was stirred at 0° C. for 30 min before a solution of triton B (10 mL of a 40% solution in methanol) was added. The resulting yellow solution was stirred at 0° C. for 1 h, then allowed to warm to room temperature with stirring. Solid NH$_4$Cl (20 g) was added and the solvents were removed in vacuo. The residue was suspended in methyl acetate (200 mL) and filtered through a fritted glass funnel. The solids were washed with additional methyl acetate (2×100 mL) and the combined filtrate and washes were concentrated to a yellow oil. Column chromatography on SiO$_2$ (methyl acetate to ethyl acetate/methanol, 10:1) gave the triol 14 as a clear, pale yellow oil and an approximate 2.5:1 mixture of C3 diastereomers: 7.26 g (26.3 mmol, yield).

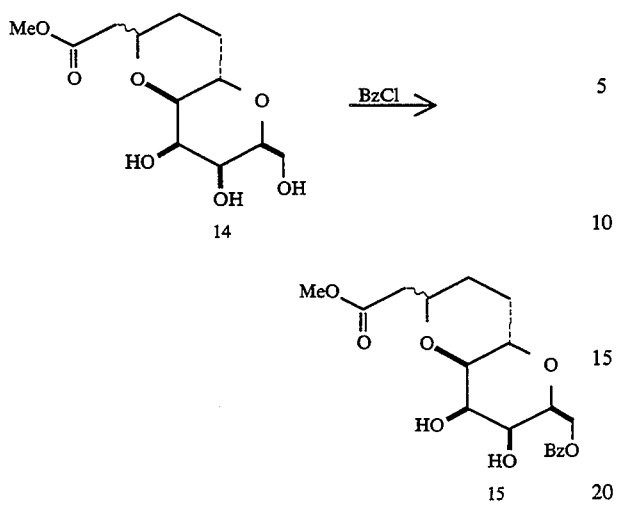

C11 Benzoate

To a stirred solution of the triol (17 mg, 61 μmol) in CH₂Cl₂ (1.0 mL) at 0° C. and under N₂ was added pyridine (100 μL, 1.24 mmol) followed by benzoyl chloride (50 μL, 431 μmol). TLC (ethyl acetate) showed no remaining starting material after 10 min. The reaction solution was diluted with diethyl ether (2 mL) and washed with H₂O and brine. The organic phase was dried over Na₂SO₄, filtered, concentrated, and chromatographed (SiO₂, ethyl acetate) to give the primary benzoate as a clear oil: 21 mg (55 μmol, 89% yield).

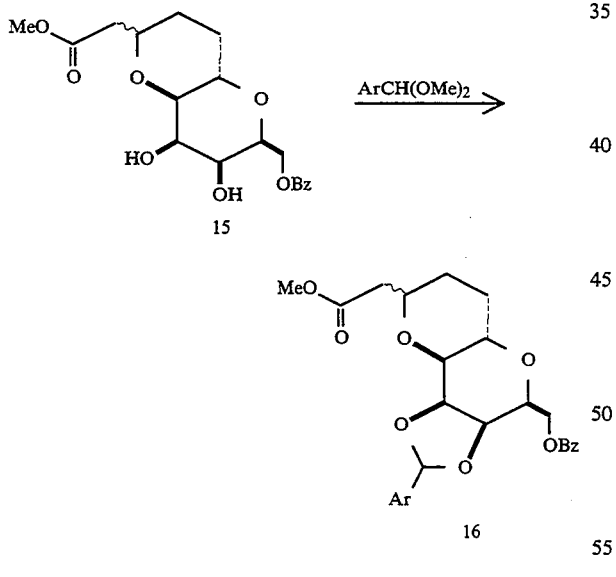

C8-C9 Anisylidene

To a stirred solution of the diol (436 mg, 1.13 mmol) in benzene (20 mL) at room temperature was added anisaldehyde dimethyl acetal (412 μL, 2.4 mmol) followed by pyridinium p-toluene sulfonate (10 mg). The resulting solution was stirred at room temperature. After 30 min, crushed 4Å molecular sieves (0.5 g) were added and stirring was continued. Solid NaHCO₃ (1 g) was added after 6 h and the resulting mixture was filtered through Celite with diethyl ether washes. The filtrate was concentrated and the residue was purified by SiO₂ column chromatography (1:1 hexanes/ethyl acetate to 10:1 ethyl acetate/methanol) to give the anisylidene (356 mg, 714 μmol, 62% yield) as a clear, colorless oil, and recovered diol (157 mg, 415 μmol).

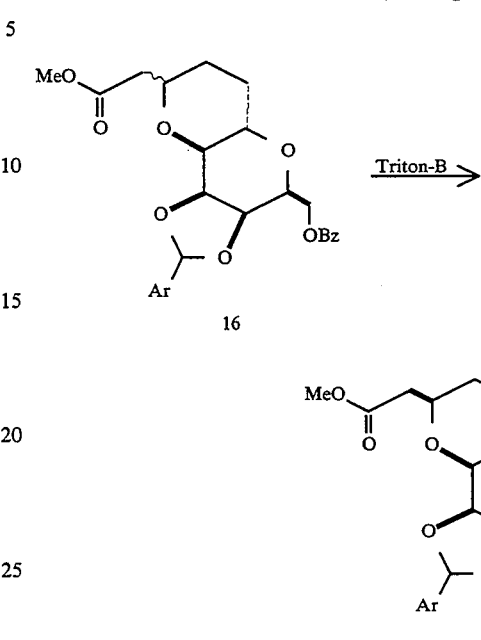

C3 Equilibration

To a stirred solution of the C3 epimers (356 mg, 714 μmol) in benzene (30 mL) at room temperature was added methyl acetate (100 μL) followed by a solution of triton B (30 μL of 40% solution in methanol). The resultant pale yellow solution was stirred at room temperature for 10 min before saturated aqueous NH₄Cl (20 mL) and diethyl ether (30 mL) were added. The separated organic phase was washed with H₂O and brine (30 mL, ea), dried over Na₂SO₄, filtered, and concentrated to an oil: 1H NMR analysis of the crude product showed only one isomer. This material was used without further purification.

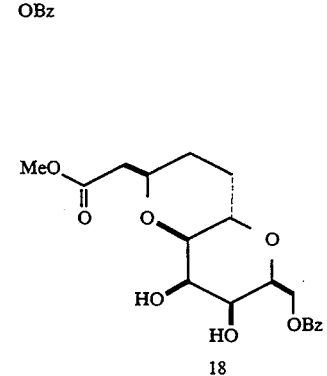

C8-C9 Ciol/C11 Benzoate

To a stirred solution of the anisylidine (3.37 g, 6.74 mmol) in methanol (150 mL) at room temperature was added pyridinium p-toluene sulfonate (PPTS, 50 mg). After stirring at room temperature for 13 h, additional PPTS (50 mg) was added. After a total of 15 h, TLC (1:1:1 hexanes/ethyl acetate/CHCl₃) showed no remaining starting material. Solid NaHCO₃ (250 mg) and pyridine (250 μL) were added and the mixture was concentrated. The residue was suspended in ethyl acetate, filtered, concentrated, and chromatographed (SiO₂, ethyl acetate) to give the diol as a colorless oil: 2.53 g (6.65 mmol, 99% yield).

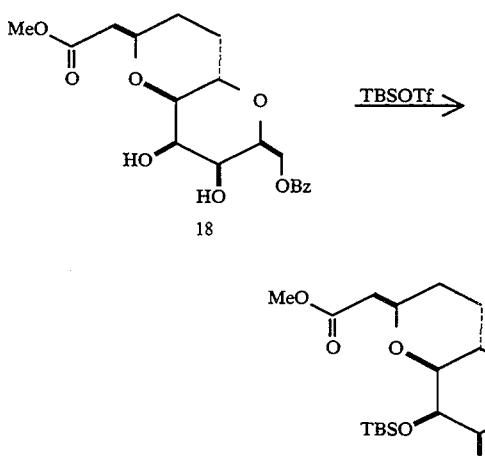

C8-C9 diTBS/C11 Benzoate

To a stirred solution of the diol (2.53 g, 6.65 mmol) in CH₂Cl₂ (200 mL) at 0° C. and under argon was added triethylamine (7.81 mL, 56 mmol), followed by tert-butyldimethylsilyl trifluoromethane sulfonate (6.43 mL, 28 mmol). The resulting solution was allowed to slowly warm to room temperature and stir over 14 h. TLC (3:1:1 hexanes/ethyl acetate/CHCl₃) showed one spot (R$_f$ ca. 0.85). The reaction solution was diluted with diethyl ether (300 mL) and washed with saturated aqueous NH₄Cl, H₂O, and brine (200 mL ea.). The organic phase was dried over Na₂SO₄, filtered and concentrated. Silica gel column chromatography (8:1 hexanes/ethyl acetate) and vacuum-line concentration overnight gave the disilyl ether as a clear, colorless oil: 3.897 g (6.41 mmol, 96% yield).

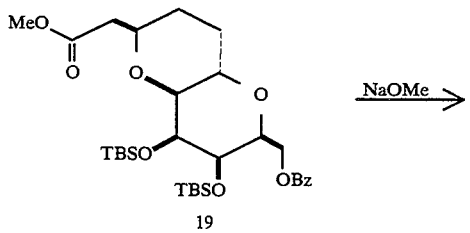

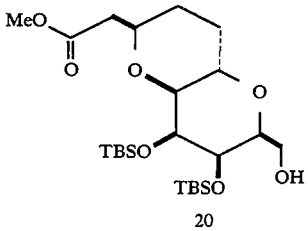

C11 Alcohol

To a stirred solution of the primary benzoate (3.89 g, 6.40 mmol) in methanol (150 mL) and methyl acetate (6 mL) at 0° C. was added a solution of sodium methoxide in methanol (prepared from 0.5 g Na in 50 mL methanol). After stirring at 0° C. for 30 min, the cooling bath was removed, and after a total of 280 min, TLC (3:1:1 hexanes/ethyl acetate/CHCl₃) showed no remaining starting material. Solid NH₄Cl (2 g) was added and the resulting white suspension was concentrated in vacuo. The residue was suspended in diethyl ether (200 mL) and washed with H₂O (2×100 mL) and brine (100 mL). The organic phase was dried over Na₂SO₄, filtered and concentrated. Silica gel column chromatography (4:1 hexanes/ethyl acetate) gave the primary alcohol, as a crystalline solid: 2.906 g (5.74 mmol, 90% yield).

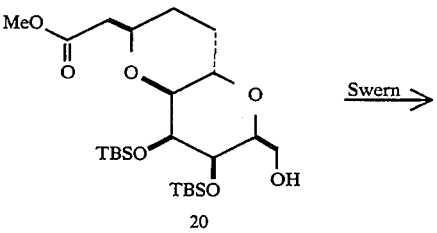

C11 aldehyde:

Dimethyl sulfoxide (963 μL, 13.58 mmol) was added dropwise to a stirred solution of oxallyl chloride (533 μL, 6.126 mmol) in CH₂Cl₂ (20 mL) at −78° C. under argon. After stirring for 20 min at −78° C., a solution of the alcohol (636 mg, 1.26 mmol) in CH₂Cl₂ (10.0 mL) was slowly added. After stirring for 1 h at −78° C., triethylamine (2.21 mL) was added, the cooling bath was removed, and the mixture stirred for an additional 30 min. Saturated aqueous NH₄Cl (50 mL) and diethyl ether (50 mL) were added, and the separated organic phase was washed with H₂O (2×50 mL) and brine (50 mL). Drying over Na₂SO₄, filtration, concentration, and silica gel column chromatography gave the aldehyde as a clear oil: 551 mg (1.10 mmol, 87% yield).

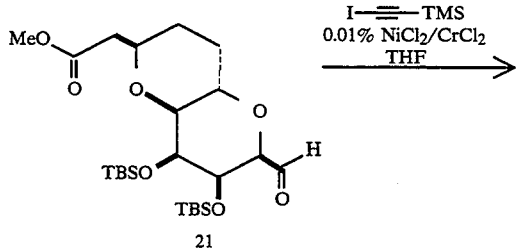

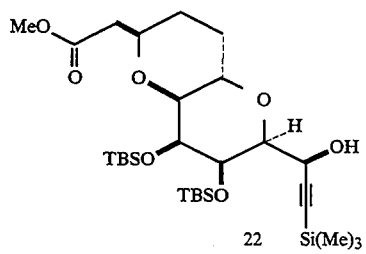

TMS Acetylene Addition

To a stirred solution of the aldehyde (551 mg, 1.10 mmol) and iodotrimethylsilylacetylene* (1.25 g, 5.6 mmol) in THF under $N_2$ and at room temperature was added 0.01% $NiCl_2/CrCl_2$ (ca. 200 mg). Additional 0.01% $NiCl_2/CrCl_2$ was added after 10.5 h (ca. 100 mg), and after 16 h (ca. 250 mg). After 31 h total, the reaction mixture was diluted with saturated aqueous $NH_4Cl$ (5 mL) and extracted with ethyl acetate (4×4 mL). The L combined ethyl acetate extracts were washed with $H_2O$ (2×10 mL) and brine (5 mL), dried over $Na_2SO_4$, filtered, and concentrated. Silica gel column chromatography (8:1 hexanes/ethyl acetate) gave the higher $R_f$ major C11 diastereomer (529 mg, 882 μmol, 80%) and a mixture (109 mg) of the lower $R_f$ undesired C11 diasteromer and starting aldehyde. $^1H$ NMR of the crude product mixture before chromatography showed an approximate 10:1 ratio of diastereomeric adducts.

*Reference to 1-iodo-2-trimethylsilylethyne: A. Commercon, et al. Tetrahedron. 1980, 36, 1215.

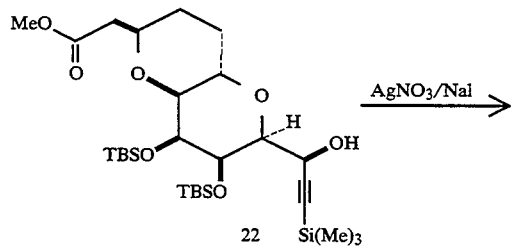

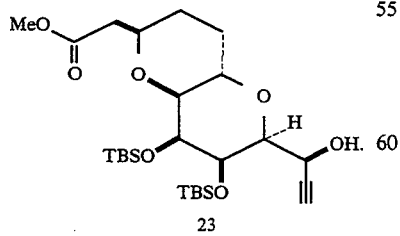

To a stirred solution of 22 (241 mg, 402 μmol) in ethanol-$H_2O$ (5 mL, 4:1 v/v) at 0° C. was added a solution of $AgNO_3$ (138 mg, 804 μmol) in ethanol-$H_2O$ (0.5 mL, 3:1 v/v). The resulting suspension was stirred at 0° C. for 20 min (TLC showed no 22). A solution of NaI (240 mg, 1.608 mmol) in $H_2O$ (0.5 mL) was added dropwise, and stirring was continued at 0° C. for an additional 30 min. The yellow suspension was diluted with diethyl ether (10 mL) and filtered through celite along with additional ether washes (4×10 mL). The combined filtrate and washes were concentrated by rotary evaporation to an aqueous suspension that was extracted with diethyl ether (4×5 mL). The combined organic extract was dried over $Na_2SO_4$, filtered, and concentrated. Silica gel column chromatography gave 23 (206 mg, 390 μmol, 97% yield) as a crystalline solid.

[after: Tetrahedron Lett. 1987, 28, 3923-3926.]

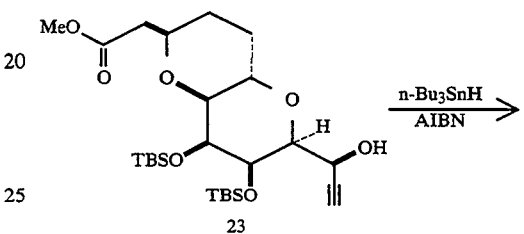

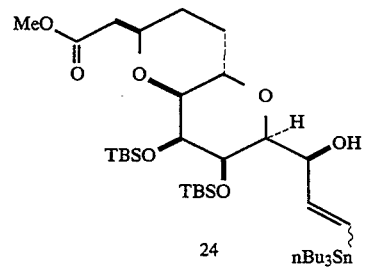

A stirred solution of 23 (52 mg, 98.5 μmol), tri-n-butylstannane (134 μL, 493 μmol), and AIBN (2 mg) in de-gassed toluene under argon was placed in a preheated oil bath at 80° C. After 30 min, TLC (5:1:1 hexanes/ethyl acetate/$CHCl_3$) showed complete conversion to two higher $R_f$ spots. The reaction mixture was cooled to room temperature, concentrated in vacuo, and the residue was chromatographed (SiO_2, hexanes→ hexanes-ethyl acetate, 5:1) to give the higher $R_f$ E-vinyl stannane (58 mg, 71 μmol, 72% yield) and lower $R_f$ Z-vinyl stannane (18 mg, 22 μmol, 22% yield) as clear, colorless oils.

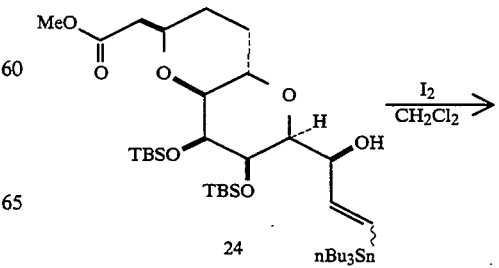

51

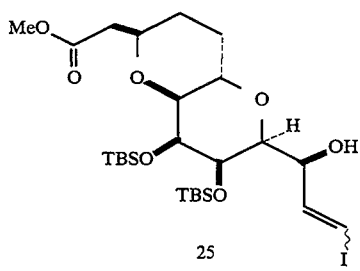

25

To a stirred solution of the E-vinyl stannane 24 (58 mg, 70 μmol) in CH$_2$Cl$_2$ (1 mL) at 0° C. was added a solution of 12 in CH$_2$Cl$_2$ (ca. 360 μL, of a 50 mg I2/mL CH$_2$Cl$_2$ solution, ca. 71 μmol) just until the reaction mixture remained faint pink. After an additional 30 min at 0° C., TLC (5:1:1 hexanes/ethyl acetate/CHCl$_3$) showed complete conversion to a higher R$_f$ spot. The solution was diluted with diethyl ether (2 mL) and washed with aqueous 10% Na$_2$S$_2$O$_3$ (2×1 mL), H$_2$O, and brine (1 mL ea). The organic phase was dried over Na$_2$SO$_4$, filtered, and concentrated. Purification of the residue by silica gel column chromatography (hexanes-ethyl acetate, 4:1) gave the E-vinyl iodide as a clear, colorless oil: 46 mg (70 μmol, ca. 100% yield).

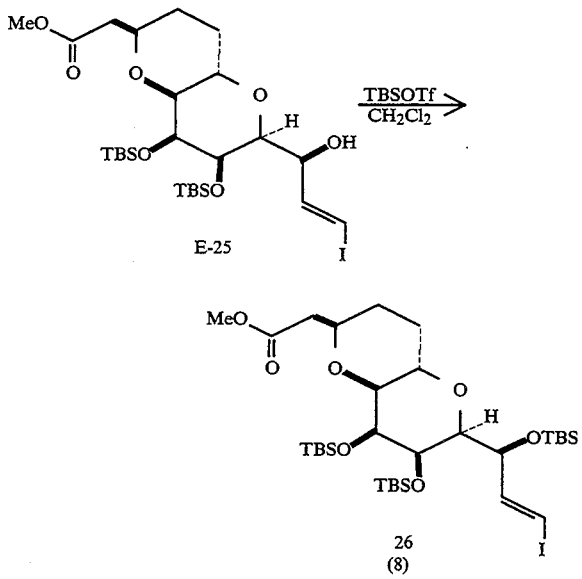

To a stirred solution of (42 mg, 64 μmol) in CH$_2$Cl$_2$ (2 mL) at 0° C. under argon was added triethylaxnine (179 μL, 1.28 mmol) followed by tert-butyldimethylsilyltrifluoromethane sulfonate (149 μL, 640 μmol). The cooling bath was removed and the reaction mixture was allowed to warm to room temperature and stir for 3 h. TLC (5:1:1 hexanes/ethyl acetate/CHCl$_3$) at this time showed no remaining starting material. The reaction solution was diluted with diethyl ether (5 mL) and washed with saturated aqueous NaHCO$_3$ (5 mL), H$_2$O (5 mL), and brine (2 mL). Drying over Na$_2$SO$_4$, filtration, concentration, and SiO$_2$ column chromatography (hexanes-ethyl acetate, 5:1) gave as a clear, colorless oil: 49 mg, 63 μmol, 99% yield).

52

COMPOUND 9

Compound 9 was prepared from compounds 7 and 8, as follows.

C-14 Aldehyde

To a stirred solution of the C14 alcohols derived from compound 7, (46.9 mg, 53.8 μmole) in CH$_2$Cl$_2$ (4 mL) was added solid NaHCO$_3$ (50 mL) followed by the Dess-Martin periodinane reagent (45.6 mg, 10g μmole). TLC (3:1:1 hexanes/ethyl acetate/CHCl$_3$) showed no remaining starting material after 1 h. The reaction mixture was diluted with diethyl ether (16 mL) and washed for 20 min with an aqueous solution saturated with NaHCO$_3$ and containing 10% Na$_2$S$_2$O$_3$ by wt. The separated organic phase was washed with additional aqueous NaHCO$_3$/Na$_2$S$_2$O$_3$ for 10 min, H$_2$O, and brine (10 mL, ea.). The organic phase was dried over Na$_2$SO$_4$, filtered, and concentrated. The residue was filtered through a short pad of SiO$_2$ (1:1 hexanes/ethyl acetate), and the filtrate was concentrated to afford the C27 epimeric aldehydes (44 mg, 51 μmole, 94% yield) as a clear, colorless oil.

C13-C14 Coupling

To a stirred solution of the aldehyde (62 mg, 71 μmole) and the vinyl iodide (comp 8) (179 mg, 214 μmole) in DMF (2 mL) under nitrogen was added 0.1% NiCl$_2$/CrCl$_2$ (ca. 200 mg). The resulting green mixture was stirred at room temperature. After 14 h, TLC (3:1:1 hexanes/ethyl acetate/CHCl$_3$) showed approximately 50% conversion, and additional 0.1% NiCl$_2$/CrCl$_2$ (ca. 200 mg) was added. After a total of 39 h, TLC showed no remaining aldehyde. The reaction mixture was diluted with saturated aqueous NH$_4$Cl (12 mL) and H$_2$O (2 mL) and extracted with ethyl acetate (4×10 mL). The combined extracts were washed with H$_2$O (2×10 mL) and brine (10 mL), dried over Na$_2$SO$_4$, filtered, and concentrated. The residue was purified by SiO$_2$ column chromatography to give the coupled allylic alcohol (79.1 mg, 56.7 μmole, 80% yield) as a colorless foam. (CJF3-279)

C14 ketone

To a stirred solution of the allylic alcohols (CJF-3-279) (59 mg, 39 μmole) in CH$_2$Cl$_2$ (2 mL) was added solid NaHCO$_3$ (50 mg) followed by the Dess-Martin periodinane reagent (66 mg, 156 μmole). Additional Dess-Martin reagent (33 mg, 78 μmole) and NaHCO$_3$ (50 mg) were added after 1 h. After a total of 90 min, the reaction mixture was diluted with diethyl ether (16 mL) and washed with an aqueous solution saturated with NaHCO$_3$ and containing 10% Na$_2$S$_2$O$_3$ by wt for 20 min. The separated organic phase was washed with additional aqueous NaHCO$_3$/Na$_2$S$_2$O$_3$ for 10 min, H$_2$O, and brine (10 mL ea.). The organic phase was dried over Na$_2$SO$_4$, filtered, and concentrated. The residue was purified by SiO$_2$ column chromatography followed by PTLC (5:1:1 hexanes/ethyl acetate/CHCl$_3$) to give the enone (50.1 mg, 33 μmole, 85% yield) as a clear, colorless oil. (CJF-3-280)

C30 Alcohol

To a stirred mixture of the C30 MPM ether (CJF-3-280, mixture of C27 epimers) (50 mg, 33 μmole) in CH$_2$Cl$_2$ (2.00 mL), aqueous phosphate buffer (200 μL, pH 7.00), and tert-butanol (20 μL) was added DDQ (15.0 mg, 66 μmole). The reaction flask containing the resulting mixture was immersed in a sonication bath (H₂O, room temperature) and sonicated for 30 sec, removed from the bath and stirred without sonication for approximately 3–5 min, and sonicated for an additional 30 sec. At this point, HPTLC (3:1:1 hexanes/ethyl acetate/tert-butyl methyl ether) showed approximately 50% conversion. Additional DDQ (15.0 mg) was added and the mixture was sonicated for an additional 2×30 sec and stirred for a total of 20 min. TLC showed no remaining starting material. The reaction mixture was washed with saturated aqueous NaHCO₃ (2×2 mL) and H₂O (2 mL). The combined aqueous phases were extracted with CH₂Cl₂ (2×1 mL), and the combined organic fractions were washed with brine (2 mL), dried over Na₂SO₄, filtered, and concentrated. The residue was purified by PTLC (3:1:1 hexanes/ethyl acetate/tert-butyl methyl ether, 2 elutions) to afford the higher $R_f$ desired C27 epimer (31.4 mg, 22.5 μmole, 66% yield), (CJF-3-281A) and the lower $R_f$ undesired C27 epimer (6.4 mg, 14% yield) (CJF-3-281B) as clear, colorless oils.

C1-Carboxylic Acid

To a stirred solution of the methyl ester (CJF-3-281A) (31.4 mg, 22.5 gmole) in THF (2.00 mL) at room temperature was added 1M aqueous LiOH (666 μL). The resulting mixture was stirred at room temperature for 36 h, at which time TLC (ethyl acetate) showed only a trace of starting material. The THF was removed by rotary evaporation at room temperature, and the resulting aqueous suspension was diluted with H₂O (2 mL), cooled to 0° C., and with rapid stirring was carefully acidified to ca. pH 3 with 0.5M aqueous HCl. The aqueous mixture was extracted with diethyl ether (5×2 mL), and the combined extracts were washed with H₂O and brine (2 mL ea.). The ether phase was dried over Na₂SO₄, filtered, and concentrated. The residue was chromatographed on a short column (ca. 2 cm) of SiO₂ (ethyl acetate) to give the caxboxylic acid (29.7 mg, 21.5 μmole, 96% yield) as a colorless foam. (CJF-3-282)

Lactone 9

To a stirred solution of the C30 hydroxy-C1 carboxylic acid (29.7 mg, 21.5 μmole) in THF (225 μL) at room temperature under argon was added triethylamine (7.5 μL, 54 μmole), followed by 2,4,6-trichlorobenzoyl chloride (4.2 μL, 27 μmole). The resulting mixture was stirred at room temperature for 2 h, then filtered through a fritted glass filter along with dry toluene washes under argon. The combined filtrate and washes were diluted to 11.25 mL with dry toluene, and the resulting clear, colorless solution was added via syringe pump over 14 h to a stirred 70° C. solution of N,N-dimethylaminopyridine (16.5 mg, 135 μmole)in toluene (10 mL) under argon. The syringe was rinsed with dry toluene (2×0.5 mL) and the rinses were added to the reaction solution. After an additional 2 h (16 h total), the reaction solution was cooled to room temperature, diluted with diethyl ether (20 mL), and washed with 0.5M aqueous HCl (2×5 mL), H₂O, and brine (5 mL ca.). The combined aqueous fractions were extracted with diethyl ether (2×5 mL) and the combined organic phases were dried over Na₂SO₄, filtered, and concentrated. The residue was purified by PTLC (5:1 hexanes/ethyl acetate) to afford the lactone (23.3 mg, 81% yield) as a clear, colorless oil. (CJF-3-283)

COMPOUND 10

Compound 10 was synthesized from compound 9 by the following procedure.

To a stirred solution of compound 9 (35.7 mg, 26.2 μmole) in THF (2.62 mL) and anhydrous methyl acetate (262 μL) was added an approximate 1M solution of tetrabutylammonium fluoride (TBAF) in THF (79 μL, pH ca. 6.8). After stirring at room temperature for 36 h, TLC (10:1 ethyl acetate/methanol) showed complete desilylation. The reaction solution was filtered through a 2 cm pad of SiO₂ (silica gel 60, 230–400 mesh, ethyl acetate) to remove the TBAF. The filtrate was concentrated and the residue dried on a high vacuum line for ca. 1 h before being used in the next step without further purification. ¹H NMR (C6D6) indicated an approximate 5:1 ratio of diastereomerie Michael-type adducts.

The above product mixture was dissolved in CH₂Cl₂ (2.0 mL) at room temperature, and to the stirred solution was added pyridinium p-toluenesulfonate (2 mg). After stirring at room temperature for 18 h, TLC (10:1 ethyl acetate/methanol) showed complete conversion to the desired higher $R_f$ polycyclic ketal and a minor lower $R_f$ by-product. The reaction t solution was filtered directly through a 1 cm pad of SiO₂ with 20:1 ethyl acetate/methanol. The combined filtrate was concentrated and the residue was used without further purification.

To a stirred solution of the crude diol in CH₂Cl₂ (2.0 mL) at room temperature was added pyridine (17 μL, 210 μmole) followed by p-nitrobenzoyl chloride (19.3 mg, 104 μmole). After stirring at room temperature for 16 h, TLC (ethyl acetate) showed no remaining starting material. The solution was concentrated by rotary evaporation and the residue was suspended in diethyl ether (5 mL) and filtered through a short pad of Celite along with additional ether washes. The filtrate was concentrated and the products were separated by PTLC (ethyl acetate) to afford the higher $R_f$ C38 p-nitrobenzoate/C35 alcohol/C14–C18 polycyclic ketal (15.5 mg, 16.7 μmol, 64% yield over 3 steps (CJF-4-16A) and an impure lower $R_f$ C 14 ketone by-product (CJF-4-16B ).

To a stirred solution of CJF-4-16A (15.5 mg, 16.7 μmole) in DMF (675 μL) was added pyridine (45 μL, 556 μmole), followed by tert-butyldimethylsilyl chloride (16.4 mg, 109 μmole) and AgNO₃ (18.8 mg, 111 μmole). The resulting white suspension was stirred in the dark at room temperature for 18 h, at which time TLC showed no remaining starting material. The mixture was diluted with diethyl ether (5 mL) and filtered through Celite along with additional ether washes. The combined filtrate was washed with saturated aqueous NH₄Cl, H₂O, and brine (5 mL ea.), dried over Na₂SO₄, filtered through a short pad of SiO₂ (ethyl acetate), and concentrated. The residue was purified by PTLC (1:1 hexanes/ethyl acetate) to give the secondary silyl ether (16.1 mg, 15.5 μmole, 93% yield) as a clear, colorless oil. (CJF-4-17)

To a stirred solution of CJF-4-17 (16 mg, 15 μmole) in methanol (1 mL) at room temperature was added solid K₂CO₃ (ca. 0.2 mg). The resulting mixture was stirred at room temperature for 2.5 h, at which time TLC showed no remaining starting material. Toluene (1 mL) and acetic acid (5 μL) were added and the methanol was removed by rotary evaporation. The resulting suspension was filtered through a short pad of SiO₂ along with ethyl acetate. The combined filtrate was concentrated and the residue was purified by PTLC (ethyl acetate) to give the primary alcohol (12.8 mg, 14.4 μmole, 93% yield) as a clear, colorless oil. This is compound 10.

COMPOUND 11

Compound 11 was synthesized according to the following procedure.

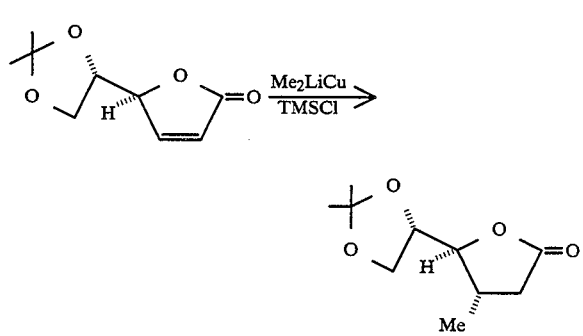

To a flame-dried, nitrogen cooled 250-ml 3-neck flask equipped with a magnetic stirbar and nitrogen inlet was added freshly prepared CuBrDMS complex (5.57 g, 27.2 mmol). The flask was evacuated again and charged with nitrogen. Dry THF (80 mL) was introduced via syringe and t the resulting suspension cooled to −78° C. Methyllithium (Aldrich, 1.45M in ether, 38 mL) was added dropwise via syringe over about 15 min. The yellow suspension eventually became clear and colorless. Freshly distilled TMSCl (6.9 mL, 54.4 mmol) was introduced next dropwise via syringe. The resulting colorless solution was stirred for 5–10 min. The butenolide (2.55 g, 13.9 mmol) was dissolved in 5 mL of dry THF and added dropwise over 10–15 min. The resulting reaction was stirred at −78° C. for 1 h, during which time the color changed from yellow to orange. The cooling bath was removed and mixture stirred at room temperature for 8 h. The dark green reaction was quenched by cautious dropwise addition of 35 mL saturated 10% NH4OH/NH4Cl. The flask was opened to the air and stirred for 12 h. The aqueous layer turned bright blue during this time. The organic layer was decanted and the aqueous layer was extracted with ethyl acetate (3×50 mL). The combined organic layers were washed with saturated ammonium chloride, brine, and dried with sodium sulfate. The solvents were evaporated to give nearly pure product (2.64 g, 13.2 mmol, 95% yield) as an oil. A sample was subjected to silica gel chromatography (65% ether/hexanes) to give analytically pure product.

IR (film): 2985 cm$^{-1}$, 2936, 2887, 1779, 1456, 1419, 1380, 1372, 1257, 1211, 1158, 1128, 1093, 1062, 1025, 987, 966, 948, 914, 870, 827.

$^1$H NMR (CDCl3): δ 1.17 (3 H, d, J=6.9 Hz), 1.36 (3 H, s), 1.38 (3 H, s), 2.11 (1 H, dd, J=5.8, 17.5 Hz), 2.59 (1 H, ddtd, J=4.7, 5.8, 6.9, 8.9 Hz), 2.83 (1 H, dd, J=8.9, 17.5 Hz), 3.92 (1 H, dd, J=7.5, 8.2 Hz), 4.04 (1 H, dd, 2.3, 4.7 Hz), 4.07 (1 H, dd, J=6.9, 8.2 Hz), 4.21 (1 H, ddd, J=2.3, 6.9, 7.5 Hz).

$^{13}$C NMR (CDCl3): δ 19.49, 25.70, 25.89, 32.20, 36.58, 65.48, 76.26, 84.40, 109.99, 176.33.

MS (FAB): 201 amu (M++ H, rel. intensity 25%), 185 (21), 147 (15), 73 (100).

[α]$_D$: +21.5° (C 2.00 CH2Cl2).

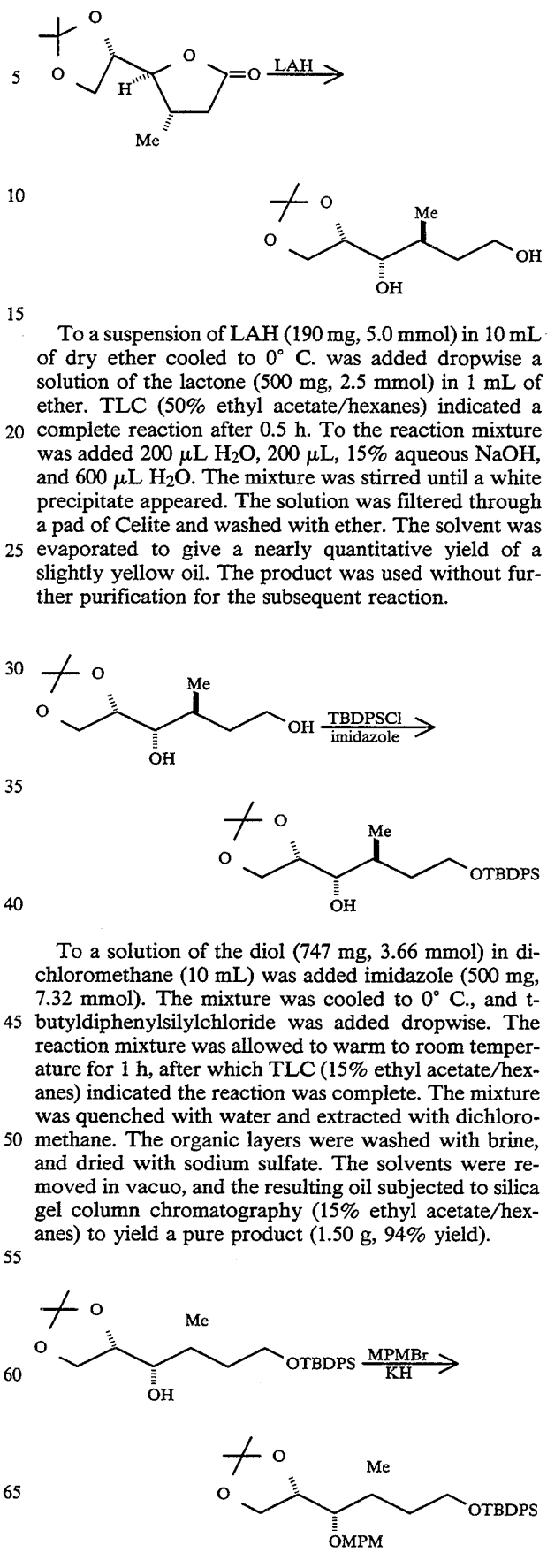

To a suspension of LAH (190 mg, 5.0 mmol) in 10 mL of dry ether cooled to 0° C. was added dropwise a solution of the lactone (500 mg, 2.5 mmol) in 1 mL of ether. TLC (50% ethyl acetate/hexanes) indicated a complete reaction after 0.5 h. To the reaction mixture was added 200 μL H2O, 200 μL, 15% aqueous NaOH, and 600 μL H2O. The mixture was stirred until a white precipitate appeared. The solution was filtered through a pad of Celite and washed with ether. The solvent was evaporated to give a nearly quantitative yield of a slightly yellow oil. The product was used without further purification for the subsequent reaction.

To a solution of the diol (747 mg, 3.66 mmol) in dichloromethane (10 mL) was added imidazole (500 mg, 7.32 mmol). The mixture was cooled to 0° C., and t-butyldiphenylsilylchloride was added dropwise. The reaction mixture was allowed to warm to room temperature for 1 h, after which TLC (15% ethyl acetate/hexanes) indicated the reaction was complete. The mixture was quenched with water and extracted with dichloromethane. The organic layers were washed with brine, and dried with sodium sulfate. The solvents were removed in vacuo, and the resulting oil subjected to silica gel column chromatography (15% ethyl acetate/hexanes) to yield a pure product (1.50 g, 94% yield).

A solution of the alcohol (126 mg, 0.285 mmol) and freshly prepared MPMBr (86 mg, 0.428 mmol) were dissolved in dry THF (15 mL) and cooled to 0° C. To this mixture was added oil-free KH (200 mg, 5.09 mmol) portionwise. The reaction was warmed to room temperature for 1.5 h, then diluted with ether and quenched with saturated ammonium chloride. The organic layer was removed, and the aqueous layer extracted with ether (3×10 mL). The combined organic layers were washed with brine, dried over sodium sulfate, and filtered. The solvents were removed and the viscous oil purified via silical gel column chromatography (10% ethyl acetate/hexanes) to give the product (148 mg, 92% yield).

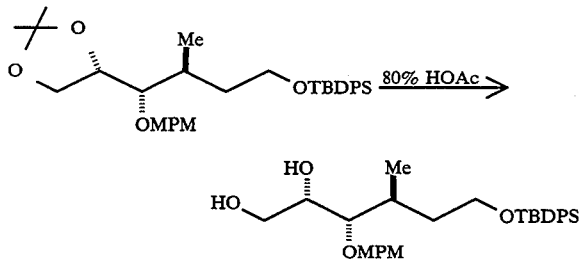

To a solution of the acetonide (7.50 g, xx mmol) in THF (10 mL) was added 80% HOAc (40 mL) at room temperature. The reaction was carefully monitored by TLC (50% ethyl acetate/hexanes). The reaction is generally complete within 4 h. The mixture was diluted with ethyl acetate, and quenched with water. Solid sodium bicarbonate was added to consume the excess acetic acid. The aqueous layer was then extracted with more ethyl acetate. The combined organic layers were dried over magnesium sulfate, and the solvents removed in vacuo to yield the diol (5.6 g, 80% yield) as a viscous oil.

IR (film) 1034 cm$^{-1}$, 1159, 1249, 1514, 1612, 1724, 2961, 3435.

$^1$H NMR (CDCl$_3$, 500 mHz): δ 1.06 (3 H, d, J=6.9 Hz), 1.19 (9 H, s), 1.53 (1 H, m), 1.85 (1 H, m), 1.96 (1 H, m), 2.04 (1 H, m), 2.51 (I H, d, J=6.5 Hz), 3.31 (1 H, m), 3.59 (2 H, m), 3.72 (1 H, m), 3.81 (3 H, s, -OCH$_3$), 4.10 (I H, m), 4.14 (1 H, m), 4.46 (1 H, d, J=10.9 Hz), 4.63 (1 H, d, J=10.9 Hz), 6.89 (2 H, d, J=8.5 Hz), 7.25 (2 H, d, J=8.5 Hz).

HRMS (FAB) calcd for C$_{20}$H$_{32}$O$_6$ (M++ Na) 391.2097, found (M++ Na) 391.2119.

[α]$_D$ −9.2° (c 1.2, MeOH).

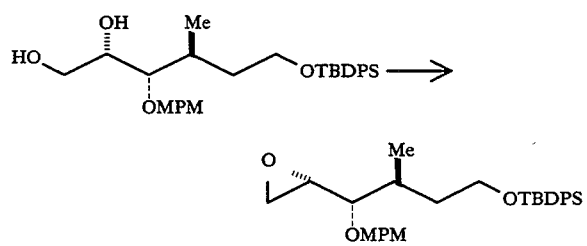

To a suspension of NaH (60 % in oil, 2.33 g, 58 mmol) in THF (300 mL) at room temperature was added a solution of the diol (3.18 g, 6 mmol) in THF (20 mL). After being stirred for 40 min, the mixture was cooled to 0° C. and TsIm (1.49 g, 6.7 mmol) was added portionwise. The mixture was stirred at 4° C. overnight. The reaction was quenched by the addition of water and the organic layer was separated. The aqueous layer was extracted with ether. The organic layer was dried over NaSO$_4$ and the solvents were removed by rotary evaporation. The residue was column chromatographed (Hexane:EtOAc=8:1) to give the epoxide (2.53 g, 83% yield).

\* For better result, slower addition of TsIm as a solution is suggested.

IR (film) 821 cm$^{-1}$, 1159, 1285, 1514, 1613, 1726, 2970.

$^1$H NMR (CDCl$_3$): δ 1.07 (9 H, s, t-Bu), 1.51 (1 H, m), 1.89 (1 H, m), 1.95 (1 H, m), 2.52 (1 H, m), 2.81 (2 H, m), 3.05 (1 H, m), 3.80 (3 H, s), 4.09 (2 H, m), 4.49 (1 H, d, J=11.5 Hz), 4.78 (1 H, d, J=11.5 Hz), 6.87 (2 H, d, J=8.6 Hz). 7.29 (2 H, d, J=8.6 Hz).

HRMS (FAB) calcd for C$_{20}$H$_{30}$O$_5$+Na 373.1991, found 373.2007.

[α]$_D$ −12.2° (C 0.98, MeOH).

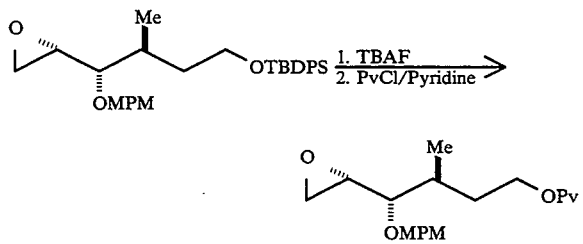

To a solution of TBDPS ether (790 mg, 1.56 mmol) in THF (30 mL) was added TBAF (5 mL, 5 mmol) at room temperature. After stirring for 2 h, the reaction mixture was concentrated, diluted with EtOAc, and saturated aqueous NH$_4$Cl. The organic layer was separated and washed with water followed by brine. The organic layer was dried over sodium sulfate and concentrated under reduced pressure. The residue was purified by column chromatography with 25% EtOAc in hexanes to afford 406 mg of alcohol as a colorless oil.

The purified alcohol was dissolved in CH$_2$Cl$_2$ (10 mL) and treated with pyridine (0.90 mL, 10.9 mmol) and PvCl (1.20 mL, 9.39 mmol) followed by a catalytic mount of DMAP. The reaction mixture was stirred for 4 h and worked up as usual. The crude residue was purified by column chromatography with 33% EtOAc in hexane to afford the pivaloate (505 rag, 92% yield over 2 steps) as oil.

IR (film) 821 cm$^{-1}$, 1159, 1285, 1514, 1613, 1726, 2970.

$^1$H NMR (CDCl$_3$): δ 1.07 (9 H, s, t-Bu), 1.51 (1 H, m), 1.89 (1 H, m), 1.95 (1 H, m), 2.52 (1 H, m), 2.81 (2 H, m), 3.05 (1 H, m), 3.80 (3 H, s), 4.09 (2 H, m), 4.49 (1 H, d, J=11.5 Hz), 4.78 (1 H, d, J=11.5 Hz), 6.87 (2 H, d, J=8.6 Hz), 7.29 (2 H, d, J=8.6 Hz).

HRMS (FAB) calcd for C$_{20}$H$_{30}$O$_5$+Na 373.1991, found 373.2007.

[α]$_D$ −12.2° (c 0.98, MeOH).

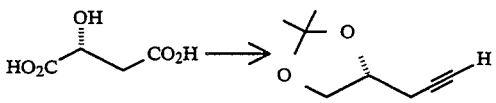

To a solution of BH$_3$ S Me$_2$ (87.5 mL, 0.923 mol) and trimethyl borate (91 mL, 0.80 mol) in 200 mL of THF at 0° C. was added dropwise a solution of D-(+)-malic acid (35 g, 0.261 mol) in THF (150 mL). The solution was warmed up to room temperature and was stirred overnight. Methanol (230 mL) was added dropwise and solvents were evaporated. Further three coevaporations with methanol (100 mL) and concentration in vacuo gave the crude product.

The crude product mixture was divided into two portions. Each portion was dissolved in 950 mL of acetone and TsOH.H$_2$O (1.0 g) was added. After each solution being stirred overnight, triethylamine (1 mL) was added and the mixture was stirred for a while. The solvent was removed by rotary evaporation. The combining residue was column chromatographed (Hexane:Acetone=7:3) to give 33 g (86%, two steps) of the mixture of products.

The mixture of products (33 g) was divided into 5 different batches. Two batches were oxidized by Swern's method and three batches were oxidized by the PCC method. PCC method was better than Swern's method for this particular substrate. All together 18.0 g (55%) of the aldehyde was obtained.

The mixture of aldehyde (18 g) was divided into 5 g (34.7 mmol) and 13 g (90.2 mmol) batches. The following is a procedure for the 13 g scale reaction. To a suspension of KO$^t$Bu (13.3 g, 119 mmol) in 350 mL of THF at $-78°$ C. was added dropwise DAMP (16.2, 108 mmol). After the mixture being stirred for 15 min, a solution of the aldehyde in 40 mL of THF was added dropwise (ca. 10 min). After 12 h stirring at this temperature, water (100 mL) was added. The organic layer was separated and was diluted with methylene chloride (350 mL). This organic layer was washed with water (4×70 mL) and brine (50 mL). The combined aqueous layer was extracted with methylene chloride (150 mL and 50 mL). These extracts were washed with brine (30 mL). All combined organic layers were dried (NaSO$_4$). Solvents were distilled off after extracts of the 5 g reaction mixture had been combined. Vacuum distillation of the residue gave 9.24 g (52%) of the desired product (bp. 62°–64° C./ca. 25 mmHg).

IR (film) 732 cm$^{-1}$, 910, 1069, 2270, 2901, 2963, 3021, 3309.

$^1$H NMR (CDCl$_3$): δ1.36 (3 H, s), 1.43 (3 H, s), 2.00 (1 H, t, J=2.6 Hz), 2.42 (1 H, ddd, J=2.6, 7.3, 16.5 Hz), 2.53 (1 H, ddd, J=2.6, 5.2, 14.0 Hz), 3.77 (1 H, dd, J=6.2, 8.5 Hz), 4.11 (1 H, dd, J=6.0, 8.5 Hz), 4.24 (1 H, m).

HRMS (CI) calcd for C$_8$H$_{12}$O$_2$+H 141.0915, found (M +I-D+141.0923.

[α]$_D$ $-38.7°$ (c 1.68, MeOH).

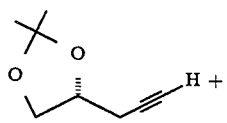

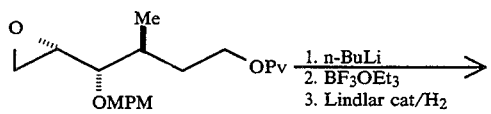

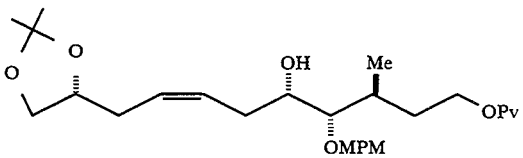

To a solution of acetylene (257 mg, 1.82 mmol) in THF (13 mL) was added n-BuLi (1.67 mmol) at $-78°$ C. After stirring for 1 h, BF$_3$.OEt$_2$ (0.20 mL, 1.60 mmol) was added to the anion solution and the reaction mixture was stirred for 20 min. To the reaction mixture was added a solution of epoxide (257 mg, 0.733 mmol) in THF (4 mL) over 20 min. After stirring for 1 h, it was stirred at $-45°$ C. for another 20 min and quenched with saturated NH$_4$Cl. After normal workup, the residue was purified by column chromatography with 20% ethyl acetate in hexanes to afford the alkyne (317 mg, 88.8% yield).

To the above solution of alkyne in hexanes (26 mL) was added quinoline (0.69 mL) followed by Pd/CaCO$_3$ (173 mg). To the reaction mixture was attached a hydrogen balloon and the reaction mixture was stirred for 50 min. The reaction mixture was filtered through Celite and the filtrate was washed with 10% HCl (2×10 mL), water, saturated aqueous NaHCO$_3$, and brine. After drying and concentration, it gave the homoallylic alcohol (310 mg, 97.8% yield).

IR (film) 1514, cm$^{-1}$, 1612, 1725, 2978, 3502.

$^1$H NMR (CDCl$_3$): δ 1.03 (3 H, d, J=6.9 Hz), 1.19 (9 H, s), 1.34(3 H, s), 1.41 (3 H, s), 1.51 (1 H, m), 1.88 (1 H, m), 1.96 (1 H, m), 2.20–2.42 (4 H, m), 2.44 (1 H, d), 3.14 (1 H, m), 3.54 (1 H, t, J=7.6 Hz), 3.69 (1 H, m), 3.80 (3 H, 4.02 (1 H, dd), 4.07–4.17 (2 H, m), 4.57 (2 H, dd), 5.56 (2 H, m), 6.88 (2 H, d), 7.26 (2 H, d).

HRMS calcd for C$_{28}$H$_{44}$O$_7$+Na (M++ Na) 515.2985, found 515.2972.

[α]$_D$ $-7.3°$ (C 1.1, MeOH).

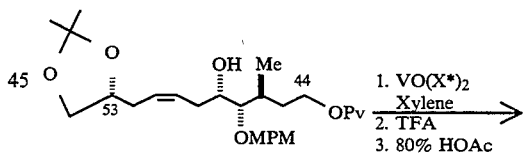

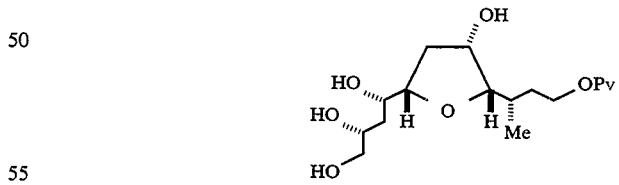

To a solution of alkene (1.01 g, 2.23 mmol) in xylene (18 mL) was added VO(X*)2 (10 mg) followed by 3M t-BuOOH (743 mL). The reaction mixture was stirred for 30 min at room temperature. Additional catalyst (3 mg) and t-BuOOH (185 μL) were added. After 12 h, catalyst (3 mg) and t-BuOOH (75 μL) were added and the reaction mixture was stirred for an additional 12 h. (The reaction was stopped before it showed a higher spot than starting material on TLC plate. The reaction time could be changed.) After reductive workup with sodium thiosulfate solution, the crude compound was dissolved in CH$_2$Cl$_2$ (35 mL). The solution was treated with TFA (1 eq.) for 10 min to produce a mixture of cyclized products. To the reaction mixture was added 80% HOAc (40 mL). The reaction mixture was stirred for 3 h, concentrated under reduced pressure, and purified by preparative TLC with 9% MeOH in EtOAc to afford the desired tetraol (420 mg, 59.6% yield) along with undesired tetraol (57 mg, 8.2% yield).

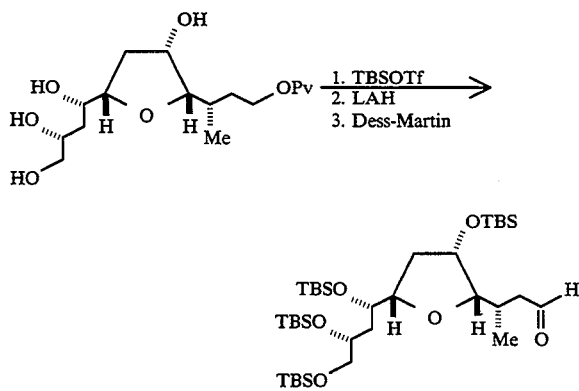

$^1$H NMR (C$_6$D$_6$): δ 0.00 (3 H, s), 0.04 (3 H, s), 0.14 (3 H, s), 0.25 (3 H, (3 H, s), 0.28 (3 H, s), 0.29 (3 H, s), 0.39 (3 H, s), 0.85 (3 H, d, J=6.8 Hz) 0.97 (9 H, s, t-Bu), 1.02 (9 H, s, t-Bu), 1.06 (9 H, s, t-Bu), 1.07 (9 H, s, t-Bu), 1.11(1 H, t, J=7.1 Hz), 1.55 (1 H, m), 1.64 (1 H, m), 1.76 (1 H, m), 1.89 (1 H, m), 1.99 (1 H, m), 2.04 (1 H, m), 2.18 (1 H, m), 3.03 (1 H, dd, J=3.4, 9.4 Hz), 3.25 (1 H, q, J=7.1 Hz), 3.64 (1 H, m), 3.70 (1 H, m), 3.81 (1 H, dd, J=3.9, 10.4 Hz), 3.87 (1 H, m), 3.89 (1 H, m), 4.04 (1 H, m), 4.25 (1 H, m).

HRMS (FAB) calcd for C$_{36}$H$_{80}$O$_6$Si$_4$+Na 743.4929, found 743.4937.

[α]$_D$ −1.5° (c 2.3, MeOH).

To a solution of the above alcohol (35 mg, 0.048 mmol) in CH$_2$Cl$_2$ (2.5 mL) of was added Dess-Martin reagent (42 mg, 2 eq.) with solid NaHCO$_3$ (2 eq.) to buffer this reaction system. The reaction mixture was stirred for 1.5 h, and worked up with sodium thiosulfate (6 eq.) solution in saturated aqueous NaHCO$_3$. After extraction, drying, and concentration, the residue was purified by column chromatography with 20% EtOAc in hexanes to give 34 mg of aldehyde in quantitative yield.

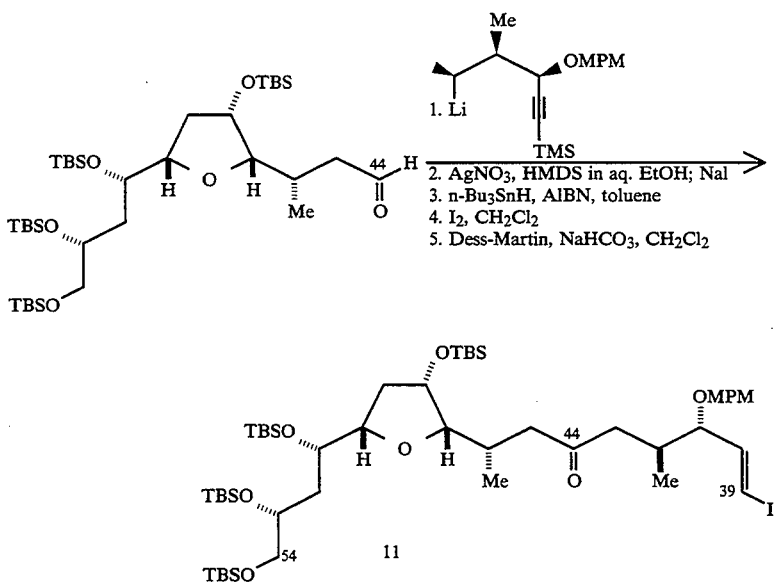

To a solution of tetraol (42.1 mg, 0.120 mmol) in CH$_2$Cl$_2$ (2 mL) at 0° C. was added TBSOTf (0.194 mL, 0.845 mmol) and NEt$_3$ (0.202 mL, 1.45 mmol). The reaction mixture was stirred for 1.6 h and quenched with saturated aqueous NaHCO$_3$. The mixture was extracted with ether (3×5 mL) and the combined organic layers were washed with water and brine. The solvent was dried over Na$_2$SO$_4$, filtered, and concentrated. The residue was purified by column chromatography with 60% EtOAc in hexanes.

The purified compound (89.3 mg) was dissolved in ether (10 mL) and treated with 1.6M LAH in ether (2 eq.) at 0° C. After stirring for 5 min, the reaction mixture was quenched with saturated aqueous Rochelle salt. The reaction mixture was stirred until it formed a clear solution. Normal extraction and purification by column chromatography with 12% EtOAc in hexanes gave the alcohol (67 mg, 83.9% yield).

IR (film) 775 cm$^{-1}$, 836, 1078, 1254, 1473, 2857, 2929, 2955, 3450.

To a solution of of bromide (46 mg, 0.122 mmol) in ether (1.5 mL) was added 1.7M t-BuLi in ether (0.139 mL, 0.105 mmol) at −78° C. After 20 min, a solution of aldehyde (16 mg, 0.022 mmol) was added to the anion solution. The reaction mixture was stirred for 30 min, and quenched with saturated aqueous NH$_4$Cl. Normal work-up, followed by a chromatographic separation with 6% EtOAc in hexanes gave two epimeric alcohols. Higher R$_f$ alcohol (11.4 mg, 51% yield) and lower R$_f$ alcohol (5.8 mg, 26% yield), along with a mixed fraction (2.9 mg, 13% yield)

To a solution of alcohol (11.4 mg, 0.011 mmol) in ethanol (2 mL) was added HMDS (16.7 μL, 0.077 mmol) followed by a solution of AgNO$_3$ (11.5 mg, 0.067 mmol) in 65% aqueous ethanol (1.06 mL). The reaction mixture was stirred for 1 h until the formation of a brown precipitate and clear solution indicated completion of the reaction. The reaction mixture was diluted with ether (2 mL) and treated with a solution of NaI (20 mg, 0.132 mmol) in 0.4 mL of H$_2$O. It was stirred for 20 min and filtered through Celite. The filtrate was extracted with ethyl acetate (3×7 mL). The the combined organic layers were concentrated and the residue was filtered through a short SiO2 plug to afford ~11 mg of acetylene. This acetylene was dried by azeotropic removal of water and dissolved in toluene (1 mL).

To the above solution was added n-Bu3SnH (0.1 mL, 0.15 mmol) followed by a catalytic amount of AIBN. The reaction mixture was heated to 80° C. for 1 h, concentrated, and purified by column chromatography with 6% ethyl acetate in hexanes to give the vinyl tin (10.7 mg, 80% yield).

To a purified vinyl tin solution in dichloromethane (1 mL) was added a solution of iodine (2.6 mg, 0.013 mmol) at 0° C. until the iodine color persisted. The reaction mixture was worked up as usual with NaHSO3 solution and the crude residue was purified by column chromatography with 6% ethyl acetate in hexanes to give the vinyl iodide. The vinyliodide in 1 mL of CH2Cl2 was treated with Dess-Martin reagent (2 eq.) for 1 h. After reductive worked up, the residue was purified by column chromatography with 4% EtOAc in hexanes to afford 9.8 mg of the ketone in quantitative yield).

Normally this 3-step reaction after coupling gave ~82% yield in a large scale

IR (film) 791 cm$^{-1}$, 863, 1084, 1271, 1622, 1727, 2856, 2929.

$^1$H NMR (C6D6): δ 0.01 (3 H, s), 0.02 (3 H, s), 0.14 (6 H, s), 0.25 (3 H, s), (3 H, s), 0.27 (3 H, s), 0.28 (3 H, s), 0.87 (3 H, d, J=6.8 Hz), 0.96 (9 H, s 0.98 (3 H, d, J=6.8 Hz), 1.02 (9 H, s), 1.07 (9 H, s), 1.08 (9 H, s), 1.35 (1 H, br s), 1.58 (1 H, m), 1.76 (1 H, m), 1.91 (1 H, m), 1.99 (1 H, m), 2.20 (1 H, dd, J=8.7, 16.7 Hz), 2.29 (1 H, dd, J=10.2, 16.7 Hz), 2.39 (1 H, m), 2.53 (1 H, dd, J=4.2, 16.7 Hz), 2.67 (I H, m), 2.97 (1 H, dd, J=2.2, 16.7 Hz), 3.10 (1 H, m), 3.30 (1 H, m), 3.32 (3 H, s), 3.69 (I H, dd, J=6.0, 10.3 Hz), 3.76 (1 H, m), 3.80 (1 H, dd, J=3.5, 10.3 Hz), 3.92 (1 H, m), 4.00 (1 H, m), 4.05 (1 H, d, J=11.5 Hz), 4.26 (1 H, m), 4.35 (1 H, d, J=11.5 Hz), 6.01 (1 H, d, J=14.5 Hz), 6.33 (I H, dd, J=7.8, 14.5 Hz), 6.79 (2 H, d, J=8.6 Hz), 7.13 (2 H, d, J=8.6 Hz).

HRMS (FAB) calcd for C50H95O8ISi4+Na 1085.5048, found 1085.5022.

[α]$_D$ −16.8° (c 1.4, CHCl3).

COMPOUND 12

Compound 12 was synthesized according to the following procedure.

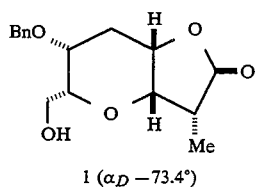

1 (α$_D$ −73.4°)

The above -lactose is readily available from D-galactose glycal ira Ireland-Claisen rearrangement and iodolactorrization. The lactase was treated by, according to standard procedures, with DEBAL/CH2Cl2/−78° C.→0° C.; p-TsOH/MeOH at room temperature; and Tf2O/Py/CH2Cl2/−42° C., followed by treatment with NaCN/DMF at room temperature to yield the nitrile 001.

Reduction of Nitrile 001

Dibal-H (0.60 mL, 0.60 mmol) was added to a solution of nitrile 001 (80.0 mg, 0,252 mmol) in methylene chloride (3.0 mL) cooled to −78° C. The reaction mixture was stirred for 2 h at −78° C. and then quenched by the addition of methanol (1 mL) followed by saturated aqueous ammonium chloride (1 mL). The mixture was diluted with ether (6.0 mL) and the resulting solution was warmed to room temperature. After 2 h at room temperature, a heterogeneous solution was obtained and the white precipitate was removed via filtration through a bed of Celite. The filtrate was washed with aqueous 1N HCl (10 mL), saturated NaHCO3 (20 mL) and brine (30 mL). The organic extract was then dried over solid sodium sulfate and the solvent removed in vacuo to provide a yellow oil (88 mg) which was used directly in the next step without further purification.

Reduction of Aldehyde 002—Synthesis of

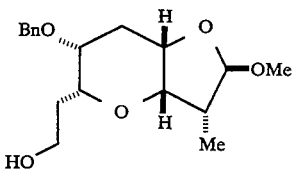

A solution of aldehyde 002 (80 mg, 0.25 mmol) in MeOH/CH2Cl2 (3:1; 4.0 mL) was cooled to 0° C. Sodium borohydride (30 mg, 0.79 mmol) was added in portions to this solution and the resulting mixture was stirred at 0° C. for 1 h. The mixture was then concentrated under reduced pressure and the resulting oil was partitioned between ethyl acetate (20 mL) and water (10 mL). The organic layer was removed, washed with brine, dried over Na2SO4 and concentrated in vacuo. The residual oil was purified by flash chromatography (hexanes/ethyl acetate; 3:2) to provide alcohol 003 (65 mg, 81% yield) as a colorless oil.

IR (film): 697, 1011, 1097, 1454, 1496, 2877, 2919, 3466 br, cm$^{-1}$.

$^1$H NMR (500 MHz, CDCl3): δ 1.12 (3H, d, J=7.2 Hz), 1.56 (1H, m), 1.63 (1H, ddd, J=4.1, 4.1, 15.8 Hz), 2.17-2.21 (2H, m), 2.41 (1H, br s), 2.57 (1H, ddd, J=2.0, 2.0, 15.8 Hz), 3.29 (1H, m), 3.41 (3H, s), 3.50 (1H, m), 3.72-3.85 (2H, m), 3.83-4.09 (1H, m), 4.10 (1H, m), 4.41 (1H, d, J=12.2 Hz), 4.78 (1H, d, J=12.2 Hz), 4.85 (1H, d, J=5.8 Hz).

HRMS calcd for C18H27O5 [M+H]+ 323.1858, found 323.1837.

[α]$_D$: −49.3° (C 0.41, MeOH).

Hydrogenolysis of Benzylether 003

A suspension of palladium hydroxide (Perleman's catalyst) in absolute ethanol (0.5 mL) was added to a solution of benzyl ether 003 (61 mg, 0.196 mmol) in absolute ethanol (2.5 mL) cooled to 0° C. An atmosphere of hydrogen gas was introduced using an inflated balloon and the resulting mixture was stirred at room temperature for 17 h. The suspension was filtered through Celite and the filtrate was concentrated in vacuo to provide alcohol 004 (45 mg, 99% yield) as a colorless oil. Analysis of this product by NMR suggested no further purification was required.

Preparation of Trisilyated triol 004 from methyl glycoside 003

Ethanethiol (3 mL) was added to a solution of methyl glycoside 003 (43 mg, 0.186 mmol) in methylene chloride (3 mL) cooled to 0° C. Boron trifluoride etherate (0.1 mL, 0.80 mmol) was added and the mixture was stirred at 0° C. for 4 h. The reaction mixture was poured into a separatory funnel containing ice-cold ethyl acetate and saturated sodium bicarbonate solution. The aqueous layer was thoroughly extracted with ethyl acetate followed by methylene chloride and the combined organic extracts were dried by treatment of sodium sulfate. The organic solution was concentrated in vacuo and the residual oil purified by a short plug of silica (ethyl acetate) to provide the triol 003A (66 mg) as a yellow oil.

To a solution of the triol 003A (66 mg) in methylene chloride (2 mL) cooled to 0° C. was added triethylamine (0.15 mL, 1.1 mmol) followed by TBSOTf (0.128 mL, 0.55 mmol). The reaction mixture was stirred at 0° C. for 1 h and after this time additional triethylamine (0.15 mL, 1.1 mmol) and TBSOTf (0.128 mL, 0.55 mmol) was added. The mixture was warmed to room temperature and stirred for an additional 2 h. The reaction mixture was quenched by the addition of a saturated sodium bicarbonate solution and the resulting mixture was thoroughly extracted with ether. The combined organic extracts were washed with brine, dried over Na$_2$SO$_4$ and concentrated in vacuo. The residual oil was purified by flash chromatography (hexanes/ethyl acetate; 15:1) to provide the trisilyated triol 004 (96 mg, 70% yield from diol methyl glycoside) as a light yellow oil.

Conversion of diethylthioacetal 004 to alcohol 005

Sodium bicarbonate (83.0 mg, 0.97 mmol) followed by iodine (83.0 mg, 0.327 mmol) was added to a solution of diethyl thioacetal 004 (138 mg, 0.218 mmol) in acetone/water (9:1) at 0° C. After 2.5 h, further quantities of sodium bicarbonate (4.5 eq) and iodine (1.5 eq) were added and the mixture was stirred for an additional 1 h. The reaction mixture was diluted with ethyl acetate (20 mL) and the resulting solution washed with saturated aqueous sodium thiosulfate, saturated aqueous NaHCO$_3$, and brine. The organic solution was dried with sodium sulfate and concentrated under reduced pressure to afford 137 mg of the crude aldehyde 004A which was used directly in the next step.

To a solution of the aldehyde (137 mg) in methanol/methylene chloride (15 mL; 2:1) at 0° C. was added sodium borohydride (50 mg) in portions. The solution was stirred at 0° C. for 30 min, then concentrated under reduced pressure. The residual oil was partitioned between ethyl acetate (50 mL) and water (20 mL) and the organic layer was washed with brine, dried over solid Na$_2$SO$_4$ and concentrated in vacuo. The crude oil was purified by flash chromatography (hexanes:ethyl acetate, 3:1) to provide alcohol 005 (106 mg, 93% yield) as a colorless oil.

Synthesis of Nitrile 007

Methanesulfonyl chloride (60 mL, 0.774 mmol) was added to a solution of alcohol 005 and triethylamine (125 mL, 0.838 mmol) in methylene chloride (5.0 mL) and the reaction mixture was stirred at room temperature for 10 min. The mixture was diluted with methylene chloride (20 mL) and quenched by the addition of saturated aqueous ammonium chloride (20 mL). The organic extract was washed with aqueous sodium bicarbonate followed by brine, dried over solid Na$_2$SO$_4$, and concentrated in vacuo. The crude oil (400 mg) was used directly in the next step without further purification.

Sodium cyanide (350 mg) was added to a solution of mesylate (400 mg) in DMSO (4 mL) and the mixture was stirred at 60° C. for 3 h. The reaction mixture was cooled to room temperature and diluted with ice-cold brine. The mixture was exhaustively extracted with ethyl acetate and the combined organics were washed with brine, dried over Na$_2$SO$_4$, and concentrated in vacuo. The residual oil was purified by flash chromatography (hexanes/ethyl acetate; 9:1) to afford the nitrile 007 (338 mg, 92% yield).

IR (film): 772, 837, 1006, 1019, 1030, 1100, 1255, 1386, 1463, 1472, 2125, 2857, 2884, 2929, 2955 cm$^{-1}$.

$^1$H NMR (500 MHz, CDCl$_3$): δ 0.02 (9H, s), 0.04 (3H, s), 0.05 (3H, s), 0.09 (3H, s), 0.86 (9H, s), 0.88 (9H, s), 0.89 (9H, s), 1.04 (3H, d, J=6.7 Hz), 1.49 (1H, m), 1.84 (1H, ddd, J=4.2, 4.4, 10.6 Hz), 1.93 (1H, m), 2.00 (1H, d, J=14.9 Hz), 2.30 (1H, m), 2.46 (1H, dd, J=7.5, 16.7 Hz), 2.60 (1H, dd, J=3.2, 16.6 Hz), 2.94 (1H, d, J=8.9 Hz), 3.42 (1H, d, J=10.2 Hz), 3.60 (1H, m), 3.69–3.73 (2H, m), 3.81 (1H, m).

HRMS calcd for C$_{29}$H$_{62}$O$_4$Si$_3$N [M+H]$^+$ 572.3986, found 572.3997.

[α]$_D$: −0.87° (c 1.95, MeOH).

Preparation of Aldehyde 008 from Nitrile 007

A solution of diisobutylaluminum hydride in hexanes (1.0M, 2.5 mL, 2.5 mmol) was added dropwise to a stirred solution of nitrile 007 (310 mg, 0.543 mmol) in methylene chloride (5 mL) cooled to −78° C. The reaction mixture was stirred for an additional 1.5 h and quenched by the consecutive addition of methanol (6 mL), a saturated ammonium chloride solution (6 mL) and ether (6 mL). The mixture was warmed to room temperature and stirred for an additional 1 h. The mixture was filtered through Celite and the Celite pad was washed with ether. The filtrate was washed with a saturated ammonium chloride solution (20 mL) followed by brine, dried over solid Na$_2$SO$_4$, and concentrated in vacuo. The residual oil was purified by flash chromatography (hexanes/ethyl acetate; 9:1) to afford the aldehyde 008 (296 mg, 96% yield) as a colorless oil.

Aldehyde 008 had the following structure:

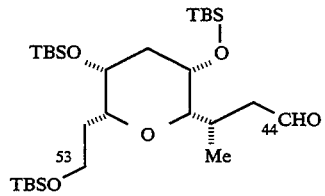

The bromide (compound 105)

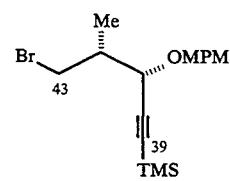

was synthesized according to the following procedure. The bromide will eventually be reacted with aldehyde 008 to yield compound 12.

The bromide was synthesized from (S)-(+)-methyl 3-hydroxy-2-methylpropionate (Aldrich) (100) in approximately 40% overall yield, in eight steps.

Conversion of [β-Hydroxy Ester 100 to Alcohol 101 p-Toluenesulfonic acid (80 mg, 0.42 mmol) was added to a solution of alcohol 100 (21.0 g, 0.177 mol) and dihydropyran (26 mL, 0.284 mol) in ethyl ether (180 mL) and the mixture was stirred at room temperature for 20 h. The reaction mixture was quenched by the addition of a saturated sodium bicarbonate solution and the resulting mixture was thoroughly extracted with ether. The combined organics were washed with brine, dried over solid $Na_2SO_4$ and concentrated in vacuo to provide 40 g of the THF ether 100A. The crude product was used directly in the next step without further purification.

Lithium aluminum hydride (10.0 g, 0.263 mol) was added slowly over 1 h to an ice-cold solution of ether. The ester 100A (443 g) in ether (200 mL) was then added dropwise to the slurry and the resulting mixture was stirred at 0° C. for 12 h. The reaction mixture was quenched by the successive addition of ethyl acetate (40 mL), water (40 mL), 1N sodium hydroxide solution (40 mL) and water (40 mL). The resulting slurry was filtered through Celite and the Celite pad was washed with ether. The filtrate was washed with brine and the organic extract dried over solid $Na_2SO_4$, and concentrated in vacuo. The residual oil was purified by vacuum distallation to afford the alcohol 101 (29.0 g, 94% yield), b.p. 105° C. (0.1 Torr).

Swern Oxidation of Alcohol 101

Oxalyl chloride (12.0 mL, 0.137 mol) was added to methylene chloride (60 mL) cooled to −78° C. A solution of dimethyl sulfoxide (13 mL, 0.183 mol) in methylene chloride (30 mL) was then added dropwise over 15 min. A solution of alcohol 101 (16.0 g, 0.091 mol) in methylene chloride (30 mL) was added dropwise over 20 min and the resulting mixture was stirred for 30 min at −78° C. A solution of triethylamine (64.1 mL, 0.459 mol) in methylene chloride (30 mL) was then added and the mixture was stirred for 30 min at −78° C. The reaction mixture was them removed from the cooling bath and warmed to 0° C. over 15 min. The reaction slurry was then partitioned between benzene/ether (600 mL; 4:1) and water (800 mL). The organic layer was removed and washed with water (2×500 mL) and brine. The organic extract was then dried over solid $Na_2SO_4$ and concentrated in vacuo to provide 15.8g of the aldehyde 102 as a light yellow oil. The crude aldehyde was used immediately in the next step without further purification.

1,2-Addition to Aldehyde 102

A solution of butyllithium in hexanes (50.0 mL, 0.105 mol) was added to a solution of trimethylsilylacetylene in ether (400 mL) at −78° C. The mixture was warmed to 30° C. and stirred for 30 min. The solution was cooled to −78° C. and a solution of aldehyde 101 (14.0 g, 0.091 mol) in ether (30 mL) was added dropwise over 20 min. The reaction mixture was maintained for 1 h at −78° C. and quenched by the addition of a saturated ammonium chloride solution. The resulting mixture was warmed to 0° C. and exhaustively extracted with ethyl ether. The combined organic extracts were washed with brine, dried over solid $Na_2SO_4$ and concentrated in vacuo. The residual oil (22 g) was purified by flash chromatography (hexanes/chloroform/ethyl acetate; 10:4:1 ) to provide 5.5 g of desired alcohol, 7.1 g of mixed fractions and 6.1 g of undesired alcohol (85% overall yield from alcohol 101).

MPM Protection of Propargyl Alcohol 103

A solution of propargyl alcohol (2.0 g, 7.40 mmol) in methylene chloride (10 mL) was added to a solution P-methoxybenzyltrichloroimidate in methylene chloride (500 mL) cooled to 0° C. A solution of boron trifluroetherate in methylene chloride (0.2N, 0.7 mL, 0.14 mmol) was added dropwise and the initially yellow solution took on an orange color. After 10 min, TLC analysis indicated the reaction was complete. The reaction mixture was quenched by the addition of a saturated sodium bicarbonate solution. The organic layer was removed and the remaining aqueous layer was thoroughly extracted with methylene chloride. The combined organic extracts were washed with brine, dried over solid $Na_2SO_4$ and concentrated in vacuo. The residual solid was dissolved in equal amounts of benzene and hexanes and applied to a column of silica. Gradient elution with hexanes/ethyl acetate (50:1, 50:5) provided the protected alcohol 104 (2.49 g, 83% yield) as a light yellow oil.

Solvolsis of THF-Protected Alcohol 104

Camphorsulfonic acid (100 mg, 0.43 mmol) was added to a solution of THF ether 104 (2.0 g, 4.9 mmol) in methanol (50 mL). The reaction mixture was stirred at room temperature for 9.5 h, then quenched by the addition of solid sodium bicarbonate (36 mg, 0.43 mmol). The mixture was stirred for 20 min, then concentrated in vacuo. The residual oil was partitioned between ether (40 mL) and water (20 mL) and the organic extract was washed with brine, dried over solid $Na_2SO_4$, and concentrated in vacuo. The residual oil was purified by flash chromatography (hexanes/ethyl acetate; 9:1) to provide the alcohol 104 (1.3 g, 87% yield) as a colorless oil.

Conversion of Alcohol 104 to Bromide 105

Triethylamine (0.228 mL, 1.52 mmol) was added to a solution of alcohol 104 (380 mg, 1.17 mmol) in methylene chloride (5 mL) cooled to 0° C. Methanesulfonyl chloride was added and the solution was stirred for 30 min at 0° C. The reaction mixture was then diluted with methylene chloride (20 mL) and quenched by the addition of a saturated ammonium chloride solution (30 mL). The organic layer was washed consecutively with a 0.3N HCl solution (20 mL), saturated sodium bicarbonate solution, and brine. The organic solution was then dried over solid $Na_2SO_4$, and concentrated in vacuo. The crude oil (470 mg) was used directly in the next step without further purification.

Lithium bromide (1.02 g, 11.7 mmol) was added to a solution of mesylate 104A (470 mg) in THF (10 mL) at room temperature. The reaction mixture was stirred for 2 h at reflux, then cooled to room temperature and transferred to a separatory funnel containing ether (40 mL) and water (30 mL). The organic layer was removed, washed with brine, dried over solid $Na_2SO_4$, and concentrated in vacuo. The residual oil was purified by flash chromatography to provide the bromide 105 (418 mg, 93% yield) as a light yellow oil.

IR (film): 760, 843, 1023, 1037, 1073, 1251, 1514, 1612, 2168, 2835, 936, 2961 cm$^{-1}$.

$^1$H NMR (500 MHz, CDCl$_3$): δ 0.18 (3H, s), 1.11 (3H, d, J=6.7 Hz), 2.11 (1H, m), 3.46–3.52 (2H, m), 3.78 (3H, s), 4.04 (1H, d, J=7.1 Hz), 4.41 (1H, d, J=11.1 Hz), 4.70 (1H, d, J=11.1 Hz).

HRMS calcd for C$_{17}$H$_{25}$O$_2$Br [M]+ 368.0807, found 368.0810.

[α]$_D$: −70.6° (C 1.33, MeOH).

Coupling of Bromide 105 and Aldehyde 008

A solution of t-butyllithium (0.71 mL, 1.21 mmol) in hexane was added to a solution of bromide 105 (249 mg, 0.674 mmol) in ether at −78° C. The solution was stirred for 20 min at −78° C. and after this time a solution of the aldehyde (73 mg, 0.127 mmol) in ether (3 mL) was added via cannula over 1 min. The reaction mixture was stirred for 30 min at −78° C., then quenched by the addition of saturated ammonium chloride (20 mL). The resulting mixture was warmed to room temperature, then exhaustively extracted with ether. The combined organic extracts were washed with brine, dried over solid Na$_2$SO$_4$, and concentrated in vacuo. The residual oil was purified by flash chromatography (hexanes/ethyl acetate; 9:1) to provide alcohol 011 (94 mg, 86% yield) as a mixture of diastereoisomers.

Deprotection of TMS Protected Alkyne 011

A solution of silver nitrate (256 mg, 1.51 mmol) in absolute ethanol (10 mL) and water (6.0 mL) was added dropwise over 15 min to a solution of protected alkyne 011 (227 mL, 0.262 mmol) in absolute ethanol (41 mL) and HMDS (0.387 mL, 1.83 mmol). The reaction mixture was stirred for 2 h at room temperature, then quenched by the addition of sodium iodide (472 mg, 3.14 mmol) in ether (20 mL). The mixture was filtered through Celite and the Celite pad was washed with ether. The filtrate was concentrated and the residue partitioned between ether (30 mL) and water. The organic layer was washed with brine, dried over solid Na$_2$SO$_4$ and concentrated in vacuo. The residual oil was purified by flash chromatography (hexanes/ethyle acetate; 4:1 ) to provide the terminal alkyne 012 (206 mg, 99% yield) as a colorless oil.

Preparation of Vinyl Stannane 012A

A solution of alkyne 012 (45 mg, 0.057 mmol) and AIBH (5 mg) in toluene (3 mL) and tributyltin hydride (0.3 mL) was stirred at 80° C. After 1 h, tributyltin hydride (0.4 mL) was added and the solution was stirred for an additional 1 h. The mixture was cooled to room temperature and concentrated in vacuo. The residual oil was purified by flash chromatography (hexanes/ethyl acetate; 5:1) to provide vinyl stannane 12A (56 mg, 92% yield) as a mixture of geometric isomers (trans:cis, 9:1).

Preparation of Vinyl Iodide 013

A solution of iodine (15 mg, 0.059 mmol) in methylene chloride (1 mL) was added dropwise to a solution of vinyl stannane 012A (56 mg, 0.0517 mmol) in methylene chloride (4 mL,) cooled to 0° C. The light pink solution was stirred for 10 min at 0° C., then diluted with methylene chloride (20 mL). The resulting mixture was washed with a sodium thiosulfate solution (30 mL) and brine. The organic extract was then dried over solid Na$_2$SO$_4$ and concentrated in vacuo. The residual oil was purified by flash chromatography (hexanes/ethyl acetate; 5:1) to afford the vinyl iodide 013 (44 mg, 94% yield) as a light yellow oil.

Dess-Martin Oxidation of Alcohol 014

Dess-Martin periodane (100 mg, 0.235 mmol) was added in portions to a solution of alcohol 014 (4–4 mg, 0.048 mmol) in methylene chloride cooled to 0° C. Sodium bicarbonate (8.0 mg) was then added and the solution was stirred at 0° C. for 2 h. The mixture was diluted with ether (10 mL) and quenched by the addition of a saturated sodium bicarbonate solution (8 mL) containing 4 dissolved crystals of sodium thiosulfate. The solution was vigorously stirred for 1 h. The mixture was then thoroughly extracted with ether and the combined organic extracts were washed with brine and dried over solid Na$_2$SO$_4$. The solvent was removed in vacuo and the residual oil was purified by flash chromatography (hexanes/ethyl acetate; 4:1) to provide the aldehyde 12 (40 mg, 91% yield) as a colorless oil.

COMPOUND 1

Compound 1, halichondrin B, was prepared from compounds 10 and 11 by the following procedure.

C38 Aldehyde

To a stirred solution of the compound 10 (8.1 mg, 9.0 μmole) in CH$_2$Cl$_2$ (1.0 mL) at room temperature was added solid NaHCO$_3$ (50 mg) followed by the Dess-Martin periodinane reagent (15 mg, 36 μmole). Additional Dess-Martin reagent (15 mg, 36 μmole) was added after 30 min. After a total of 90 min, TLC (2:1 ethyl acetate/hexanes) showed no remaining starting material. The reaction mixture was diluted with diethyl ether (5 mL) and an aqueous solution (5 mL) saturated with NaHCO$_3$ and containing 10% Na$_2$S$_2$O$_3$ by wt. The resulting biphasic mixture was stirred at room temperature for 20 min. The separated organic phase was washed with additional aqueous NaHCO$_3$/Na$_2$S$_2$O$_3$ for 10 min, H$_2$O, and brine (5 mL ea.). The organic phase was dried over Na$_2$SO$_4$, filtered through glass wool, and concentrated. The aldehyde (8 mg, ca. 8.9 μmole) thus obtained was used directly without further purification.

Halichondrin B: C38 Ketone

To a stirred solution of the C38 aldehyde (8 mg, 8.9 μmole) and compound 11 (24 mg, 22 μmole) in DMF (ca. 1 mL) under nitrogen was added powdered CrCl$_2$ containing 0.1% NiCl$_2$ by mass (ca. 30 mg total). After stirring at room temperature for 11.5 h, TLC (hexanes/ethyl acetate/CHCl$_3$ 1:2:1) showed no remaining aldehyde. The mixture was diluted with saturated aqueous NH$_4$Cl (10 mL) and H$_2$O (2 mL,) and extracted with ethyl acetate (4×5 mL). The combined ethyl acetate extracts were washed with H$_{20}$ (2×10 mL) and brine (10 mL), dried over Na$_2$SO$_4$, filtered through glass wool, and concentrated. Purification of the residue by PTLC (hexanes/ethyl acetate/CHCl$_3$ 1:2:1) gave the C38 ailylic alcohols (11 mg, 6.0 μmole, 67% yield) as a clear, colorless oil and in an approximate 1:1 ratio of diastereomers To a stirred solution of the C38 alcohols (8.0 mg, 4.4 μmole) in CH$_2$Cl$_2$ (2.00 mL) at room temperature was added solid NaHCO$_3$(50 mg) followed by the Dess-Martin periodinane reagent (14.8 mg, 35 μmole). After stirring at room temperature for 1 h, additional Dess-Martin reagent (14.8 mg) was added. After 90 min total, the reaction mixture was diluted with diethyl ether (6 mL) and and an aqueous solution (10 mL) saturated with NaHCO$_3$ and containing 10% Na$_2$S$_2$O$_3$ by wt. The resulting biphasic mixture was stirred at room temperature for 20 min. The separated organic phase was washed with additional aqueous NaHCO$_3$/Na$_2$S$_2$O$_3$ for 10 min, H$_2$O, and brine (10 mL ca.). The organic phase was dried over Na$_2$SO$_4$, filtered through glass wool, and concentrated. Purification of the residue by PTLC (1:1, hexanes/ethyl acetate) gave the enone (7.4 mg, 4.1 μmole, 93% yield) as a clear, colorless oil.

Halichondrin B

To a stirred solution of the enone (3.7 mg, 2.0 μmole) in DMF (750 μL) at room temperature was added anhydrous methyl acetate (50 μL) followed by an approximately 1M solution of tetrabutylammonium fluoride (TBAF) in THF (25 μL, pH ca. 7.6). The resulting solution was stirred at RT for 34 h, at which time HPTLC (E. Merck Art. 5642, plates were spotted with reaction solution, dried on a high vacuum line for 20–30 min, then eluted with 10:1 ethyl acetate/methanol) showed a major spot at $R_f$ 0.53. The reaction solution was filtered through a 2 cm pad of silica gel 60 (230–400 mesh) with ethyl acetate to remove the TBAF. The filtrate was concentrated in vacuo to a yellow oil (CJF-4-8) which was used without further purification. $^1$H NMR of the crude product showed no unsaturated ketone proton resonances, but two major products in an approximate 2:1 ratio. This compound corresponds to that having partial structure A.

The above product mixture was dissolved in a mixture of CH$_2$Cl$_2$ (1.00 mL), aqueous phosphate buffer (Na$_2$HPO$_4$/KH$_2$PO$_4$/H$_{20}$, pH 7.00, 100 μL) and t-butanol (20 μL). To the resulting rapidly stirred mixture was added 2,3-dichloro-5,6-dicyanobenzoquinone (1.8 mg, 8 μmole). The mixture was sonicated in an H$_2$O bath for 30 sec, stirred at room temperature without sonication for 3 min, sonicated for an additional 30 sec, and stirred for a final 16 min without sonication. HPTLC (10:1 ethyl acetate/methanol) showed no remaining starting material. The reaction mixture was washed with saturated aqueous NaHCO$_3$ (2×1 mL), H$_2$O, and brine (1 mL ca.). The combined aqueous fractions were extracted with CH$_2$Cl$_2$ (2×0.5 mL) and the combined organic fractions were dried over NaSO$_4$, filtered, and concentrated to an orange oil. The crude product was dried further on a high vacuum line for 1 h before being used directly in the following reaction.

The above product mixture was dissolved in anhydrous CH$_2$Cl$_2$ (1.00 mL) and to the stirred room temperature solution was added a solution of (+/−)-camphorsulfonic acid (CSA) in CH$_2$Cl$_2$ (10 μL of a 1.00 mg CSA/1.00 mL CH$_2$Cl$_2$ solution). After stirring 2 h at room temperature, HPTLC (10:1 ethyl acetate/methanol) showed essentially complete conversion to a major spot. The reaction solution was washed with saturated aqueous NaHCO$_3$ (2×0.5 mL), H$_2$O, and brine (0.5 mL ca). The combined aqueous fractions were extracted with CH$_2$Cl$_2$ (2×0.5 mL), and the combined organic fractions were dried over Na$_2$SO$_4$, filtered, and concentrated. The residue was chromatographed on HPTLC plates (10:1 ethyl acetate/methanol) to afford synthetic halichondrin B (1.27 mg, 1.1 μmole, 57% yield over three steps) as a colorless oil.

The synthetic product co-eluted with and was indistinguishable from a sample of the natural product on HPTLC plates in the following five solvent systems and with multiple elutions: (1) 10:1 ethyl acetate/methanol; (2) 10:1 ethyl acetate/CH$_2$Cl$_2$; (3) 10:5:1 ethyl acetate/CHCl$_3$/methanol; (4) 10:5:1 ethyl acetate/CH$_2$Cl$_2$/methanol; (5) 10:5:1 ethyl acetate/t-butylmethyl ether/methanol.

IR (cm$^{-1}$): 1017 cm$^{-1}$, 1073, 1187, 1737, 2852, 2923, 3438 (br).

$^1$HNMR (C$_6$D$_6$, 500 MHz):

HRMS (FAB): observed m/z=1111.5878 (M+), calcd for C$_{60}$H$_{86}$O$_{19}$ 1111.5841.

[α]$_D$: −51.2° (C 0.127, MeOH).

COMPOUND 2

Compound 2, norhalichondrin B, was prepared from the C38 aldehyde (derived from compound 10 as described above) and compound 12, as follows.

Norhalichondrin B: C38 Ketone

To a stirred solution of the C38 aldehyde (5.4 mg, 6.1 μmole) and compound 12 (13 mg, 12.2 μmole) in DMF (ca. 750 μL) under nitrogen was added powdered CrCl$_2$ containing 0.1% NiCl$_2$ by wt. (ca. 20 mg total). The resulting green mixture was stirred at room temperature for 16 h, at which time TLC (2:1:1 ethyl acetate/hexanes/CHCl$_3$) showed no remaining aldehyde. Saturated aqueous NH$_4$Cl (1 mL), H$_2$O (0.5 mL), and ethyl acetate (1 mL) were added and the resulting mixture was stirred for 20 min. The upper organic layer was separated and the lower phase was extracted further with ethyl acetate (3×0.5 mL). The combined ethyl acetate fractions were washed with H$_2$O (2×1 mL) and brine (1 mL), dried over Na$_2$SO$_4$, filtered through glass wool, and concentrated. The residue was purified by PTLC (1:1:1, hexanes/ethyl acetate/CHCl$_3$) to afford the C38 allylic alcohols (8 mg, 5 μmole, 83% yield) as a clear colorless oil as an approximate 1:1 mixture of diastereomers.

To a stirred solution of the C38 alcohols,, (8 mg, 5 μmole) in CH$_2$Cl$_2$ (1.00 mL) at room temperature was added solid NaHCO$_3$ (50 mg) followed by the Dess-Martin periodinane reagent (17 mg, 40 μmole). After stirring at room temperature for 90 min, TLC (1:1:1 hexanes/ethyl acetate/CHCl$_3$) showed no remaining starting material. The reaction mixture was diluted with diethyl ether (3 mL) and stirred for 20 min with an aqueous solution (5 mL) saturated with NaHCO$_3$ and containing 10% Na$_2$S$_2$O$_3$ by wt. The separated organic phase was washed with additional aqueous NaHCO$_3$/Na$_2$S$_2$O$_3$ for 10 min, H$_2$O, and brine (5 mL ca.). The organic phase was dried over anhydrous Na$_2$SO$_4$, filtered through glass wool, and concentrated. Purification of the residue by PTLC ( 1: 1: 1, hexanes/ethyl acetate/CHCl$_3$) gave the enone (6.3 mg, 3.9 μmole, 79% yield) as a clear, colorless oil.

IR (cm$^{-1}$): 835 cm$^{-1}$, 1088, 1252, 1463, 1737, 2929, 2953.

$^1$H NMR (C$_6$D$_6$, 500 MHz):

HRMS (FAB): m/z=([M+Na]+), calcd for ([C$_{86}$H$_{136}$O$_{21}$Si$_3$+Na]+, 1611.8779; observed, 1611.8811.

[α]$_D$: −32° (C 0.56, MeOH).

Norhalichondrin B Methyl Ester

To a stirred solution of the enone (3.15 mg, 2.4 μmole) in THF (400 μL) and anhydrous methyl acetate (200 μL) was added an approximately 1M solution of tetrabutylammonium fluoride (TBAF) in THF (20 μL, pH ca. 7.6). The resulting solution was stirred at room temperature for 14.5 h, at which time HPTLC (E.

Merck Art. 5642 plates were spotted with reaction solution, dried on a high vacuum line for 20–30 min, then eluted with ethyl acetate) showed one major spot at $R_f$ 0.45. The reaction solution was filtered through a 2 cm pad of silica gel 60 (230–400 mesh) with ethyl acetate to remove the TBAF. The filtrate was concentrated in vacuo to a yellow oil which was used without further purification.

The above product mixture was dissolved in $CH_2Cl_2$ (1.00 mL). Aqueous phosphate buffer (pH 7.00, 100 $\mu$L) and t-butanol (20 $\mu$L) were added, and to the resulting rapidly stirred mixture was added DDQ (1.8 mg, 8 $\mu$mole). The mixture was sonicated in an $H_2O$ bath for 3×30 sec, with stirring at room temperature without sonication for 3–5 min intervals between sonications. TLC (ethyl acetate) at this point showed no remaining starting material. The reaction mixture was washed with saturated aqueous $NaHCO_3$ (2×1 mL), $H_2O$, and brine (1 mL ca). The combined aqueous fractions were extracted with $CH_2Cl_2$ (2×0.5 mL) and the combined organic fractions were dried over $NaSO_4$, filtered, and concentrated to an orange oil. The crude product was dried further on a high vacuum line for 30 min before being used directly in the following reaction.

The above product was dissolved in anhydrous $CH_2Cl_2$ (1.00 mL) and to the stirred solution at room temperature was added a solution of (+/−)-camphorsulfonic acid (CSA) in $CH_2Cl_2$ (10 $\mu$L of a 1.00 mg CSA/1.00 mL $CH_2Cl_2$ solution). After 1 h, HPTLC (ethyl acetate) showed essentially complete reaction. The reaction solution was washed with saturated aqueous $NaHCO_3$ (2×0.5 mL), $H_2O$, and brine (0.5 mL ca.). The combined aqueous fractions were extracted with $CH_2Cl_2$ (2×0.5 mL), and the combined organic fractions were dried over anhydrous $Na_2SO_4$, filtered, and concentrated. The residue was chromatographed on HPTLC plates (ethyl acetate) to afford synthetic norhalichondrin B methyl ester (1.2 mg, 1.1 $\mu$mole, 45% yield over three steps) as a colorless oil. (CJF-4-28)

The synthetic product co-eluted with and was indistinguishable from an authentic sample (obtained from treatment of natural norhalichondrin B with diazomethane in methanol) upon multiple elutions on HPTLC plates with the two following solvent systems: (1) ethyl acetate (2) 25:1 $CH_2Cl_2$/methanol.

IR (cm$^{-1}$): 1021, 1073, 1189, 1435, 1739, 2924, 3609.
HRMS (FAB): (m/z=([M+Na]$^+$), calcd for [$C_{60}H_{84}O_{19}$+Na]$^+$, 1131.5504; observed 1131.5502.
[$\alpha$]$_D$: −46.4° (c 0.22, MeOH).

Norhalichondrin B

To a stirred solution of the methyl ester (2.2 mg, 2.0 $\mu$mole) in THF (300 $\mu$L) at room temperature was added a 1M aqueous LiOH solution (100 $\mu$L). After stirring for 90 min at room temperature, HPTLC (ethyl acetate) showed complete reaction. The THF was removed under a stream of $N_2$, and the resulting solution was diluted with $H_2O$ (200 $\mu$L) and cooled to 0° C. To the rapidly stirred solution was added 1M aqueous HCl (100 $\mu$L). The mixture was extracted with ethyl acetate (4×0.5 mL), and the combined extracts were dried over $Na_2SO_4$, filtered through glass wool, and concentrated. The residue was purified on a TSK G 300S polystyrene column (a 2 cm column was equilibrated with $H_2O$, the carboxylic acid was loaded in 50% aqueous ethanol, and eluted with $H_2O\rightarrow$ethanol) to afford the carboxylic acid (1.3 mg, 1.2 $\mu$mole, 60% yield) as a colorless oil. This compound is Norhalichandrin B (compound 2).

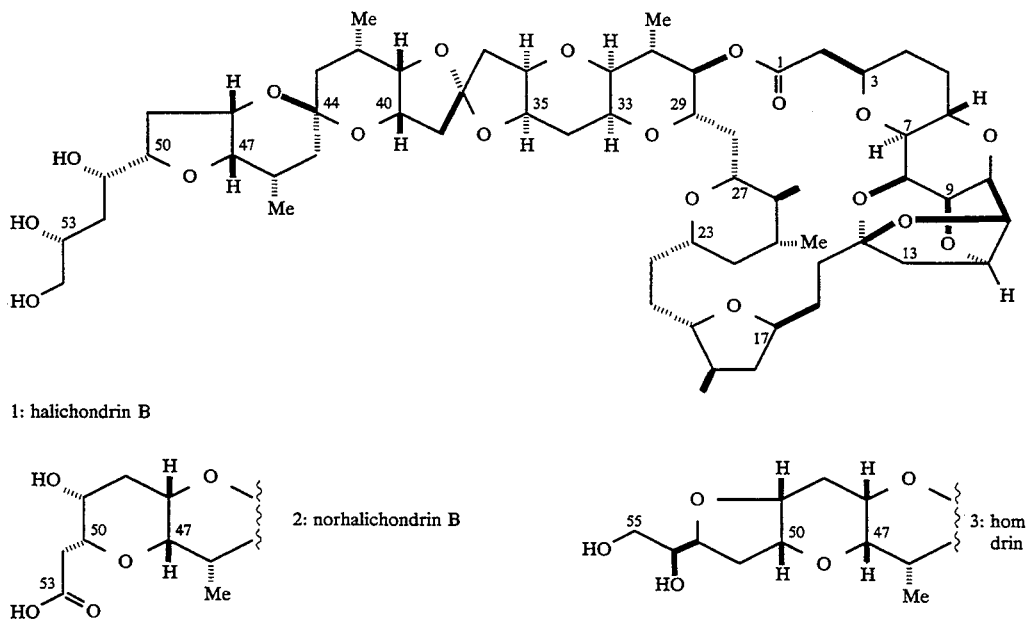

1: halichondrin B

2: norhalichondrin B

3: homohalichondrin B

Scheme 1

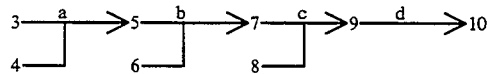

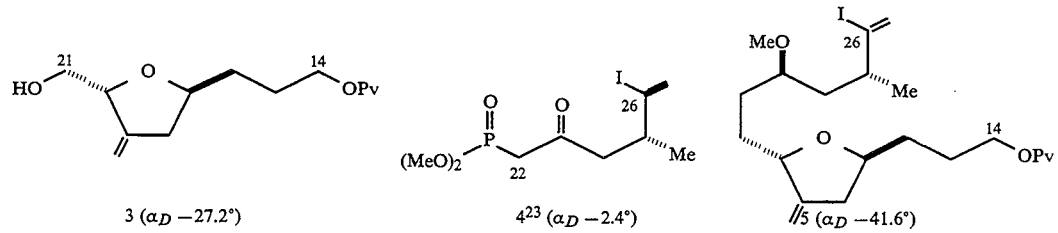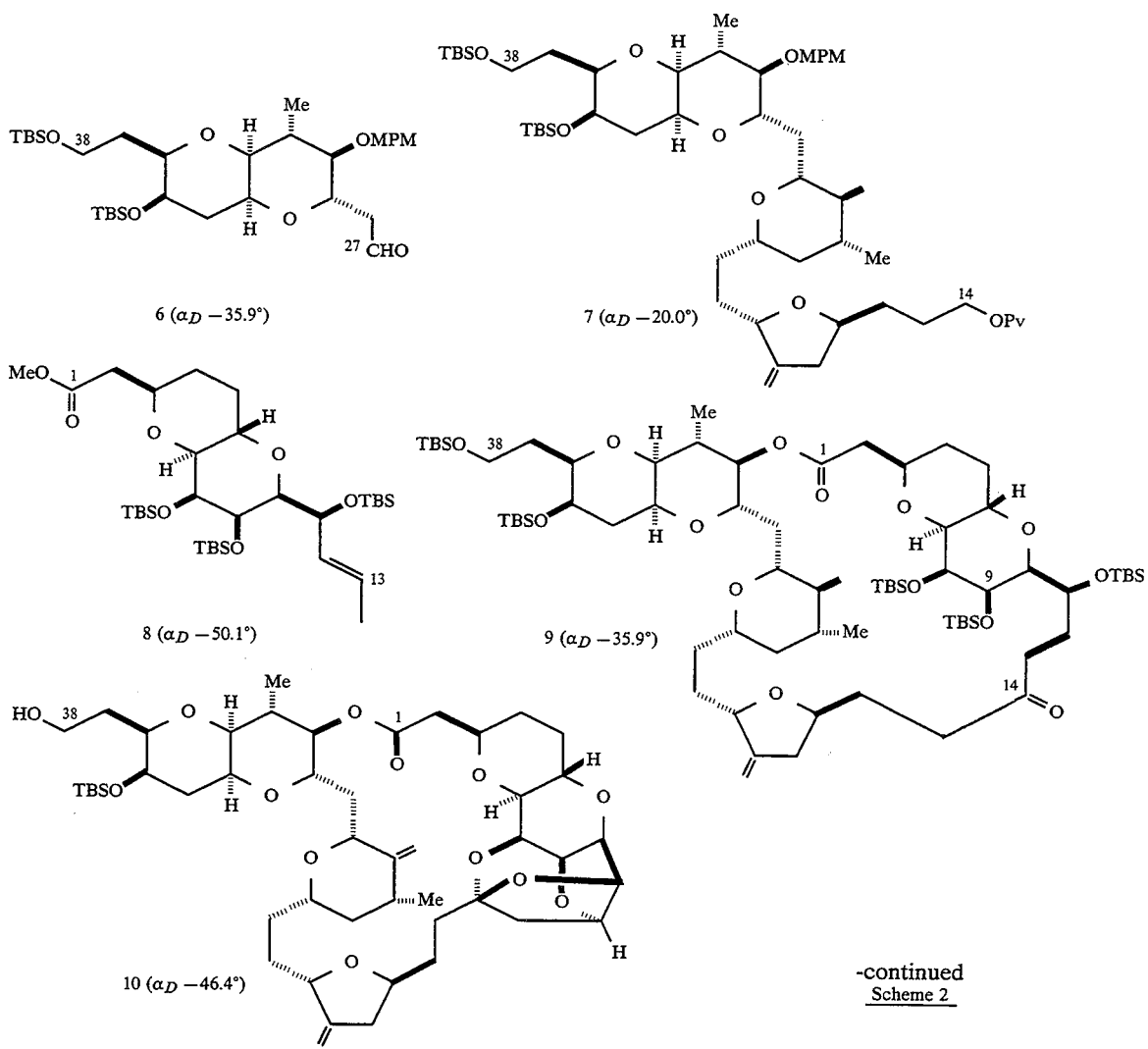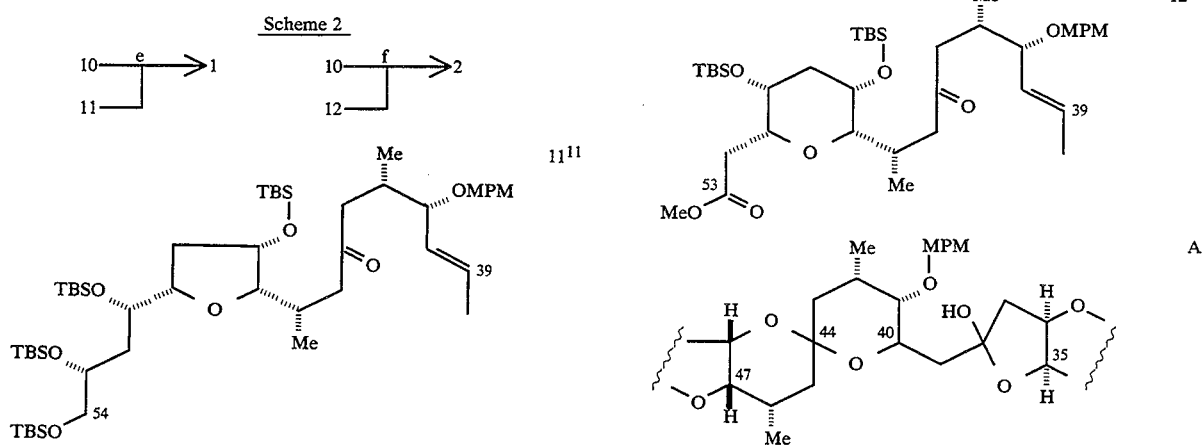

What is claimed is:
1. A compound having the following structure:

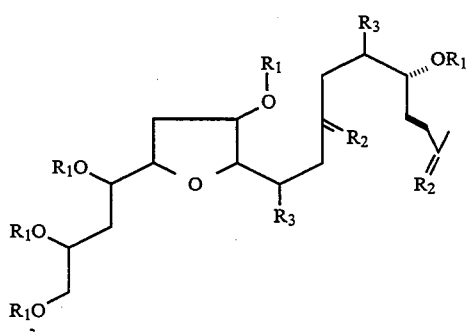

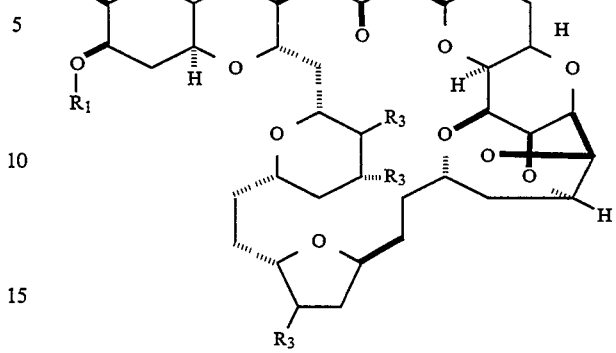

where each $R_1$, independently, is —H or an alcohol protecting group; $R_2$ is O or a protected ketone group; and each $R_3$, independently, is —H or an alkyl group having 5 or fewer carbon atoms.

2. The compound of claim 1, wherein said compound has the following structure:

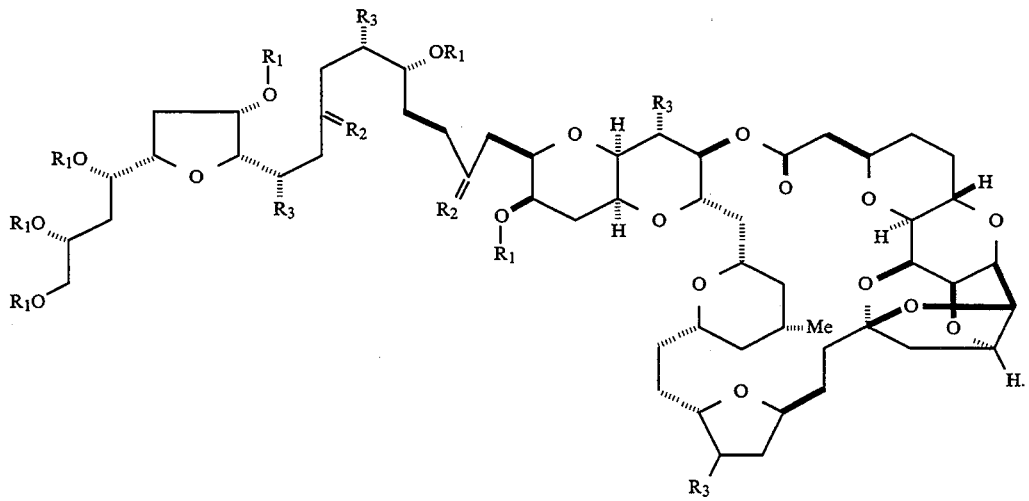

3. The compound of claim 2, wherein said compound has the following structure:

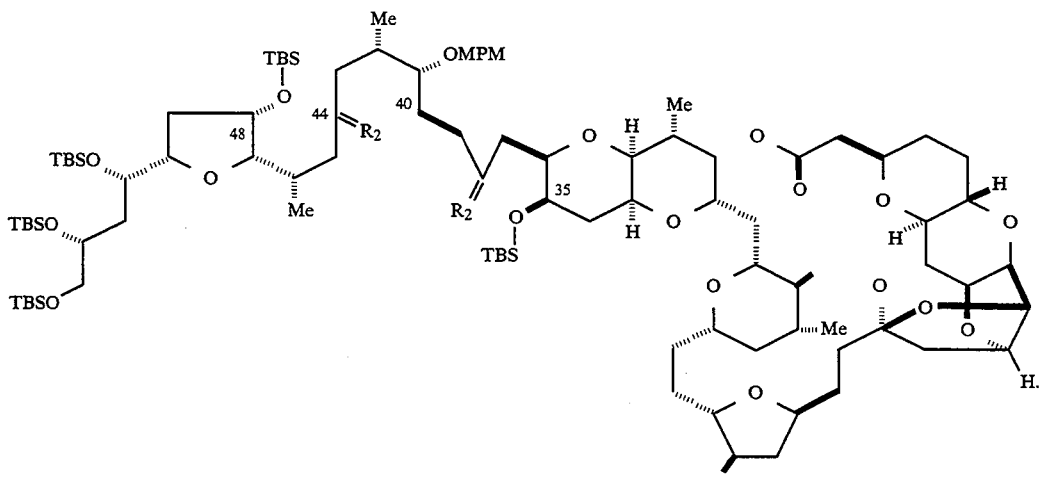

4. A compound having the following structure:

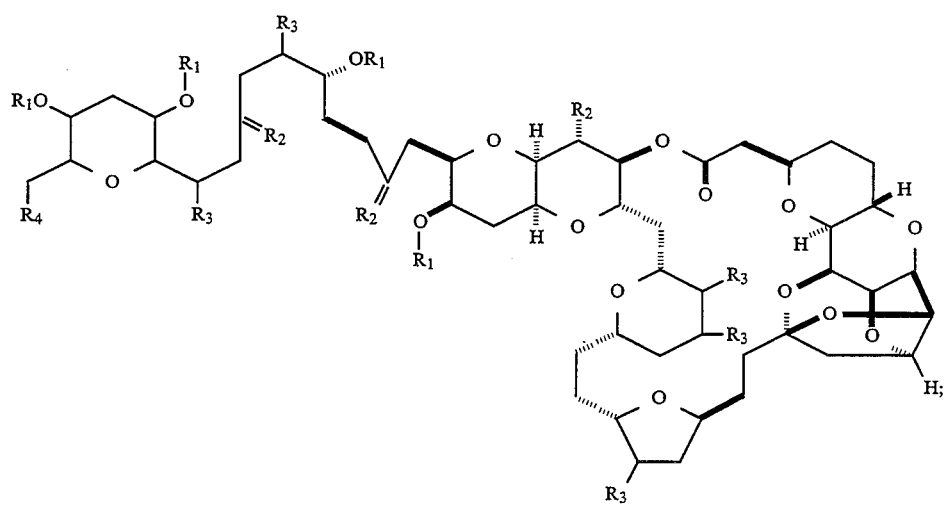

where each $R_1$, independently, is —H or an alcohol protecting group; $R_2$ is O or a protected ketone group; each $R_3$, independently, is —H or an alkyl or alkylene group having 5 or fewer carbon atoms; and $R_4$ is —CH$_2$—OR$_1$, CHO, or CO$_2$D, where D is —H or an alkyl group.

5. The compound of claim 3, wherein said compound has the following structure:

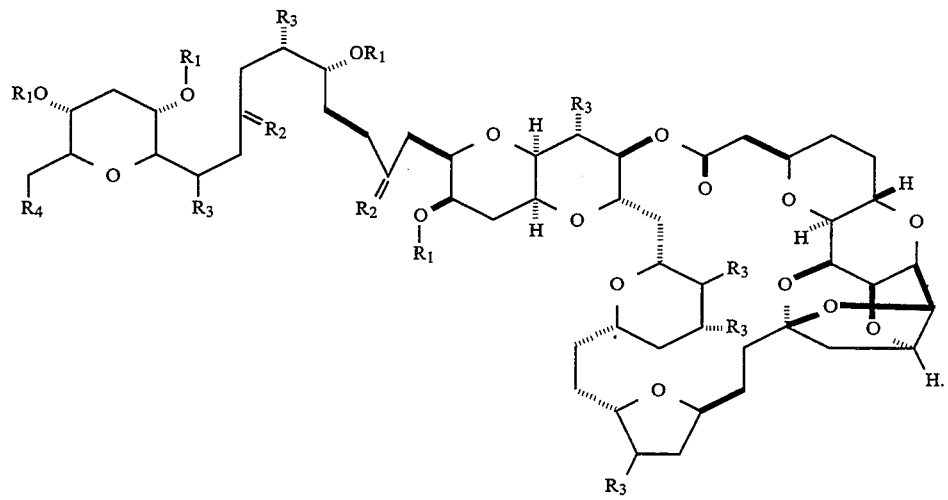

6. The compound of claim 5, wherein said compound has the following structure:

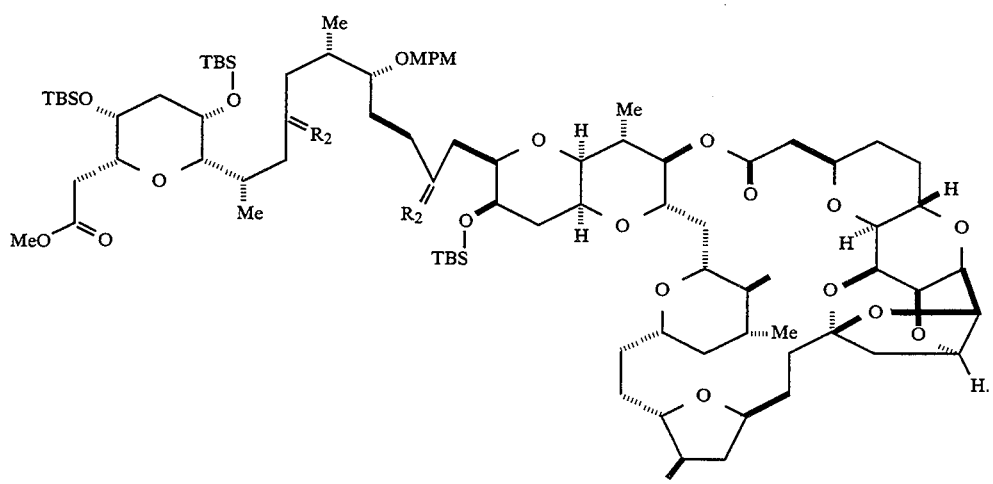

* * * * *

UNITED STATES PATENT AND TRADEMARK OFFICE
CERTIFICATE OF CORRECTION

PATENT NO.   : 5,338,865

DATED        : August 16, 1994

INVENTOR(S)  : Yoshito Kishi, Francis G. Fang,
               Craig J. Forsyth, Paul M. Scola and
               Suk Kyoon Yoon It is certified that error appears in the above-identified patent and that said Letters Patent is hereby corrected as shown below:

Column 1, after the subheading BACKGROUND OF THE INVENTION, insert the following paragraph:

-- This invention was made with government support under Grant No. CA22215 awarded by the National Institutes of Health. The government has certain rights in the invention. --

Signed and Sealed this

Eighth Day of November, 1994

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO.    : 5,338,865

DATED         : August 16, 1994

INVENTOR(S)   : Yoshito Kishi et al.

It is certified that error appears in the above-identified patent and that said Letters Patent is hereby corrected as shown below:

At page 2, right col., line 2, "Medicated" should be --mediated--.

At page 2, right col., line 29, "(32)" should be --(3Z)--.

Col. 1, line 17, "thief" should be --their--.

Col. 5-6, in the last formula, "$R_{21}$" should be --$R_2$--.

Col. 7, line 33, "nohalichondrin" should be --norhalichondrin--.

Col. 7, line 52, "morhalichondrin" should be --norhalichondrin--.

Col. 11, line 17, "rain" should be --min--.

Col. 12, line 3, "stiffed" should be --stirred--.

Col. 12, line 23, "rain" should be --min--.

Col. 12, line 24, "rain" should be --min--.

Col. 12, line 29, "rain" should be --min--.

Col. 13, line 39, "6.2" should be --62--.

Col. 14, line 45, "1" before "NMR" should be --$^1H$--.

Col. 15, line 8, "rain" should be --min--.

Col. 15, line 9, "rain" should be --min--.

UNITED STATES PATENT AND TRADEMARK OFFICE
CERTIFICATE OF CORRECTION

PATENT NO. : 5,338,865

DATED : August 16, 1994

INVENTOR(S) : Yoshito Kishi et al.

It is certified that error appears in the above-identified patent and that said Letters Patent is hereby corrected as shown below:

Col. 15, line 31, before "(7)" insert --293--.

Col. 15, line 49, "rain" should be --min--.

Col. 15, line 50, "rain" should be --min--.

Col. 16, line 28, "rain" should be --min--.

Col. 20, line 29, "rain" should be --min--.

Col. 21, line 60, "$_{Nail}$" should be --NaH--.

Col. 23, line 26, "ca" should be --ea--.

Col. 24, line 50, "herniaoctal" should be --hemiacetal--.

Col. 27, line 20, "12" should be --$I_2$--.

Col. 28, line 19, "1:1" should be --5:1:1--.

Col. 29, line 59, "$[\alpha]_D^{RT} - + 29.7°$" should be --$[\alpha]_D^{RT} = + 29.7°$--.

Col. 30, line 25, "I" should be --1--.

Col. 33, line 56, "$[\alpha]_D:20.0°$" should be --$[\alpha]_D:-20.0°$--.

Col. 35, line 44, "$NaBFH_4$" should be --$NaBH_4$--.

UNITED STATES PATENT AND TRADEMARK OFFICE
CERTIFICATE OF CORRECTION

PATENT NO. : 5,338,865

DATED : August 16, 1994

INVENTOR(S) : Yoshito Kishi et al.

It is certified that error appears in the above-identified patent and that said Letters Patent is hereby corrected as shown below:

Col. 35, line 56, "$[\alpha]_D^{22}$ + 37.7°" should be --$[\alpha]_D$: + 37.7°--.

Col. 36, line 21, "re " should be --re- --.

Col. 40, line 47, insert --8-- under the top formula.

Col. 40, line 55, insert --9-- under the bottom formula.

Col. 40, line 61, "IO" should be --10--.

Col. 40, line 62, "I h" should be --1 h--.

Col. 41, line 30, insert --9-- under the top formula.

Col. 41, line 35, insert --10-- under the bottom formula.

Col. 41, line 49, "(50 mL, (540" should be --(60 mL, (640--.

Col. 42, line 25, insert --11:--.

Col. 42, line 33, "$H_{2o2}$" should be --$H_2O_2$--.

Col. 43, line 11, insert --12:--.

Col. 43, line 61, insert --13:--.

Col. 44, line 49, "C]F" should be --CJF--.

Col. 49, line 32, delete "L", last occurrence.

UNITED STATES PATENT AND TRADEMARK OFFICE
CERTIFICATE OF CORRECTION

PATENT NO.   : 5,338,865
DATED        : August 16, 1994
INVENTOR(S)  : Yoshito Kishi et al.

It is certified that error appears in the above-identified patent and that said Letters Patent is hereby corrected as shown below:

Col. 49, line 64, insert --23:--.

Col. 50, line 40, "23" should be --24--.

Col. 51, line 18, "12" should be --$I_2$--, both occurrences.

Col. 51, line 53, insert --26:--.

Col. 51, line 67, after "gave" insert --8--.

Col. 52, line 7, "alcohols" should be --alcohol--.

Col. 52, line 10, "10g" should be --108--.

Col. 54, line 24, delete "t".

Col. 55, line 29, delete "t".

Col. 58, line 47, "rag" should be --mg--.

Col. 59, line 54, "I-D" should be --H--.

Col. 61, line 8, insert --* X = 2,2,6,6-Tetramethyl-3,5-heptanedione.--.

Col. 63, line 30, before "(3H, s)" insert --0.26--.

Col. 63, line 31, after "(9 H, s" insert --)--.

UNITED STATES PATENT AND TRADEMARK OFFICE
CERTIFICATE OF CORRECTION

PATENT NO. : 5,338,865

DATED : August 16, 1994

INVENTOR(S) : Yoshito Kishi et al.

It is certified that error appears in the above-identified patent and that said Letters Patent is hereby corrected as shown below:

Col. 64, line 4, "0,252" should be --0.252--.

Col. 67, line 23, "443" should be --40--.

Col. 69, line 55, "12A" should be --012A--.

Col. 70, line 6, "4-4" should be --44--.

Col. 70, line 55, "$H_{2o}$" should be --$H_2O$--.

Col. 70, line 59, "ailylic" should be --allylic--.

Signed and Sealed this

First Day of April, 1997

BRUCE LEHMAN

Attest:

Attesting Officer

Commissioner of Patents and Trademarks